United States Patent
Wu et al.

(10) Patent No.: US 8,128,922 B2
(45) Date of Patent: Mar. 6, 2012

(54) SUPERIOR MOLECULAR VACCINE LINKING THE TRANSLOCATION DOMAIN OF A BACTERIAL TOXIN TO AN ANTIGEN

(75) Inventors: Tzyy-Choou Wu, Stevenson, MD (US); Chien-Fu Hung, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 1842 days.

(21) Appl. No.: 10/115,440

(22) Filed: Apr. 4, 2002

(65) Prior Publication Data

US 2004/0086845 A1 May 6, 2004

Related U.S. Application Data

(63) Continuation-in-part of application No. PCT/US00/41422, filed on Oct. 20, 2000, and a continuation-in-part of application No. 09/501,097, filed on Feb. 9, 2000, now Pat. No. 6,734,173, which is a continuation-in-part of application No. 09/421,608, filed on Oct. 20, 1999, now abandoned.

(60) Provisional application No. 60/281,003, filed on Apr. 4, 2001.

(51) Int. Cl.
*A61K 48/00* (2006.01)
*A61K 31/711* (2006.01)
*C07H 21/04* (2006.01)

(52) U.S. Cl. ............... 424/93.21; 424/93.71; 514/44 R; 536/23.4

(58) Field of Classification Search ............... 536/23.4; 514/44; 424/93.21, 93.7; 435/325
See application file for complete search history.

(56) References Cited

U.S. PATENT DOCUMENTS

| | | | |
|---|---|---|---|
| 4,898,730 A | 2/1990 | Levy et al. | |
| 5,217,879 A | 6/1993 | Huang et al. | |
| 5,348,945 A | 9/1994 | Berberian et al. | |
| 5,426,097 A | 6/1995 | Stern et al. | |
| 5,547,846 A | 8/1996 | Bartsch et al. | |
| 5,582,831 A | 12/1996 | Shinitzky | |
| 5,591,716 A | 1/1997 | Siebert et al. | |
| 5,618,536 A | 4/1997 | Lowy et al. | |
| 5,629,161 A | 5/1997 | Muller et al. | |
| 5,674,486 A | 10/1997 | Sobol et al. | |
| 5,744,133 A | 4/1998 | Lathe et al. | |
| 5,750,119 A | 5/1998 | Srivastava | |
| 5,821,088 A | 10/1998 | Darzins et al. | |
| 5,830,464 A | 11/1998 | Srivastava | |
| 5,834,309 A | 11/1998 | Thompson et al. | |
| 5,837,251 A | 11/1998 | Srivastava | |
| 5,844,089 A | 12/1998 | Hoffman et al. | |
| 5,854,202 A | 12/1998 | Dedhar | |
| 5,855,891 A | 1/1999 | Lowy et al. | |
| 5,935,576 A | 8/1999 | Srivastava | |
| 5,948,646 A | 9/1999 | Srivastava | |
| 5,951,975 A | 9/1999 | Falo, Jr. et al. | |
| 5,962,318 A | 10/1999 | Rooney et al. | |
| 5,997,869 A | 12/1999 | Goletz et al. | |
| 6,007,821 A | 12/1999 | Srivastava et al. | |
| 6,013,262 A | 1/2000 | Frazer et al. | |
| 6,017,544 A | 1/2000 | Srivastava | |
| 6,017,735 A | 1/2000 | O'Hare et al. | |
| 6,020,309 A | 2/2000 | Campo et al. | |
| 6,030,618 A | 2/2000 | Srivastava | |
| 6,046,158 A * | 4/2000 | Ariizumi et al. .......... | 514/2 |
| 6,066,716 A | 5/2000 | Wallen et al. | |
| 6,235,523 B1 | 5/2001 | Gajewczyk et al. | |
| 6,331,388 B1 | 12/2001 | Malkovsky et al. | |
| 6,399,070 B1 | 6/2002 | Srivastava et al. | |
| 6,403,080 B1 | 6/2002 | Segal | |
| 6,410,027 B1 | 6/2002 | Srivastava | |
| 6,410,028 B1 | 6/2002 | Srivastava | |
| 6,541,010 B1 | 4/2003 | Johnston et al. | |
| 6,734,173 B1 | 5/2004 | Wu et al. | |
| 7,001,995 B1 | 2/2006 | Neeper et al. | |
| 7,318,928 B2 | 1/2008 | Wu et al. | |
| 7,342,002 B2 | 3/2008 | Wu et al. | |
| 2001/0034042 A1 | 10/2001 | Srivastava | |
| 2002/0064771 A1 | 5/2002 | Zhong et al. | |
| 2002/0091246 A1 | 7/2002 | Pardoll et al. | |
| 2002/0182586 A1 | 12/2002 | Morris et al. | |
| 2004/0028693 A1 | 2/2004 | Wu et al. | |
| 2004/0086845 A1 | 5/2004 | Wu et al. | |
| 2004/0259247 A1 | 12/2004 | Tuschl et al. | |

(Continued)

FOREIGN PATENT DOCUMENTS

CA 2413543 1/2002

(Continued)

OTHER PUBLICATIONS

Donnelly et al (PNAS, 1993, vol. 90, pp. 3530-3534).*
Suzue et al (PNAS, 1997, vol. 94, pp. 13146-13151).*
Abstract of Becker et al (Journal of Cell Biology, 2002, vol. 158, pp. 1277-1285).*
Schutze-Redelmeier et al (Journal of Immunology, 1996, vol. 157, pp. 650-655).*
Lyras et al (Antimicrobial Agents and Chemotherapy, 1996, vol. 40, pp. 2500-2504).*
Carbonetti et al (Infection and Immunity, Feb. 1999, vol. 67, pp. 602-607).*
Celluzzi et al (Journal of Experimental Medicine, 1996, vol. 183, pp. 283-287).*
Tuting et al (Journal of Immunology, Feb. 1998, vol. 160, pp. 1139-1147).*

(Continued)

*Primary Examiner* — Karen A Canella
(74) *Attorney, Agent, or Firm* — Foley Hoag, LLP

(57) ABSTRACT

Nucleic acids encoding a chimeric or fusion polypeptide which polypeptide comprises a first domain comprising a translocation polypeptide; and a second domain comprising at least one antigenic peptide are disclosed. The preferred translocation polypeptide is a bacterial toxin translocation polypeptide, such as domain II of *Pseudomonas aeruginosa* exotoxin A (ETA(dII)). Such nucleic acids, expression vectors thereof, and cells expressing these vectors are used as vaccine compositions in a method for enhancing an antigen specific immune response, a method of increasing the numbers of CD8+ CTLs specific for a selected desired antigen in a subject, or a method of inhibiting the growth of a tumor in a subject.

36 Claims, 4 Drawing Sheets

U.S. PATENT DOCUMENTS

| | | | |
|---|---|---|---|
| 2005/0048467 | A1 | 3/2005 | Sastry et al. |
| 2005/0054820 | A1 | 3/2005 | Wu et al. |
| 2005/0277605 | A1 | 12/2005 | Wu et al. |
| 2007/0026076 | A1 | 2/2007 | Wu et al. |

FOREIGN PATENT DOCUMENTS

| | | | |
|---|---|---|---|
| EP | 0 763 740 | | 3/1997 |
| WO | WO-89/12455 | | 12/1989 |
| WO | WO-92/05248 | | 4/1992 |
| WO | WO-93/20844 | | 10/1993 |
| WO | WO-94/04696 | | 3/1994 |
| WO | WO 94/04696 | | 3/1994 |
| WO | WO-94/29459 | | 12/1994 |
| WO | WO95/17212 | * | 6/1995 |
| WO | WO-96/36643 | | 11/1996 |
| WO | WO97/03703 | * | 2/1997 |
| WO | WO-97/06685 | | 2/1997 |
| WO | WO 97/41440 | * | 11/1997 |
| WO | WO 98/23735 | | 6/1998 |
| WO | WO-98/32866 | | 7/1998 |
| WO | WO-98/48003 | | 10/1998 |
| WO | WO 99/07860 | | 2/1999 |
| WO | WO 99/07869 | | 2/1999 |
| WO | WO 99/42472 | | 8/1999 |
| WO | WO-99/58658 | | 11/1999 |
| WO | WO-99/65940 | | 12/1999 |
| WO | WO-01/29233 | | 4/2001 |
| WO | WO-02/09645 | | 2/2002 |
| WO | WO-02/12281 | | 2/2002 |
| WO | WO-02/061113 | | 8/2002 |
| WO | WO-02/074920 | | 9/2002 |
| WO | WO-03/008543 | | 1/2003 |
| WO | WO-03/083052 | | 10/2003 |
| WO | WO-03/085085 | | 10/2003 |
| WO | WO-2004/030636 | | 4/2004 |
| WO | WO-2004/060304 | | 7/2004 |
| WO | WO-2004/098526 | | 11/2004 |
| WO | WO-2005/047501 | | 5/2005 |
| WO | WO-2005/081716 | | 9/2005 |
| WO | WO-2006/073970 | | 7/2006 |
| WO | WO-2006/081323 | | 8/2006 |

OTHER PUBLICATIONS

Babiuk et al., "Immunization of animals: from DNA to the dinner plate," Veterinary Immunology and Immunopathology, 72:189-202 (1999).
Breitburd et al., "Human papillomavirus vaccines," Cancer Biology, 9:431-445 (1999).
Hasan et al., "Nucleic acid immunization: concepts and techniques associated with third generation vaccines," Journal of Immunological Methods, 229:1-22 (1999).
Becker et al., CD40, an extracellular receptor for binding and uptake of hsp 70-peptide complexes, Abstract, Journal of Cell Biology 158(7):1277-1285 (2002).
Carbonetti et al., "Intracellular Delivery of a Cytolytic T-Lymphocyte Epitope Peptide by Pertussis Toxin to Major Histocompatibioity Complex Class I without Involvement of the Cytosolic Class I Antigen Processing Pathway," Infection and Immunity 67(2):602-607 (1999).
Celluzzi et al., "Peptide-pulsed Dendritic Cells Induce Antigen-specific, CTL-mediated Protective Tumor Immunity," J. Exp. Med. 183:283-287 (1996).
Chen, Chien-Hung et al., "Enhancement of DNA Vaccine Potency by Linkage of Antigen Gene to an HSP70 Gene," Cancer Research, 60(4):1035-1042 (2000).
Chu et al., "Cancer Immunotherapy Using Adjuvant-Free, Fusion Protein Encoding M. Golvis BCG HSP65 and HPV16 E7," FASEB Journal 12(5), Mar. 20, 1998 Abstract XP000960840.
Chu et al., Immunotherapy of a human papillomavirus (HPV) type 16 E7-expressing tumour by administration of fusion protein comprising Mycobacterium bovis bacille Calmette-Guerin (BCG) hsp65 and HPV16 E7, Clin Exp Immunol. Aug. 2000;121(2):216-25.
Davidoff et al., "Immune Response to P53 is Dependent upon P53/HSP70 Complexes in Breast Cancers," Proceedings of the National Academy of Sciences of USA, 89(8):3442 (1992).

Donnelly et al., "Targeted delivery of peptide epitopes to class I major histocompatibility molecules by a modified *Pseudomonas* exotoxin," Proc. Natl. Acad. Sci. USA 90:3530-3534 (1993).
Elsaghier et al., "Localisation of Linear Epitopes at the Carboxy-Terminal End of the Mycobacterial 71 KDA Heat Shock Protein," Molecular Immunology 29(9):1153-1156 (1992).
Fomsgaard et al., "Improved Humoral and Cellular Immune Responses Against the gp120 V3 Loop of HIV-1 Following Genetic Immunization with a Chimeric DNA Vaccine Encoding the V3 Inserted into the Hepatitis B Surface Antigen," Scand J. Immunol., 47(4):289-95 (1998).
Suzue et al., "Adjuvant-Free HSP70 Fusion Protein System Elicits Humoral and Cellular Immune Responses to HIV-1," Journal of Immunology 156:873-879 (1996).
Schutze-Redelmeier et al., "Introduction of Exogenous Antigens into the MHC Class I Processing and Presentation Pathway by *Drosophila* Antennapedia Homeodomain Primes Cytotoxic T Cells in Vivo," Journal of Immunology 157:650-655 (1996) (Abstract).
Lyras and Rood, "Genetic Organization and Distribution of Tetracycline Resistance Determinants in *Clostridium perfringens*," Antimicrobial Agents and Chemotherapy 40:2500-2504 (1996).
Suzue et al., "Heat shock fusion proteins as vehicles for antigen delivery into the major histocompatibility complex class I presentation pathway," Proc. Natl. Acad. Sci. USA 94:13146-13151 (1997).
Tuting et al., "Autologous Human Monocyte-Derived Dendritic Cells Genetically Modified to Express Melanoma Antigens Elicit Primary Cytotoxic T Cell Responses In Vitro: Enhancement by Cotransfection of Genes Encoding the Th1-Biasing Cytokines IL-12 and IFN-$\alpha^1$," Journal of Immunology 160:1139-1147 (1998).
Anthony et al., "Priming of CD8 CTL Effector Cells in Mice by Immunizationwith a Stress-Protein-Influenza Virus Nucleoprotein Fusion Molecule," Vaccine (17)373-383. 1999.
Ausbel, et al., Current Protocols in Molecular Biology, John Wiley & Sons, 1989.
Boyle et al. "Enhanced responses to a DNA vaccine encoding a fusion antigen that is directed to sites of immune induction," Nature. vol. 392, p. 408-411. 1998.
Banchereau. et al. "Dendritic Cells: Therapeutic Potentials," vol. 18, No. 2, p. 313-326. 1997.
Biragyn et al., "Genetic fusion of chemokines to a self tumor antigen induces protective, T-Cell dependent antitumor immunity," Nature Biotechnology. vol. 17, p. 253-258, 1993.
Blachere et al., "Heat shock Protein-peptide complexes, Reconstituted in vitro, Elicit Peptide-specific cytotoxic T Lymphocyte Response and Tumor Immunity," J. Exp. Med. vol. 186, No. 8, p. 1315-1322. 1997.
Blachere, et al. "Heat shock proteins against cancer," J. of Immunotherapy. 14: 352-356. 1993.
Bueler et al., Induction of Antigen-Specific Tumor Immunity by Genetic and Cellular Vaccines against MACE: Enhanced Tumor Protection by Coexpression of Granulocyte-Macrophage Colony-Stimulating Factor and B7-1, Molecular Medicine, 1996, vol. 2, No. 5, p. 545-555.
Chen et al., Design of a genetic immunotoxin to eliminate toxin immunogenicity, Gene Therapy, 1992, vol. 2, p. 116-123.
Cho et al., Enhanced cellular immunity to hepatitis C virus nonstructural proteins by codelivery of granulocyte macrophage-colony stimulating factor gene in intramuscular DNA immunization, Vaccine, 1999, vol. 17, p. 1136-1144.
Chow et al., Development of Thi1 and Th2 Populations and the Nature of Immune Responses to Hepatitis B Virus DNA Vaccines Can Be Modulated by Codelivery of Various Cytokine Genes, The Journal of Immunology, 1998, vol. 160, No. 3, p. 1320-1329.
Ciupitu et al., Immunization with a Lymphocytec Choriomeningitis Virus Peptide Mixed Heat Sbcok Protein 70 Results in Protective Antiviral Immunity and Specific Cytotoxic T Lymphocytes, J. Exp. Med., 1998, vol. 187, No. 5, p. 685-691.
Corr et al., Costimulation Provided by DNA Immunization Enhances Antitumor Immunity, The Journal of Immunology, 1997, vol. 159, No. 10, p. 4999-5004.

Deninsky et al., A Wide Range of Human Cancers Express Interleukin 4 (IL-4) Receptors That Can Be Targeted with Chimeric Toxin Composed of IL-4 and *Pseudomonas Exotoxin*, The Journal of Biological Chemistry, 1993, vol. 268. No. 19, p. 14065-14070.

Donnelly et al., DNA Vaccines, Annual Review of Immunology, 1997, vol. 15, p. 617-48.

Donnelly et al., Targeted delivery of peptide epitopes to class I major histocompatibility molecules by a modified *Pseudomonas exotoxin*, Proc. Natl. Acad. Sci. USA, 1993, vol. 90, pp. 3530-3534.

Fominaya et al., Target Cell-specific DNA Transfer Mediated by a Chimeric Multidomain Protein, The Journal of Biological Chemistry, 1996, vol. 271, No. 18, pp. 10560-10568.

Geissler et al., Enhancement of Cellular and Humoral Immune Responses to Hepatitis C Virus Protein Using DNA Based Vaccines Augmented with Cytokine-Expressing Plasmids, The Journal of Immunology, 1997, vol. 158, No. 3, p. 1231-1237.

Goletz et al., Delivery of Antigens to the MHC Class I Pathway Using Bacterial Toxins, Human Immunology, 1997, vol. 54, p. 129-136.

Heikema et al. Generation of heat shock protein-based vaccines by intracellular loading of gp96 with antigen peptides, Immunology Letters, 1997, vol. 57, Nos. 1-3, p. 69-74.

Iwasaki et al., Enhanced CTL Responses Mediated by Plasmid DNA Immunogens Encoding Costimulatory Molecules and Cytokines, The Journal of Immunology, 1997, vol. 158, No. 10, pp. 4591-4601.

Janetzki et al. Generation of Tumor-Specific Cytotoxic T Lymphocytes and Memory T Cells by Immunization with Tumor-Derived Heat Shock Protein gp96, Journal of Immunotherapy, 1998, vol. 21, No. 4, pp. 269-276.

Kim et al., Cytokine Molecular Adjuvants Modulate Immune Responses Induced by DNA Vaccine Constructs for HIV-1 and SIV, Journal of Interferon and Cytokine Research, 1999, vol. 19, No. 1, pp. 77-84.

King et al, DNA vaccines with single-chain Fv fused to fragment C of tetanus toxin induce protective immunity against lymphoma and myeloma, Nature Medicine, 1998, vol. 4, No. 11, pp. 1281-1286.

Kita et al., Frequent Gene Expression of Granulocyte Colony-Stimulating Factor (G-CSF) Receptor in CD7+ Surface CD3 - Acute Lymphoblastic Leukaemia, Leukemia, 1993, vol. 7, No. 8, pp, 1184-1190.

Klinman et al., Contribution of CpG Motifs to the Immunogenicity of DNA vaccines, The Journal of Immunology, 1997, vol. 158, No. 8, pp. 3635-3639.

Larregina et al., Pattern of cytokine receptors expressed by human dendritic cells migrated from dermal explants, Immunology, 1997, vol. 91, pp. 303-313.

Lee et al., DNA inoculations with HIV-1 recombinant genomes that express cytokine genes enbance HIV-1 specific immune responses, Vaccine, 1999, Vo, 17, pp. 473-479.

Lee et al., Optimal Induction of Hepatitis C Virus Envelope-Specific Immunity by BiCistronic Plasmid DNA Inoculation with the Granulocyte-Macrophage Colony-Stimulating Factor Gene, 1998, vol. 72, No. 10, pp. 8430-8436.

Lin et al., Treatement of Established Tumors with a Novel Vaccine That Enhances Major Histcompatibility Class 11 Presentation of Tumor Antigen, Cancer Research, 1996, vol. 56, No. 1, pp. 21-26.

Dialynas et al., Characterization of the Murine T Cell Surface Molecule Designated L3T4, Identified by Monocolonal Antibody GK1.5: Simlarity of L3T4 to the Human LEU-3/T4 Molecule, Nov. 1983, vol. 131, No. 5, p. 2445-2451.

Higgins et al., Fast and Sensitive Multiple Sequence Alignments on a Microcomputer, CABIOS 5(2):151-153, 1989.

Hannum et al., Ligand for FLT3/FLK2 Receptor Tyrosine Kinase Regulates Growth of Haematopoietic Stem Cells and is Encoded by Variant RNAs, 1994, Nature 368:643-8.

Koo et al., the NK-1.1(-30 ) Mouse: A Model to Study Differentiation of Murine NK Cells, 1986, J. Imnnunol. 125:2665-2672.

Maraskovsky et al., Dramatic Increase in the Numbers of Funtionally Mature Dendritic Cells in Flt-3 Ligand-treated Mice: Multiple Dendritie Cell Subpopulations Identified, Nov. 1996, J. Exp. Med., vol. 184, p. 1953-1962.

McKenzie et al., Sequence and Immunogenicity of the 70-kDa Heat Shock Protein of Mycobacterium leprae, 1991, vol. 147, No. 1, p. 312-319.

Mrsny et al., Mucosal administration of a chimera composed of *Pseudomonas exotoxin* and the gp120 loop sequence of HIV-1 induces both salivary and serum antibody responses, Vaccine, 1999, vol. 17, p. 1425-1433.

Okada et al., Intranasal Immunization of a DNA Vaccine with IL-12- and Granulocyte-Macrophage Colony-Stimulating Factor (GM-CSF)-Expressing Plasmids in Lipsomes Induces Strong Mucosal and Cell Mediated Immune Responses Against HIV-1 Antigens, The Journal of Immunology, 1997, vol. 159, No. 7, p. 3638-3647.

Opershcall et al., Enhanced protection against viral infection by co-administration of plasmid DNA coding for viral antigen and cytokines in mice, Journal of Clinical Virology, 1999, vol. 13, p. 17-27.

Pan et al., A recombinant Listeria Monocytogenes Vaccine Expressing a Model Tumour Antigen Protects Mice Against Lethal Tumour Cell Challenge and Causes Regression of Established Tumours, Nature Medicine, May 1995, vol. 1, No. 5.

Pan et al., Regression of Established Tumors in Mice Mediated by the Oral Administration of a Recombinant Listeria monocytogenes Vaccine, Cancer Research, 1995, 55(21):4776-4779.

Pardoll et al., Exposing the Immunology of Naked DNA Vaccines, Immunity, 1995, vol. 3, p. 165-169.

Praepiorka et al., Heat shock protein peptide complexes as Immunotherapy for human cancer, Molecular Medicine Today (Reviews), 1998, p. 478-484.

Robinson et al., DNA Vaccines, Immunology, 1997, vol. 9, p. 271-283.

Rodriguez et al., DNA Immunization with Minigenes: Low Frequency of Memory Cytotoxic T Lymphocytes and Inefficient Antiviral Protection Are Rectified by Ubiquitination, Journal of Virology, 1998, vol. 72, No. 6, p. 5174-5181.

Sarmiento et al., IgCx or IgM Monoclonal Antibodies Reactive with Different Determinants of the Molecular Complex Bearing LYT 2 Antigen Block T Cell Mediated Cytolysis in the Absence of Complement, 1980, vol. 125, No. 6, 2665-2672.

Sun et al., Enhancement of protective humoral (Th2) and cell mediated (Th1) immune responses against herpes simplex virus-2 co-delivery of granulocyte-macrophage colony-stimulating factor expression cassettes, Eur. J. Immunol., 1998, vol. 28, p. 3530-3540.

Srivastava et al., The Serologically Unique Cell Surface Antigen of Zajdela Ascitic Heptoma is also its Tumor-Associated Transplantation Antigen, Int. J. Cancer, 1984, vol. 33, p. 417-422.

Srivastava et al., Tumor rejection antigens of chemically induced sarcomas of inbred mice, Proc. Natl.-Acad. Sci. USA, 1986, vol. 83, p. 3407-3411.

Srivastava et al., Heat Chock Proteins Come of Age: Primitive Functions Acquire New Roles in an Adaptive World, Immunity, 1998, vol. 8, p. 657-665.

Steinman et al., The Sensitization Phase of T-Cell-mediated Immunity, Annals of the New York Academy of Sciences, vol. 546, p. 80-90, 1988.

Stevenson et al., Idiotypic DNA Vaccines Against B-cell Lymphoma, Immunological Reviews, 1995, No. 145, p. 211-228.

Suto et al., A Mechanism for the Specific Immunagenicity of Heat Shcck Protein-Chaperoned Peptides, Science, 1995, vol. 269, p. 1585-1588.

Suzue et al., Heat shock fusion proteins as vehicles for antigen delivery into the major histomtpatibility complex class I presentation pathway, Proc. Natl. Acad. Sci. USA, 1997, vol. 94, p. 13146-13151.

Suzue et al., Adjuvant-Free hsp70 Fusion Protein System Elicits Humoral and Cellular Immune Responses to HIV-1 p24', The Journal of Immunology, 1946, vol. 156, No. 2, p. 873-879.

Syrengelas et al., DNA immunization induces protective immunity against B-cell lymphoma, Nature Medicine, 1996, vol. 2, No. 9, p. 1038-1041.

Tamura et al., Immunotherapy of Tumors with Autologous Tumor-Derived Heat Shock Protein Preparations, Science, 1997, vol. 278, p. 117-120.

Tobery et al., Targeting of HIV-1 antigen for rapid intracellular degradation enhances cytotoxic T lymphocyte (CTL) recognition and the induction of De Novo CTL responses in Vivo after immunization, J. Exp. Med., 1997, vol. 185, No. 5, p. 909-920.

Udono et al., Cellular requirements for tumor-specific immunity elicited by hear shock proteins: Tumor rejection antigen gp96 primes CD8+ T cells in vivo, Proc. Natl. Acad. Sci. USA, 1994, vol. 91, p. 3077-3081.

Udono et al., Comparison of Tumor specific immunogenicities of stress-induced proteins gp96, hsp90, and hsp70', The Journal of Immunology, 1994, vol. 152, No. 11, p. 5398-5403.

Ulmer et al., Presentation of an exogenous antigen by major histocompatibility complex class I molecules, Eur. J. Immunol., 1994, vol. 24, p. 1590-1596.

Weiss et al. A plasmid encoding murine granulocyte-macrophage colony-stimulating factor increases protection conferred by a malaria DNA vaccine, The Journal of Immunology, 1998, vol. 161, No. 5, p. 2625-2330.

Maecker et al., DNA vaccination with cytokine fusion constructs biases the immune response to ovalbumin, 1997, 15(15):1687-1696 (Abstract).

Lim et al., Vaccination with an ovalbumin/interleukin-4 fusion DNA efficiently induces Th2 cell-mediated immune responses in an ovalbumin-specific manner, Arch. Pharm. Res. 21(5):537-542 (Abstract), 1998.

Forni et al. Cytokine gene-engineered vaccines, Curr. Opin. Mol. Ther. Feb. 1999;1(1):34-38 (Abstract).

Biragyn et al., Genetic fusion of chemokines to a self tumor antigen induces protective, T-cell dependent antitumor immunity, Nature Biotechnology, 1999 17(3):253-258 (Abstract).

Oltersdorf et al., "Identification of Human Papillomavirus Type 16 E7 Protein by Monoclonal Antibodies," J. Gen. Virol., 68:2933-2938 (1987).

Aguiar et al., "Enhancement of the immune response in rabbits to a malaria DNA vaccine by immunization with a needle-free jet device," Vaccine, 20:275-280 (2001).

Alexander et al., "Development of High Potency Universal DR-Restricted Helper Epitopes by Modification of High Affinity DR-Blocking Peptides," Immunity, 1:751-761 (1994).

Anonymous: "E7 vaccine (NSC 723254)," Timeless Success Story, Online, XP002394109 (2002).

Asea et al., "Novel Signal Transduction Pathway Utilized by Extracellular HSP70," Journal of Biological Chemistry, 277(7):15028-15034 (2002).

Bae et al., "Therapeutic Synergy of Human Papillomavirus E7 Subunit Vaccines plus Cisplatin in an Animal Tumor Model: Casual Involvement of Increased Sensitivity of Cisplatin-Treated Tumors to CTL-Mediated Killing in Therapeutic Synergy," Clin. Cancer Res., 13(1):341-349 (2007).

Banu et al., "Modulation of Haematopoietic Progenitor Development by FLT-3 Ligand,"Cytokine, 11(9):679-688 (1999).

Barrios et al., "Mycobacterial heat-shock proteins as carrier molecules. II: The use of the 70-kDa mycobacterial heat-shock protein as carrier for conjugated vaccines can circumvent the need for adjuvants and Bacillus Calmette Guerin priming," Eur. J. Immunol., 22:1365-1372 (1992).

Basu et al.,"Calreticulin, A Peptide-Binding Chaperone of the Endoplasmic Reticulum, Elicits Tumor- and Peptide-Specific Immunity," Journal of Experimental Medicine, 189(5):797-802 (1999).

Beissbarth et al., "Increased efficiency of folding and peptide loading of mutant MHC class I molecules," Eur. J. Immunol., 30:1203-1213 (2000).

Bennett et al., "Calnexin Association Is Not Sufficient to Protect T Cell Receptor α Proteins from Rapid Degradation in CD4+CD8+Thymocytes," The Journal of Biological Chemistry 273(37):23674-23680 (1998).

Benton et al., "DNA Vaccine Strategies for the Treatment of Cancer," Curr Top Microbiol Immunol. 226:1-20 (1998).

Bhoola et al., "Diagnosis and management of epithelial ovarian cancer," Obstet. Gynecol., 107(6):1399-1410 (2006).

Bohm et al., "Routes of plasmid DNA vaccination that prime murine humoral and cellular immune responses," Vaccine, 16:949-954 (1998).

Bredenbeek et al., "Sindbis Virus Expression Vectors: Packaging of RNA Replicons by Using Defective Helper RNAs," Journal of Virology, 67(11):6439-6446 (1993).

Brossart et al., "Identification of HLA-A2-Restricted T-Cell Epitopes Derived From the MUC1 Tumor Antigen for Broadly Applicable Vaccine Therapies," Blood, 93(12):4309-4317 (1999).

Buck et al., "Efficient Intracellular Assembly of Papillomaviral Vectors," Journal of Virology, 78(2):751-757 (2004).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 111:2129-2138 (1990).

Cavill et al., "Generation of a Monoclonal Antibody Against Human Calreticulin by Immunization with a Recombinant Calreticulin Fusion Protein: Application in Paraffin-Embedded Sections," Appl. Immunohistochemistry & Molecular Morphology 7(2):150-155 (1999).

Chang et al., "Cancer Immunotherapy Using Irradiated Tumor Cells Secreting Heat Shock Protein 70," Cancer Res., 67(20):10047-10057 (2007).

Chang, C-L. et al., "Control of human mesothelin-expressing tumors by DNA vaccines." Gene Therapy 1-10 (2007).

Chavin, K. et al.; "Obesity Induces Expression of Uncoupling Protein-2 in Hepatocytes and Promoates Liver ATP Depletion." J. Biol. Chem. 274(9):5692-5700 (1999).

Chen et al., "Human pappillomavirus type 16 nucleoprotein E7 is a tumor rejection antigen," PNAS, 88:110-114 (1991).

Chen et al., "Induction of Cytotoxic T Lymphocytes Specific for a Syngeneic Tumor Expressing the E6 Oncoprotein of Human Papillomavirus Type 16," Journal of Immunology, 148:2617-2621 (1992).

Chen et al., "Mycobacterial heat shock protein 65 enhances antigen cross-presentation in dendritic cells independent of Toll-like receptor 4 signaling," Journal of Leukocyte Biology, 75:260-266 (2004).

Chen, C-H. et al. "Recombinant DNA vaccines protect against tumors that are resistant to recombinant vaccinia vaccines containing the same gene." Gene Therapy 8:128-138 (2001).

Chen, C-H. et al., "Antigen-specific immunotherapy for human papillomavirus 16 E7-expressing tumors grown in the liver." Journal of Hepatology 33:91-98 (2000).

Chen, C-H. et al., "Boosting with recombinant vaccinia increases HPV-16 E7-specific T cell precursor frequencies of HPV-16 E7-expressing DNA vaccines," Vaccine 18:2015-2022 (2000).

Chen, C-H. et al., "Gene gun-mediated DNA vaccination induces antitumor immunity against human papillomavirus type 16 E7-expressing murine tumor metastases in the liver and lungs," Gene Therapy 6:1972-1981 (1999).

Chen, W. et al., "Modulatory Effects of the Human Heat Shock Protein 70 on DNA Vaccination," J. Biomed. Sci., 7(5):412-419 (2000).

Cheng, W. et al., "CD8+ T cells, NK cells and IFN-γare important for control of tumor with downregulated MHC class I expression by DNA vaccination," Gene Therapy 10:1311-1320, (2003).

Cheng, W.F., et al/.; "Characterization of DNA Vaccines Encoding the Domains of Calreticulin for Their Ability to Elicit Tumor-Specific Immunity and Antiangiogenesis," Vaccine 23:3864-3874 (2005).

Cheng, W-F. et al. "Enhancement of Sindbis Virus Self-Replicating RNA Vaccine Potency by Linkage of Mycobacterium tuberculosis Heat Shock Protein 70 Gene to an Antigen Gene," Journal of Immunology, 166:6218-6226 (2001).

Cheng, W-F. et al., "Cancer Immunotherapy Using Sindbis Virus Replicon Particles Encoding a VP22-Antigen Fusion." Human Gene Therapy. 13:553-568 (2002).

Cheng, W-F. et al., "Enhancement of Sindbis Virus Self-Replicating RNA Vaccine Potency by Targeting Antigen to Endosomal/Lysosomal Compartments," Human Gene Therapy 12:235-252 (2001).

Cheng, W-F. et al., "Enhancement of Sindbis Virus Self-Replicating RNA Vaccine Potency by Linkage of Herpes Simplex Virus Type 1 VP22 Protein to Antigen." Journal of Virology, 75(5):2368-2376 (2001).

Cheng et al. (Report on Results of Monographic Study # NSC91-2314-B-002-377, National Taiwan University, National Scientific Committee, available to public Oct. 31, 2003).

Cheng et al., "Bax-independent inhibition of apoptosis by Bcl-$x_L$," Nature, 379(8):554-556 (1996).

Cheng, W-F. et al., "Repeated DNA Vaccinations Elicited Qualitatively Different Cytotoxic T Lymphocytes and Improved Protective Antitumor Effects." J Biomed Sci 9:675-687 (2002).

Cheng, W-F. et al., "Tumor-specific immunity and antiangiogenesis generated by a DNA vaccine encoding calreticulin linked to a tumor antigen." J. Clin. Invest. 108:669-678 (2001).

Coukos et al., "Immunotherapy for gynaecological malignancies," Expert Opin. Biol. Ther., 5(9):1193-1210 (2005).

Crum et al., "Vaccines for Cervical Cancer," Cancer Journal from Scientific American, 9(5):368-376 (2003).

de Jong et al., "Enhancement of human papillomavirus (HPV) type 16 E6 and E7-specific T-cell immunity in healthy volunteers through vaccination with TA-CIN, an HPV16 L2E7E6 fusion protein vaccine," Vaccine, 20:3456-3464 (2002).

Devaraj, K. et al., "Development of HPV Vaccines for HPV-Associated Head and Neck Squamous Cell Carcinoma," Crit. Rev. Oral Biol. Med. 14(5):345-362, (2003).

Donnelly et al., "DNA Vaccines: Progress and Challenges," J. Immunol., 175:633-639 (2005).

Drake et al., "Assessing tumor growth and distribution in a model of prostate cancer metastasis using bioluminescence imaging," Clin. Exp. Metastasis, 22:674-684 (2005).

Eggleton, P. and Llewellyn, D.H., "Pathophysiological Roles of Calreticulin in Autoimmune Disease," Scand. J. Immunol. 49:466-473 (1999).

Eiben et al., "Establishment of an HLA-a*0201 Human Papillovavrus Type 16 Tumor Model to Determine the Efficacy of Vaccination Strategies in HLA-A*0201 Transgenic Mice," Cancer Research, 62:5792-5799 (2002).

Eisenbraun et al., "Examination of parameters affecting the elicitation of humoral immune responses by particle bombardment-mediated genetic immunization," DNA Cell Biol., 12(9):791-797 (1993).

Elliott et al., "Intercellular trafficking and protein delivery by a herpesvirus structural protein," Cell, 88(2):223-233 (1997).

Feltkamp et al., "Vaccination with cytotoxic T lymphocyte epitope-containing peptide protects against a tumor induced by human papillomavirus type 16-transformed cells," Eur. J. Immunol., 23(9):2242-2249 (1993).

Fernando et al., "Expression, purification and immunological characterization of the transforming protein E7, from cervical cancer-associated human papilloma virus type 16," Clin. Exp. Immunol., 115:397-403 (1999).

Flohe et al., "Human Heat Shock Protein 60 Induces Maturation of Dendritic Cells Versus a Th1-Promoting Phenotype," The Journal of Immunology, 170:2340-2348 (2003).

Frydman et al., "Folding of nascent polypeptide chains in a high molecular mass assembly with molecular chaperones," Nature, 370:111-117 (1994).

Galloway, D.A., "Papillomavirus vaccines in clinical trials," Lancet Infect. Dis., 3(8):469-475 (2003).

Gao et al., "Immune response to human papillomavirus type 16 E6 gene in a live vaccinia vector," Journal of General Virology, 75:157-164 (1994).

Gavarasana et al., "Prevention of Carcinoma of Cervix with Human Papillomavirus Vaccine," Indian Journal of Cancer, 37:57-66 (2000).

Georgopoulos et al., "Role of the Major Heat Shock Proteins as Molecular Chaperones," Annu. Rev. Cell. Bio., 9:601-634 (1993).

Grandis et al., "Head and Neck Cancer: Meeting Summary and Research Opportunities," Cancer Research, 64:8126-8129 (2004).

Graner et al., "Immunoprotective Activities of Multiple Chaperone Proteins Isolated from Murine B-Cell Leukemia/Lymphoma," Clinical Cancer Research, 6:909-915 (2000).

Haas et al., "cDNA cloning of the immunoglobulin heavy chain binding protein," Proc. Natl. Acad. Sci. USA, 85:2250-2254 (1988).

Hansen et al., "Structural features of MHC class I molecules that might facilitate alternative pathways of presentation," Immunology Today, 21(2):83-88 (2000).

Harris et al., "Calreticulin and Calnexin Interact with Different Protein and Glycan Determinants During the Assembly of MHC Class I," The Journal of Immunology 160:5404-5409 (1998).

Hartl, F., "Molecular chaperones in cellular protein folding," Nature, 381:571-579 (1996).

Hauser et al., "Secretory heat-shock protein as a dendritic cell-targeting molecule: a new strategy to enhance the potency of genetic vaccines," Gene Therapy, 11:924-932 (2004.

He et al., "Viral Recombinant Vaccines to the E6 and E7 Antigens of HPV-16," Virology, 270:146-161 (2000).

Heller, J. et al., "Tetra-O-methyl Nordihydroguaiaretic Acid Induces G2 Arrest in Mammalian Cells and Exhibits Tumoricidal Activity in Vivo," Cancer Research 61:5499-5504, (2001).

Hendrick et al., "Molecular chaperone functions of heat-shock proteins," Annu. Rev. Biochem., 62:349-384 (1993).

Hokey et al., "DNA vaccines for HIV: challenges and opportunities," Springer Semin. Immunopathol., 28(3):267-279 (2006).

Hope et al., "Flt-3 Ligand, in Combination with Bovine Granulocyte-Macrophage Colony-Stimulating Factor and Interleukin-4, Promotes the Growth of Bovine Bone Marrow Derived Dendritic Cells," Scand. J. Immunol., 51:60-66 (2000).

Hsieh, C-J. et al., "Enhancement of vaccinia vaccine potency by linkage of tumor antigen gene to gene encoding calreticulin." Vaccine 22:3993-4001. (2004).

Hsu, K-F. et al., "Enhancement of suicidal DNA vaccine potency by linking Mycobacterium tuberculosis heat shock protein 70 to an antigen." Gene Therapy 8, 376-383 (2001).

Huang, C-C. et al., "Generation of Type-Specific Probes for the Detection of Single-Copy Human Papillomavirus by a Novel In Situ Hybridization Method," Mod. Pathol. 11(10):971-977 (1998).

Huang, C-C. et al., "HPV In Situ Hybridization with Catalyzed Signal Amplification and Polymerase Chain Reaction in Establishing Cerebellar Metastasis of a Cervical Carcinoma." Human Pathology, 30(5):587-591. (1999).

Huang, C-H. et al. "Cancer Immunotherapy using a DNA vaccine encoding a single-chain trimer of MHC class I linked to an HPV-16 E6 immunodominant CTL epitope." Gene Therapy. 12:1180-1186 (2005).

Huang, Q. et al., "In Vivo Cytotoxic T Lymphocyte Elicitation by Mycobacterial Heat Shock Protein 70 Fusion Proteins Maps to a Discrete Domain and Is CD4+T Cell Independent," J. Exp. Med., 191(2):403-408 (2000).

Hung et al., "A DNA vaccine encoding a single-chain trimer of HLA-A2 linked to human mesothelin peptide generates anti-tumor effects against human mesothelin-expressing tumors," Vaccine, 25(1):127-135 (2007).

Hung, C-F. et al., "Cancer Immunotherapy Using a DNA Vaccine Encoding the Translocation Domain of a Bacterial Toxin Linked to a Tumor Antigen." Cancer Research 61: 3698-3703 (2001).

Hung, C-F. et al., "Control of mesothelin-expressing ovarian cancer using adoptive transfer of mesothelin peptide-specific CD8+T cells." Gene Therapy, pp. 1-9 (2007).

Hung et al., "Control of mesothelin-expressing ovarian cancer using adoptive transfer of mesothelin peptide-specific CD8+T cells," Gene Therapy, 14(12):921-929 (2007).

Hung, C-F. et al., "DNA Vaccines Encoding li-PADRE Generates Potent Padre-specific CD4+T-Cell Immune Responses and Enhances Vaccine Potency." Mol. Ther. Jun;15(6):1211-1219 (2007).

Hung, C-F. et al., "Enhancement of DNA Vaccine Potency by Linkage of Antigen Gene to a Gene Encoding the Extracellular Domain of Fms-like Tyrosine Kinase 3-Ligand." Cancer Research 61:1080-1088, (2001).

Hung, C-F. et al., "Enhancing Major Histocompatibility Complex Class I Antigen Presentation by Targeting Antigen to Centrosomes," Cancer Research. 63: 2393-2398, (2003).

Hung, C-F., et al., "Improving DNA Vaccine Potency by Linking Marek's Disease Virus Type 1 VP22 to an Antigen," Journal Of Virology, 76(6):2676-2682 (2002).

Hung et al., "Improving vaccine potency through intercellular spreading and enhanced MHC class I presentation of antigen," J. Immunology, 166(9):5733-5740 (2001).

Hung, C-F. et al., "Improving DNA vaccine potency via modification of professional antigen presenting cells." Current Opinion in Molecular Therapeutics, 5(1):20-24 (2003).

Hung, C-F. et al., "Modifying professional antigen-presenting cells to enhance DNA vaccine potency," Methods in Molecular Medicine, 127:199-220 (2006).

Hung et al., "Vaccinia virus preferentially infects and controls human and murine ovarian tumors in mice," Gene Therapy, 14:20-29 (2007).

Hunt et al., "Characterization and sequence of a mouse hsp70 gene and its expression in mouse cell lines," Gene, 87(2):199-204 (1990).

Hunt et al., "Conserved features of eurkaryotic hsp70 genes revealed by comparison with the nucleotide sequence of human hsp70," Proc. Natl. Acad. Sci. USA, 82:6455-6459 (1985).

Indraccolo et al., "Generation of expression plasmids for angiostatin, endostatin and TIMP-2 for cancer gene therapy," Int. J. Biological Markers, 14(4):251-256 (1999) (Abstract).

Jaffee et al., "Novel allogeneic granulocyte-macrophage colony-stimulating factor-secreting tumor vaccine for pancreatic cancer: a phase I trial of safety and immune activation," J. Clin. Oncol., 19(1):145-156 (2001).

Jager et al., "Simultaneous Humoral and Cellular Immune Response against Cancer-Testis Antigen NY-ESO-1: Definition of Human Histocompatibility Leukocyte Antigen (HLA)-A2-binding Peptide Epitopes," J. Exp. Med., 187:265-270 (1998).

Jenkins et al., "Bioluminescent Imaging (BLI) to Improve and Refine Traditional Murine Models of Tumor Growth and Metastasis," Clin. Exp. Metastatis, 20(8):733-744 (2003).

Ji, H et al., "Antigen-Specific Immunotherapy for Murine lung Metastatic Tumors Expressing Human Papillomavirus Type 16 E7 Oncoprotein." Int. J. Cancer: 78, 41-45 (1998).

Ji, H et al., "Targeting Human Papillomavirus Type 16 E7 to the Endosomal/Lysosomal Compartment Enhances the Antitumor Immunity of DNA Vaccines against Murine Human Papillomavirus Type 16 E7-Expressing Tumors," Human Gene Therapy 10:2727-2740 (1999).

Jinno et al., "Domain II Mutants of Pseudomonas Exotoxin Deficient in Translocation," J. Biol. Chem., 264(7):15953-15959 (1989).

Kadkol, S. et al., Chapter 5: In Situ Hybridization in Cancer and Normal Tissue. Methods in Molecular Biology, vol. 223: Tumor Suppressor Genes, vol. II, Edited by W. Ei-Deiry, Humana Press Inc., Totowa, NJ. (2003).

Kang, T. et al., "Enhancing dendritic cell vaccine potency by combining a BAL/BAX siRNA-mediated antiapoptotic strategy to prolong dendritic cell life with an intracellular strategy to target antigen to lysosomal compartments." Int. J. Cancer, 120:1696-1703 (2007).

Kerbel, Robert S., "Tumor angiogenesis: past, present and the near future," Carcinogenesis 21(3):505-515 (2000).

Kim et al., "Co-transfection with cDNA encoding the Bcl family of anti-apoptotic proteins improves the efficiency of transfection in primary fetal neural stem cells," J. Neuroscience Methods, 117(2):153-158 (2002).

Kim, J. et al., "Comparison of HPV DNA vaccines employing intracellular targeting strategies." Gene Therapy, 11:1011-1018 (2004).

Kim, T. et al. "Modification of Professional Antigen-Presenting Cells with Small Interfering RNA In vivo to Enhance Cancer Vaccine Potency." Cancer Res. 65(1):309-316. 2005.

Kim, T. et al., "DNA Vaccines Employing Intracellular Targeting Strategies and a Strategy to Prolong Dendritic Cell Life Generate a Higher No. Of CD8+Memory T Cells and Better Long-Term Antitumor Effects Compared with a DNA Prime-Vaccinia Boost Regimin." Human Gene Therapy 16:26-34 (2005).

Kim, T. et al., "Enhancement of DNA Vaccine Potency by Coadministration of a Tumor Antigen Gene and DNA Encoding Serine Protease Inhibitor-6." Cancer Research. 64:400-405 (2004).

Kim, T. et al., Enhancing DNA vaccine potency by coadministration of DNA encoding antiapoptotic proteins. J. Clin. Invest. 112:109-117 (2003).

Kim, D. et al., "Monitoring the Trafficking of Adoptively Transferred Antigen-Specific CD8-Positive T Cells In Vivo, Using Noninvasive Luminescence Imaging." Human Gene Therapy. 18: 1-14 (2007).

Kim, T. et al., "A DNA Vaccine Co-Expressing Antigen and an Anti-Apoptotic Molecule Further Enhances the Antigen-Specific CD8+T-Cell Immune Response." J. Biomed. Sci. 11:493-499 (2004).

Kim, T. et al., "Enhancement of suicidal DNA vaccine potency by delaying suicidal DNA-induced cell death." Gene Therapy. 11:336-342. (2004).

Kim, T. et al., "Enhancing DNA Vaccine Potency by Combining a Strategy to Prolong Dendritic Cell Life with Intracellular Targeting Strategies." The Journal of Immunology, 171:2970-2976, (2003).

Kim, T. et al., "Generation and Characterization of DNA Vaccines Targeting the Nucleocapsid Protein of Severe Acute Respiratory Syndrome Caronavirus." Journal of Virology, 78(9):4638-4645. (2004).

Kim, T. et al., "Vaccination with a DNA Vaccine Encoding Herpes Simplex Type 1 VP22 Linked to Antigen Generates Long-Term Antigen-Specific CD8-Positive memory T Cells and Protective Immunity." Human Gene Therapy. 15:167-177. (2004).

Konen-Waisman et al., "Self and Foreign 60-Kilodalton Heat Shock Protein T Cell Epitope Peptides Serve As Immunogenic Carriers for a T Cell-Independent Sugar Antigen," J. Immunology, 154:5977-5985 (1995).

Konishi et al., "Japanese encephalitis DNA vaccine candidates expressing premembrane and envelope genes induce virus-specific memory B cells and long-lasting antibodies in swine," Virology, 268(1):49-55 (2000).

Lafond-Walker, A. et al., "Inducible Nitric Oxide Synthase Expression in Coronary Arteries of Transplanted Human Hearts with Accelerated Graft Arteriosclerosis." American Journal of Pathology, 151(4): 919-925 (1997).

Lazar et al., "Transforming Growth Factor α: Mutation of Aspartic Acid 47 and Leucine 48 Results in Different Biological Activities," Mol. Cell Biol., 8(3):1247-1252 (1988).

Leitner et al., "DNA and RNA-Based Vaccines: Principles, Progress and Prospects," Vaccine 18(9-10):765-777 (1999).

Lemon et al., "Subcutaneous administration of inactivated hepatitis B vaccine by automatic jet injection," J. Med. Virol., 12(2):129-136 (1983).

Li et al., "Roles of heat-shock proteins in antigen presentation and cross-presentation," Curr. Opin. Immunol., 14(1):45-51 (2002).

Liaw, K. et al., "Human papillomavirus and cervical neoplasia: a case-control study in Taiwan." Int. J. Cancer. 62(5):565-71 (1995).

Lin, C-T. et al., "Boosting with Recombinant Vaccinia Increases HPV-16 E7-Specific T Cell Precursor Frequencies and Antitumor Effects of HPV-16 E7-Expressing Sindbis Virus Replicon Particles." Molecular Therapy. 8(4):559-566 (2003).

Lin, K.Y. et al., "Coinfection of HPV-11 and HPV-16 in a case of Laryngeal Squamous Papillomas With severe Dysplasia." Laryngoscope. 107(7):942-947 (1997).

Lin, K-Y. et al., "Ectopic Expression of Vascular Cell Adhesion Molecule-1 as a New Mechanism for Tumor Immune Evasion." Cancer. Res. 67(4) 1832-1841 (2007).

Lin, Y-Y. et al., "Vaccines against human papillomavirus." Frontiers in Bioscience. 12:246-264 (2007).

Ling, M. et al., "Preventive and Therapeutic Vaccines for Human Papillomavirus-Associated Cervical Cancers." J Biomed Sci 7:341-356 (2000).

Liu et al., "Recombinant Adeno-Associated Virus Expressing Human Papillomavirus Type 16 E7 Peptide DNA Fused with Heat Shock Protein DNA as a Potential Vaccine for Cervical Cancer," Journal of Virology, 2888-2894 (2000).

Liu et al., "The emerging role of IL-15 in NK-cell development," Immunology Today, 21(3):113-116 (2000).

Luke et al., "An OspA-based DNA vaccine protects mice against infection with Borrelia burgdorferi," J. Infect. Dis., 175(1):91-97 (1997).

Maki et al., "Human homologue of murine tumor rejection antigen pg96: 5'-Regulatory and coding regions and relationship to stress-induced proteins," Proc. Natl. Acad. Sci. USA, 87:5658-5662 (1990).

Mao, C-P. et al. "Immunotherapeutic strategies employing RNA interference technology for the control of cancers." Journal of Biomedical Science 14:15-29 (2007).

Mao, C-P. et al., "Immunological research using RNA interference technology." Immunology, 121:295-307 (2007).

Massa et al., "Enhanced Efficacy of Tumor Cell Vaccines Transfected with Secretable hsp70," Cancer Research, 64:1502-1508 (2004).

McCluskie et al., "Route and Method of Delivery of DNA Vaccine Influence Immune Responses in Mice and Non-Human Primates," Mol. Med. 5:287-300 (1999).

Meinkoth et al., "Hybridization of nucleic acids immobilized on solid supports," Anal. Biochem., 138(2):267-284 (1984).
Meneguzzi et al., "Immunization against Human Papillomavirus Type 16 Tumor Cells with Recombinant Vaccinia Viruses Expressing E6 and E7," Virology, 181:62-69 (1991).
MHC Class-I Binding Peptide Prediction Results for the Maltose Binding Protein of Vector pMAL used in D8, using ProPred-I (http://www.imtech.res.in/raghava/propred1/) (2007).
Michel, N. et al.; "Improved Immunogenicity of Human Papillomavirus Type 16 E7 DNA After Fusion to the Herpes Simplex Virus 1 VP22 Gene"; Barcelona, Spain, Jul. 23-28, 2000, Abstract, 458, XP002201712.
Michel, N., et al.; "Enhanced Immunogenicity of HPV 16 E7 Fusion Proteins in DNA Vaccination" Virology, 294:47-59, XP002201708 (2002).
Mikayama et al., "Molecular cloning and functional expression of a cDNA encoding glycosylation-inhibiting factor," PNAS, 90:10056-10060 (1993).
Mold, D. et al., "Four Classes of HERV-K Long Terminal Repeats and Their Relative Promoter Strengths for Transcription." J Biomed Sci 4:78-82 (1997).
Molinari and Helenius, "Chaperone Selection During Glycoprotein Translocation into the Endoplasmic Reticulum," Science, 288(5464):331 (2000).
Moniz, M. et al., "HPV DNA Vaccines," Frontiers in Bioscience 8, d55-68, (2003).
More et al., "Activation of cytotoxic T cells in vitro by recombinant gp96 fusion proteins irrespective of the 'fused' antigenic peptide sequence," Immunol. Lett., 69(2):275-282 (1999).
Nair et al.,"Calreticulin Displays in Vivo Peptide-Binding Activity and Can Elicit CTL Responses Against Bound Peptides," Journal of Immunology 162(11):6426-5432 (1999).
Nakano et al., "Immunization with Plasmid DNA Encoding Hepatitis C Virus Envelope E2 Antigenic Domains Induces Antibodies Whose Immune Reactivity Is Linked to the Injection Mode," Journal of Virology 71:7101-7109 (1997).
Nawrocki, S. And Mackiewicz, A., "Genetically modified tumour vaccines—where we are today," Cancer Treatment Reviews 25:29-46 (1999).
Nguyen et al., "A Mutant of Human Papillomavirus Type 16 E6 Deficient in Bindong α-Helix Partners Displays Reduced Oncogenic Potential in Vivo," Journal of Virology, 76(24):13039-13048 (2002).
Nicchitta, C.V. and Reed, R.C., "The immunological properties of endoplasmic reticulum chaperones: a conflict of interest?," Essays in Biochemistry 36:15-25 (2000).
Noessner et al., "Tumor-Derived Heat Shock Protein 70 Peptide Complexes Are Cross-Presented by Human Dendritic Cells," The Journal of Immunology, 169:5424-5432 (2002).
Ockert et al., "Advances in Cancer Immunotherapy Symposium, Dresden, Germany," Immunology Today 20(2):63-65 (1999).
Ohtsuka, K., "Cloning of a cDNA for heat-shock protein hsp40, a human homologue of bacterial DnaJ," Biochem. Biophys. Res. Commun., 197(1):235-240 (1993).
Ozols, RF., "Systemic therapy for ovarian cancer: current status and new treatments," Semin. Oncol., 33:53-11 (2006).
Pai, S I et al., "Prospects of RNA interference therapy for cancer." Gene Therapy, 13:464-477 (2006).
Pejawar-Gaddy et al., "Cancer vaccines: accomplishments and challenges," Crit. Rev. Oncol. Hematol., 67(2):93-102 (2008).
Peng et al., "Efficient delivery of DNA vaccines using human papillomavirus pseudovirions," Gene Therapy, 17(12):1453-1464 (2010).
Peng, S, et al., "A combination of DNA vaccines targeting human papillomavirus type 16 E6 and E7 generates potent antitumor effects." Gene Therapy. 13:257-265 (2006).
Peng, S. et al., "Characterization of HLA-A2-restricted HPV-16 E7-specific CD8+T-cell immune responses induced by DNA vaccines in HLA-A2 transgenic mice." Gene Therapy. 13:67-77 (2006).
Peng, S. et al., "Development of a DNA Vaccinje targeting Human Papillomavirus Type 16 Oncoprotein E6." Journal of Virology. 78(16):8468-8476. (2004).
Peng, S. et al.,"HLA-DQB1*02- restricted HPV-16 E7 Peptide-Specific CD4+T-Cell Immune Responses Correlate with Regression of HPV-16-Associated High-Grade Squamous Intraepithelial Lesions." Clin. Cancer Res. 13(8) 2479-2487 (2007).
Peng, S. et al., "Vaccination with Dendritic Cells Transgected with Bak and BAX siRNA Enhances Antigen-Specific Immune Responses by Prolonging Dendritic Cell Life." Human Gene Therapy 16:584-593 (2005).
Peng, S., et al.; "Characterization of HPV16-E6 DNA vaccines employing intracellular targeting and intercellular spreading strategies." Journal of Biomedical Science. (2005) 12:689-700.
Peoples et al., "Vaccine Implications of Folate Binding Protein, a Novel Cytotoxic T Lymphocyte-recognized Antigen System in Epithelial Cancers," Clinical Cancer Research, 5:4214-4223 (1999).
Pfisterer et al., "Management of platinum-sensitive recurrent ovarian cancer," Semin. Oncol., 33:512-516 (2006).
Ramos-Soriano, A. et al., "Enteric pathogens associated with gastrointestinal dysfunction in children with HIV infection." Molecular and Cellular Probes 10, 67-73 (1996).
Rashid, A. et al., "Mitochondrial Proteins That Regulate Apoptosis and Necrosis Are Induced in Mouse Fatty Liver." Hepatology 29:1131-1138 (1999).
Ray et al., "Apoptosis Induction in Prostate Cancer Cells and Xenografts by Combined Treatment with APO2 Ligand/Tumor Necrosis Factor-related apoptosis-inducing Ligand and CPT-11," Cancer Research, 63:4713-4723 (2003).
Roby et al., "Development of a syngeneic mouse model for events related to ovarian cancer," Carcinogenesis, 21(4):585-591 (2000).
Roden and Wu. "How will HPV vaccines affect cervical cancer?" Nature Reviews. vol. 6, pp. 753-763. (2006).
Roden, R. et al. "The impact of preventative HPV Vaccination." Discovery Medicine. vol. 6, No. 35, pp. 175-181 (2006).
Roden, R. et al., "Vaccination to Prevent and Treat Cervical Cancer." Human Pathology. 35(8): 971-982. (2004).
Rogers et al., "Multistage Multiantigen Heterologous Prime Boost Vaccine for *Plasmodium knowlesi* Malaria Provides Partial Protection in Rhesus Macaques," Infection and Immunity, 69(9):5565-5572 (2001).
Rouse et al., "Induction In Vitro of Primary Cytotoxic T-Lymphocyte Responses with DNA Encoding Herpes Simplex Virus Proteins," Journal of Virology, 68(9):5685-5689 (1994).
Sanchez-Perez et al., "Killing of Normal Melanocytes, Combined with Heat Shock Protein 70 and CD4OL Expression, Cures Large Established Melanomas," The Journal of Immunology, 177:4168-4177 (2006).
Sasaki et al., "Adjuvant formulations and delivery systems for DNA vaccines," Methods, 31(3):243-254 (2003).
Serody et al., "T Cell Activity After Dendritic Cell Vaccination Is Dependent on Both the Type of Antigen and the Mode of Delivery," J. Immunology, 164(9):4961-4967 (2000).
Schultes et al., "Monitoring of immune responses to CA125 with IFN-gamma ELISPOT assay," J. Immunol. Methods, 279:1-15 (2003).
Shalinsky et al., "Marked Antiangiogenic and Antitumor Efficacy of AG3340 in Chemoresistant Human Non-Small Cell Lung Cancer Tumors: Single Agent and Combination Chemotherapy Studies," Clincal Cancer Research 5:1905-1917 (1999).
Sheikh et al., "Guns, genes, and spleen: a coming of age for rational vaccine design," Methods, 31(3):183-192 (2003).
Sin, J.I., "Human papillomavirus vaccines for the treatment of cervical cancer," Expert Review Vaccines, 5(6):783-792 (2006).
Smahel et al., "DNA vaccine against oncogenic hamster cells transformed by HPV16 E6/E7 oncogenes and the activated *ras* oncogene," Oncology Reports, 6:211-215 (1999).
Smahel et al., "Immunisation with modified HPV16 E7 genes against mouse oncogenic TC-1 cell sublines with downregulated expression of MHC class I molecules," Vaccine, 21:1125-1136 (2003).
Srivastava et al., "5'-Structural analysis of genes encoding polymorphic antigens of chemically induced tumors," Proc. Natl. Acad. Sci. USA, 84:3807-3811 (1987).
Srivastava et al., "Evidence for Peptide-Chaperoning by the Endoplasmic Reticular Heat Shock Protein GP96: Implications for Vaccination Against Cancer and Infectious Diseases," J. Cell. Biochem. Suppl. 17D:94 (Abstract NZ 014) (1993).

Srivastava, P., "Interaction of heat shock proteins with peptides and antigen presenting cells: chaperoning of the innate and adaptive immune responses," Annu. Rev. Immunol., 20:395-425 (2002).

Szymczak et al., "Correction of multi-gene deficiency in vivo using a single 'self-cleaving' 2A peptide-based retroviral vector," Nat. Biotechnol., 22(5):589-594 (2004).

Theriault et al., "Extracellular HSP70 binding to surface receptors present on antigen presenting cells and endothelial/epithelial cells," FEBS Let ., 579(9):1951-1960 (2005).

Thomas et al., "Mesothelin-specific CD8+T Cell Responses Provide Evidence of In Vivo Cross-Priming by Antigen-Presenting Cells in Vaccinated Pancreatic Cancer Patients," J. Exp. Med., 200(3):297-306 (2004).

Thornburg et al., "Induction of Cytotoxic T Lymphocytes With Dendritic Cells Transfected With Human Papillomavirus E6 and E7 RNA: Implications for Cervical Cancer Immunotherapy," Journal of Immunotherapy, 23(4):412-418 (2000).

Ting et al., "Human gene encoding the 78,000-dalton glucose-regulated protein and its pseudogene: structure, conservation, and regulation," DNA, 7(4):275-286 (1988).

Tomson, T. et al. "Human papillomavirus vaccines for the prevention and treatment of cervical cancer." Current Opinion in Investigational Drugs, 5(12):1247-1261. (2004).

Torres et al., "Differential Dependence on Target Site Tissue for Gene Gun and Intramuscular DNA Immunizations," The Journal of Immunology 158:4529-4532 (1997).

Trimble C, et al., "Spontaneous Regression of High-Grade Cervical Dysplasia: Effects of Human Papillomavirus Type and HLA Phenotype." Clin. Cancer Res. 11(13):4717-4723 (2005).

Trimble, C. et al., "Comparison of the CD8+T cell responses and antitumor effects generated by DNA vaccine administered through gen gun, biojector and syringe." Vaccine. 21:4036-4042, (2003).

Trompeter, Hans-Ingo et al., "Variable Nuclear Cytoplasmic Distribution of the 11.5-kDa Zinc-binding Protein (Parathymosin-α) and Identification of a Bipartite Nuclear Localization Signal," The Journal of Biological Chemistry 271(2):1187-1193 (1996).

Trujillo, J. et al., "Characterization of human papillomavirus type 57b: transforming activity and comparative sequence analysis as probes for biological determinants associated with high-risk oncogenic viruses." Virus genes. 12(2):165-78 (1996).

Tsen, S-W. et al., "Enhancing Dna Vaccine Potency by Modifying the Properties of Antigen-Presenting Cells," Expert Review of Vaccines, 6(2):227-239 (2007).

Tseng et al., "Systemic tumor targeting and killing by Sindbis viral vectors," Nature Biotechnology, 22(1):70-77 (2004).

Tseng et al., "Using Sindbis Viral Vectors for Specific Detection and Suppressin of Advanced Ovarian Cancer in Animal Models," Cancer Research, 64:6684-6692 (2004).

Udono et al., "Heat Shock Protein 70-associated Peptides Elicit Specific Cancer Immunity," J. Exp. Med., 178:1391-1396 (1993).

van Bergen et al., "Superior Tumor Protection Induced by a Cellular Vaccine Carrying a Tumor-specific T Helper Epitope by Genetic Exchange of the Class II-associated Invariant Chain Peptide," Cancer Research, 60(22):6427-6433 (2000).

van Tienhoven et al., "Induction of antigen specific CD4 + T cell responses by invariant chain based DNA vaccines," Vaccine, 19:1515-1519 (2001).

Vu, K. et al., "Cellular Proliferation, Estrogen Receptor, Progesterone Receptor, and bcl-2 Expression in GnRH Agonist-Treated Uterine Leiomyomas." Human Pathology 29:359-363 (1998).

Wang et al., "A Single Amino Acid Determines Lysophospholipid Specificity of the $S1P_1(EDG1)$ and $LPA_1$ (EDG2) Phospholipid Growth Factor Receptors," The Journal of Biological Chemistry, 276(52):49213-49220 (2001).

Wang et al., "CD40 Is a Cellular Receptor Mediating Mycobacterial Heat Shock Protein 70 Stimulation of CC-Chemokines," Immunity, 15:971-983 (2001).

Wang, T-L. et al., "Intramuscular administration of E7-transfected dendritic cells generates the most potent E7-specific anti-tumor immunity." Gene Therapy 7:726-733 (2000).

Whisstock et al., "Prediction of protein function from protein sequence and structure," Quarterly Reviews of Biophysics, 3:307-340 (2003).

Whittall et al., "Interaction between the CCR5 chemokine receptors and microbial HSP70," Eur. J. Immunol., 36(9):2304-2314 (2006).

Wu, T.C., "Therapeutic human papillomavirus DNA vaccination strategies to control cervical cancer," Eur. J. Immunol., 37(2):310-314 (2007).

Wu, T-C, et al., "Engineering an intracellular pathway for major histocompatibility complex class II presentation of antigens." Proc. Natl. Acad. Sci. 92:11671-11675 (1995).

Wu, T-C. et al., "A Reassessment of the Role of B7-1 Expression in Tumor Rejection." J. Exp. Med. 182:1415-1421 (1995).

Wu, T-C. et al., "Demonstration of human papillomavirus (HPV) genomic amplification and viral-like particles from CaSki cell line in SCID mice." Journal of Virological Methods 65:287-298 (1997).

Wu, T-C. et al., "Detection of the Human Cytomegalovirus 2.0-kb Immediate Early Gene I Transcripts in Permissive and Nonpermissive Infections by RNA in situ Hybridization." J Biomed Sci 4:19-27 (1997).

Yen, M. et al., "Diffuse Mesothelin Expression Correlates with Prolonged Patient Survival in Ovarian Serous Carcinoma." Clin. Cancer. Res. 12(3) 827-831 (2006).

Yokokawa et al., "Identification of Novel Human CTL Epitopes and Their Agonist Epitopes of Mesotheliin," Clin. Cancer Res., 11(17):6342-6351 (2005).

International Search Report dated Oct. 15, 2001 from PCT/US2000/41422.

International Search Report dated Nov. 13, 2007 from PCT/US2003/10235.

International Search Report dated Dec. 3, 2002 from PCT/US2001/24134.

International Search Report dated Sep. 20, 2002 from PCT/US2002/02598.

International Search Report dated Jun. 28, 2002 from PCT/US2001/23966.

International Search Report dated Mar. 25, 2005 from PCT/US2004/05292.

International Search Report dated Apr. 1, 2005 from PCT/US2004/13756.

International Search Report dated Jul. 7, 2008 from PCT/US2005/47200.

International Search Report dated Mar. 22, 2007 from PCT/US2006/02707.

International Search Report dated Aug. 13, 2008 from PCT/US2007/76525.

Supplementary EP Search Report dated Mar. 6, 2006 from EP 02707618.

Supplementary EP Search Report dated Sep. 28, 2006 from EP 04751244.

Supplementary EP Search Report dated May 30, 2008 from EP 06 73 3904.

Koch et al., "Hijacking a chaperone: manipulation of the MHC class II presentation pathway," Immunology Today, 21(11):546-550 (2000).

van der Burg et al., "Pre-clinical safety and efficacy of TA-CIN, a recombinant HPV16 L2E6E7 fusion protein vaccine, in homologous and heterologus prime-boost regimens," Vaccine, 19:3652-3660 (2001).

* cited by examiner

SUPERIOR MOLECULAR VACCINE LINKING THE TRANSLOCATION DOMAIN OF A BACTERIAL TOXIN TO AN ANTIGEN

CROSS-REFERENCE TO RELATED APPLICATIONS

This application is a continuation in part of co-pending, commonly assigned patent applications PCT/US00/41422 filed 20 Oct. 2000 and U.S. Ser. No. 09/501,097, filed 9 Feb. 2000 now U.S. Pat. No. 6,734,173, both of which were continuations-in-part of U.S. Ser. No. 09/421,608, filed 20 Oct. 1999 (now abandoned). This application also claims priority to provisional application U.S. Ser. No. 60/281,003, filed 4 Apr. 2001. All of the above applications are incorporated by reference in their entirety.

STATEMENT OF RIGHTS TO INVENTIONS MADE UNDER FEDERALLY SPONSORED RESEARCH

This invention was made in part with federal government support under National Institutes of Health grants NIH 5 PO1 34582-01, U19 CA72108-02, RO01 CA72631-01, which provides to the United States rights in this invention.

BACKGROUND OF THE INVENTION

1. Field of the Invention

The present invention in the fields of molecular biology, immunology and medicine relates to a chimeric nucleic acid, preferably DNA, encoding a fusion protein and its use as a vaccine to enhance immune responses, primarily cytotoxic T lymphocyte (CTL) responses to specific antigens such as tumor or viral antigens. The fusion protein comprises an antigenic polypeptide fused to a bacterial toxin translocation protein that promotes processing via the MHC class I pathway and selective induction of immunity mediated by CD8$^+$ antigen-specific CTL.

2. Description of the Background Art

Cytotoxic T lymphocytes (CTL) are critical effectors of antitumor responses (reviewed in Refs 1-3). Activated CTL are effector cells that mediate antitumor immunity by direct lysis of their target tumor cells or by releasing of cytokines that orchestrate immune and inflammatory responses that interfere with tumor growth or metastasis. Depletion of CD8$^+$ CTL leads to the loss of antitumor effects of several cancer vaccines (4, 5). Therefore, the enhancement of antigen presentation through the MHC class I pathway to CD8$^+$ T cells has been a primary focus of cancer immunotherapy.

Naked DNA vaccines have emerged recently as attractive approaches for vaccine development (reviewed in 6-11). DNA vaccines generated long-term cell-mediated immunity (reviewed in 12). In addition, DNA vaccines can generate CD8$^+$ T cell responses in vaccinated humans (13). However, one limitation of these vaccines is their lack of potency, since the DNA vaccine vectors generally do not have the intrinsic ability to be amplified and to spread in vivo as do some replicating viral vaccine vectors. Furthermore, some tumor antigens such as human papillomavirus-16 (HPV-16) E7 (5) are weak immunogens. Therefore, there is a need in the art for strategies to enhance DNA vaccine potency, particularly for more effective cancer immunotherapy.

The present inventors and their colleagues recently demonstrated that linkage of HPV-16 E7 antigen to Mtb heat shock protein 70 (Hsp70) leads to the enhancement of DNA vaccine potency (5). (See also U.S. Ser. No. 09/501,097, filed 9 Feb. 2000; and U.S. Ser. No. 099/421,608, filed 20 Oct. 1999, from which the present application claims priority) Immunization with HSP complexes isolated from tumor or virus-infected cells induced potent anti-tumor immunity (Janetzki, S et al., 1998. *J Immunother* 21:269-76) or antiviral immunity (Heikema, A E et al., *Immunol Lett* 57:69-74). In addition, immunogenic HSP-peptide complexes could be reconstituted in vitro by mixing the peptides with HSPs (Ciupitu, A M et al., 1998. *J Exp Med* 187:685-91). Furthermore, HSP-based protein vaccines have been created by fusing antigens to HSPs (Suzue, K et al., 1996. *J Immunol* 156:873-9). The results of these investigations point to HSPs a attractive candidates for use in immunotherapy. However, prior to the present inventors' work, HSP vaccines were all peptide/protein-based vaccines or, in more recent cases, were in the form of naked DNA. To date, there have been no reports of HSPs incorporated into self-replicating RNA vaccines.

DOCUMENTS CITED ABOVE

1. Chen, C H et al., J Biomed Sci. 5: 231-252, 1998
2. Pardoll, D M. Nat Med. 4: 525-531, 1998
3. Wang, R F et al., Immunol Rev. 170: 85-100, 1999
4. Lin, K-Y et al., Canc Res. 56: 21-26, 1996
5. Chen, C-H et al., Canc Res. 60: 1035-42, 2000
6. Hoffman, S L et al., Ann N Y Acad Sci. 772: 88-94, 1995
7. Robinson, H L. Vaccine. 15: 785-787, 1997
8. Donnelly, J J et al., Annu Rev Immunol. 15: 617-648, 1997
9. Klinman, D M et al., Immunity. 11: 123-129, 1999
10. Restifo, N P et al., Gene Ther. 7: 89-92, 2000
11. Gurunathan, S et al., Annu Rev Immunol. 18: 927-974, 2000
12. Gurunathan, S et al., Curr Opin Immunol. 12: 442-447, 2000
13. Wang, R et al. Science. 282: 476-480, 1998.

SUMMARY OF THE INVENTION

The growing understanding of the antigen presentation pathway creates the potential for designing novel strategies to enhance vaccine potency. One strategy taken by the present inventors in the present invention to enhance the presentation of antigen through the MHC class I pathway to CD8$^+$ T cells is the exploitation of the translocation features of certain bacterial toxins such as *Pseudomonas aeruginosa* exotoxin A (ETA) (reviewed in Goletz, T J et al., Hum Immunol. 54: 129-136, 1997). ETA is one of several secreted bacterial toxins that can covalently modify particular proteins in mammalian cells through the toxin's translocation. Molecular characterization of ETA has revealed three functional domains (Hwang, J et al., Cell. 48: 129-136, 1987). Domain I is responsible for binding to a cell surface receptor (Guidi-Rontani, et al., Mol Microbiol. 1: 67-72, 1987). Domain II is responsible for translocation to the cytosol (Jinno, Y et al., J Biol Chem. 264: 15953-15959, 1989; Siegall, C B et al., Biochemistry. 30: 7154-7159, 1991; Prior, T I et al., Biochemistry. 31: 3555-3559, 1992). Domain III is responsible for the toxic activity by binding to ADP-ribosyl transferase (Chaudhary, V K et al., Proc Natl Acad Sci USA. 87: 308-312, 1990). In particular, domain II (dII) of ETA (abbreviated ETA(dII)) has been used to engineer a chimeric multidomain protein to deliver DNA into the cytosol (Fominaya, J et al., J Biol Chem. 271: 10560-10568, 1996; Fominaya, J et al., Gene Ther. 5: 521-530, 1998). This capacity to facilitate translocation from extracellular and vesicular compartments into the cytoplasm represents an opportunity to enhance class I presentation of exogenous antigen to CD8$^+$ T cells.

The present inventors created a novel fusion of the translocation domain (domain II) of *Pseudomonas aeruginosa* exotoxin A (ETA(dII)) with a model tumor antigen, human papillomavirus type 16 (HPV-16) E7, in the context of a DNA vaccine. In in vitro studies, the inventors showed that cells transfected with ETA(dII)/E7 DNA or dendritic cells (DCs) pulsed with lysates containing ETA(dII)/E7 protein exhibited enhanced major histocompatibility (MHC) class I presentation of E7 antigen. Vaccination of mice with ETA(dII)/E7 DNA generated a dramatic increase in the number of E7-specific CD8+ T cell precursors (approximately 30-fold compared to wild-type E7 DNA) and converted a less effective DNA vaccine into one with significant potency against HPV-16 E7-expressing murine tumors via a CD8-dependent pathway. These results indicate that fusion of the translocation domain of a bacterial toxin to an antigen may greatly enhance vaccine potency.

Thus the present invention is directed to a nucleic acid encoding a chimeric or fusion polypeptide which polypeptide comprises:
(a) a first domain comprising a translocation polypeptide; and
(b) a second domain comprising at least one antigenic peptide.

In the above nucleic acid, the translocation polypeptide is preferably a bacterial toxin translocation polypeptide, more preferably domain II of *Pseudomonas aeruginosa* exotoxin A (ETA(dII)).

The above nucleic acid is preferably SEQ ID NO:3 or a homologue thereof.

The above nucleic preferably comprises a nucleotide sequence that encodes a translocation polypeptide which sequence is included in SEQ ID NO:1.

In the above nucleic acids, the antigenic peptide preferably comprises an epitope that binds to and is presented on the cell surface by MHC class I proteins. The epitope is preferably between about 8 and about 11 amino acid residues in length.

Preferably the antigen (i) is derived from a pathogen selected from the group consisting of a mammalian cell, a microorganism or a virus; or (ii) cross-reacts with an antigen of the pathogen. The virus may be a human papilloma virus and the antigen is preferably the HPV-16 E7 peptide. It is preferred that HPV-16 E7 polypeptide not be oncogenic.

The pathogen may be a bacterium.

In another embodiment, the antigen is a tumor-specific or tumor-associated antigen.

The above nucleic acid may be operatively linked to a promoter, preferably one which is expressed in an antigen presenting cell (APC), more preferably in a dendritic cell.

The present invention also provides an expression vector comprising any of the above nucleic acid molecules, operatively linked to a promoter and, optionally, to one or more regulatory elements that enhance expression of the nucleic acid in a cell.

The above expression vector may be a viral vector or a plasmid, including a self-replicating RNA replicon.

In the above expression vector, the translocation polypeptide is preferably ETA(dII).

Also provided is a particle comprising the above nucleic acid or expression vector. The particle preferably comprises a material, such as gold, that is suitable for introduction into a cell or an animals by particle bombardment.

The present invention is also directed to a cell which has been modified to comprise the above nucleic acid or the above the expression vector, and which cell expresses the nucleic acid. Preferably, the cell is an APC, such as a dendritic cell, a keratinocyte, a macrophage, a monocyte, a B lymphocyte, a microglial cell, an astrocyte, or an activated endothelial cell.

Also provided is a chimeric polypeptide comprising
(a) a first domain comprising a translocation polypeptide; and
(b) a second domain comprising at least one antigenic peptide.

The translocation polypeptide is preferably a bacterial toxin translocation polypeptide, more preferably, ETA(dII). Preferably, the translocation polypeptide comprises SEQ ID NO:3 or a homologue thereof.

The above chimeric polypeptide is preferably encoded by a nucleic acid as described above.

Preferably, in the chimeric polypeptide, the antigenic peptide comprises an epitope that binds to and is presented on the cell surface by MHC class I proteins.

In the above chimeric peptide, the translocation domain and the antigenic peptide may be linked by a chemical linker.

Preferably, the chimeric polypeptide above is a fusion polypeptide.

The first domain may be either N-terminal or C-terminal to the second domain.

The present invention is also directed to a pharmaceutical composition capable of inducing or enhancing an antigen specific immune response, comprising a pharmaceutically acceptable carrier or excipient and any one or more of:
(a) the above nucleic acid;
(b) the above expression vector;
(c) the above particle
(d) the above cell; or
(e) the above chimeric polypeptide.

In another embodiment, the invention is directed to a method of enhancing an antigen specific immune response comprising administering an effective amount of a composition comprising
(a) the above nucleic acid;
(b) the above expression vector;
(c) the above particle
(d) the above cell; or
(e) the above chimeric polypeptide.
thereby inducing or enhancing the antigen specific immune response.

In the above method, the antigen specific immune response is preferably mediated at least in part by CD8+ cytotoxic T lymphocytes (CTL).

In the above methods, the composition may be administered ex vivo, for example, o APCs, preferably human APCs, such as ones from a live subject. Preferred APCs are DCs. This method may further comprise administering the ex vivo-treated APCs to a histocompatible subject.

In another embodiment of the above methods, the composition is administered in vivo, preferably to a human. Preferred routes of administration are intramuscularly, intradermally, or subcutaneously. In administering the composition to a subject with a tumor, the route may be intratumoral or peritumoral.

Also provided is a method of increasing the numbers of CD8+ CTLs specific for a selected desired antigen in a subject comprising administering an effective amount of a composition comprising
(a) the above nucleic acid;
(b) the above expression vector;
(c) the above particle
(d) the above cell; or
(e) the above chimeric polypeptide.
wherein the antigenic peptide comprises an epitope that binds to and is presented on the cell surface by MHC class I proteins, thereby increasing the numbers of antigen-specific CD8+ CTLs.

In another embodiment, the invention provides a method of inhibiting the growth of a tumor in a subject comprising administering an effective amount of a composition comprising
(a) the above nucleic acid;
(b) the above expression vector;
(c) the above particle
(d) the above cell; or
(e) the above chimeric polypeptide.
thereby inhibiting growth of the tumor. In this method the administering may be intratumoral or peritumoral.

BRIEF DESCRIPTION OF THE DRAWINGS

(FIG. 1A) Schematic diagram showing the constructs of full-length ETA and the chimeric ETA(dII)/E7 gene. The DNA fragment encoding ETA(dII) (aa 247-416) is depicted in the spotted box. The fragment encoding HPV-16 E7 (aa 1-96) is depicted in the white box. FIG. 1B: Western blot analysis to characterize the expression of E7/GFP protein in cells transfected with E7/GFP or ETA(dII)/E7/GFP DNA. Lane 1, lysates from cells transfected with E7/GFP DNA; Lane 2, lysates from cells transfected with ETA(dII)/E7/GFP DNA; Lane 3, concentrated culture medium from cells transfected with E7/GFP DNA; Lane 4, concentrated culture medium from cells transfected with ETA(dII)/E7/GFP DNA; Lane 5, lysates from nontransfected 293 D b, K b cells as a negative control. Note: lysates from E7/GFP DNA-transfected 293 $D^b K^b$ cells revealed a protein band with a size of approximately Mr 30,000 corresponding to E7/GFP protein in Lane 1, as indicated by the short arrow. Meanwhile, lysates from ETA(dII)/E7/GFP DNA-transfected 293 $D^b K^b$ cells generated a protein band with a size of approximately Mr 56,000 corresponding to ETA(dII)/E7/GFP protein in Lane 2, as indicated by the long arrow. E7/GFP DNA-transfected cells exhibited levels of protein expression comparable with that of ETA(dII)/E7/GFP DNA-transfected cells.

(FIG. 2A) CTL assays to demonstrate enhanced presentation of E7 through the MHC class I pathway of cells transfected with ETA(dII)/E7 DNA. 293 $D^b K^b$ cells transfected with various DNA constructs served as target cells. These Various E/T ratios were used, with $D^b$-restricted E7-specific CD8$^+$ effector T cells. (FIG. 2B) CTL assays demonstrate enhanced MHC class I presentation of E7 in bone marrow-derived DCs pulsed with cell lysates containing chimeric ETA(dII)/E7 protein. Bone marrow-derived DCs were pulsed with cell lysates from various DNA-transfected 293 $D^b K^b$ cells at different concentrations as described in Example I. These assays were performed at a fixed E:T ratio (9/1) using $D^b$-restricted E7-specific CD8$^+$ effector T cells.

(FIG. 3A) The number of IFN-γ-producing E7-specific CD8$^+$ T cells was determined using flow cytometry in the presence of MHC class I restricted E7 peptide (aa 49-57)(44). (FIG. 3B) The number of IFN-γ-producing E7-specific CD4$^+$ T cells was determined using flow cytometry in the presence MHC class II restricted E7 peptide (aa 30-67)(45). Results are from one representative experiment of two performed.

(FIG. 4A) In vivo tumor protection experiment. 100% of mice receiving ETA(dII)/E7 DNA vaccination remained tumor-free 60 days after TC-1 challenge. (FIG. 4B) In vivo tumor therapy experiment. The ETA(dII)/E7 group had the fewest pulmonary nodules compared to the other vaccinated groups (one-way ANOVA, p<0.001). Results are expressed as mean number of lung nodules±SEM. (FIG. 4C) In vivo antibody depletion experiments to determine the effect of lymphocyte subsets on the tumor protection of the ETA(dII)/E7 DNA vaccine. Depletion of CD4$^+$, CD8$^+$ and NK1.1$^+$ cells was initiated one week prior to tumor challenge and continued for 63 days after tumor challenge. The results are from one representative experiment of two performed.

DESCRIPTION OF THE PREFERRED EMBODIMENTS

Figure 1:
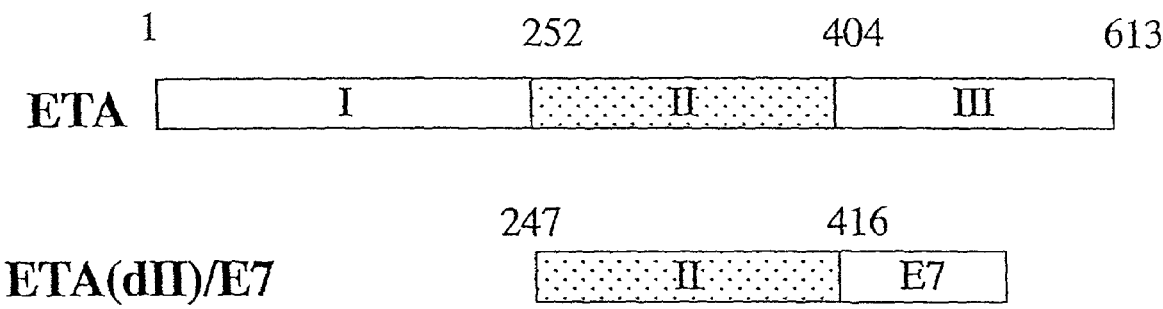
FIGS. 1A and 1B. Chimeric ETA(dII)/E7 DNA construct and characterization of E7 protein expression.
Figure 1:
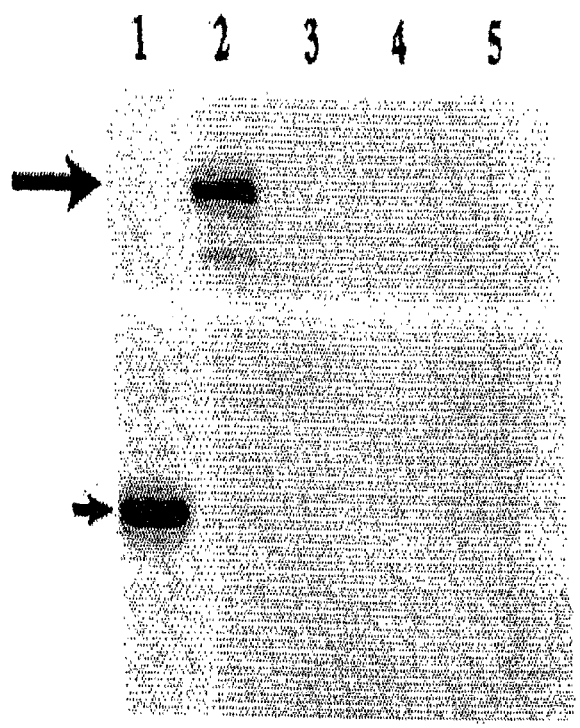

The ability of the ETA(dII) polypeptide to facilitate translocation from the endosomal/lysosomal compartments to the cytoplasm suggested to the present inventors that at it may lead to the enhancement of MHC class I presentation of exogenous antigen if physically linked to the antigen. They therefore engineered a DNA vaccine encoding ETA(dII) linked to a model antigen, which was predicted to enhance MHC class I presentation of this antigen to CD8$^+$ T cells and thereby enhance vaccine potency. The model antigen for vaccine development was the E7 protein of the human papilloma virus HPV-16 E7. E7 is important in the induction and maintenance of cellular transformation by the virus and is co-expressed in most HPV-containing cervical cancers as well as their precursor lesions (Wu, T C, Curr Opin Immunol. 6: 746-754, 1994). Therefore, vaccines targeting E7 are useful for preventing and/or and treating HPV-associated cervical malignancies.

The results presented herein indicate that vaccination with a chimeric ETA(dII)/E7 DNA vaccine enhanced MHC class I presentation of E7, leading to a dramatic increase in the number of E7-specific CD8$^+$ T cell precursors. Furthermore, the ETA(dII)/E7 DNA vaccine generated potent antitumor effects against subcutaneous E7-expressing tumors and already established E7-expressing metastatic lung tumors. These results indicate that fusion of the translocation domain of ETA to an antigen greatly enhances MHC class I presentation of the antigen. This represents a novel strategy to improve vaccine potency.

The invention provides compositions and methods for enhancing the immune responses, particularly cytotoxic T cell immune responses, induced by ex vivo or in vivo administration of chimeric polypeptides or, preferably, nucleic acid vaccines that encode these chimeric polypeptides. The preferred chimeric or fusion polypeptide comprises (1) at least one first polypeptide or peptide that, upon introduction to cells of the host immune system, in vitro or in vivo, promotes (a) processing via the MHC class I pathway and/or (b) development or activity of APCs, primarily DCs, and (2) at least one second polypeptide or peptide that is an antigenic polypeptide or peptide in the host.

As noted, in a preferred embodiment, the chimeric or fusion polypeptides are "indirectly" administered by administration of a nucleic acid that encodes the chimeric molecule; the nucleic acid construct, and thus the fusion protein, is expressed in vivo. The chimeric nucleic acids are administered in the form of DNA vaccines, either naked DNA or suicidal DNA, or a self-replicating RNA replicons.

The fusion protein comprises at least two domains or repeats thereof. A preferred embodiment of the first type of domain is a polypeptide that facilitates translocation from the endosomal/lysosomal compartments to the cytoplasm, thereby promoting processing via the MHC class I pathway.

The most preferred polypeptide is ETA(dII). Other useful translocation polypeptides may be similar pathogenic bacterial toxins from *Diptheria, Clostridium, Botulinum, Bacillus, Yersinia, Vibrio cholerae,* or *Bordetella pertussis,* or active fragments or domains of any of the foregoing polypeptides.

The second domain comprises a peptide or polypeptide, that includes one or several epitopes, derived from an antigen against which it is desired to induce an immune response, preferably a tumor antigen. In a preferred embodiment, the peptide comprises at least one MHC class I-binding peptide epitope that helps stimulate CD8+ CTLs and is recognized by such cells and their precursors.

The order in which the two (or more) component polypeptides of the fusion protein are arranged, and therefore, the order of the encoding nucleic acid fragments in the nucleic acid vector, can be altered without affecting immunogenicity of the fusion polypeptides proteins and the utility of the composition. For example, the ETA(dII)-encoding DNA sequences may be located 5' or 3' to the target antigen-encoding sequences. In one embodiment, these polypeptide-encoding nucleic acid domains are in-frame so that the DNA construct encodes a recombinant fusion polypeptide in which the antigen is located N-terminal to the ETA(dII)-derived polypeptide.

The vaccines of the present invention include, the antigenic epitope itself and a translocation polypeptide such as ETA (dII). In addition to the specific antigens and vectors employed in the Examples, the present invention is intended to encompass a vector such as naked RNA, self replicating RNA replicons and viruses including vaccinia, adenoviruses, adeno-associated virus (AAV), lentiviruses and RNA alphaviruses.

In addition to the translocation polypeptide, the vaccine construct of the present invention optionally, may also include (a) an additional antigen targeting or processing signal such as proteins that promote intercellular transport, e.g., VP22 protein from herpes simplex virus and related herpes viruses (see, for example, commonly assigned International patent application published as WO 02/09645, 7 Feb. 2002, incorporated by reference in its entirety); an endoplasmic reticulum chaperone polypeptide such as calreticulin, ER60, GRP94 or gp96, well-characterized ER chaperone polypeptide that representatives of the HSP90 family of stress-induced proteins (see, co-pending commonly assigned International patent application published as WO 02/09645, 14 Feb. 2002, incorporated by reference in its entirety; see also Argon (1999) *Semin. Cell Dev. Biol.* 10:495-505; Sastry (1999) J. Biol. Chem. 274:12023-12035; Nicchitta (1998) *Curr. Opin. Immunol.* 10:103-109; U.S. Pat. No. 5,981,706).

(b) an immunostimulatory cytokine, preferably those that target APCs, preferably DC's, such as granulocyte macrophage colony stimulating factor (GM-CSF), or active fragments or domains thereof; and (c) a costimulatory signal, such as a B7 family protein, including B7-DC (see commonly assigned U.S. patent application Ser. No. 09/794,210), B7.1, B7.2, soluble CD40, etc.).

(For description of some of the foregoing, see, for example, commonly owned International patent applications PCT/US01/23966, PCT/US01/24134, PCTUS/00/41422))

Naked DNA vaccines represent an attractive approach for generating antigen-specific immunity because of their stability and simplicity of delivery. Concerns with DNA vaccines include potential integration into the host genome, cell transformation, and limited potency. The use of DNA-based alphaviral RNA replicons ("suicidal DNA vectors"), as disclosed herein, may alleviate concerns surrounding DNA integration or cell transformation since suicidal DNA vectors eventually cause lysis of the cells they transfect.

To further improve the potency of suicidal DNA vaccines, ETA(dII) is linked to an antigen such as E7 as a model antigen, using DNA-based Semliki Forest virus (SFV) RNA vector, pSCA1. This suicidal DNA vaccine containing ETA (dII)/E7/fusion DNA produces significantly greater E7-specific T cell-mediated immune response in mice than do vaccines containing the wild type E7 DNA alone. Importantly, this fusion converts a less effective vaccine into one with significant therapeutic potency against established E7-expressing metastatic tumors. The antitumor effect is dependent upon CD8+ T cells. Thus, linkage of ETA(dII) to an antigen enhances the potency of a suicidal DNA vaccine.

In the methods of the invention, the chimeric polypeptide or nucleic acid that encodes it are employed to induce or enhance immune responses. In one embodiment, the compositions of the invention synergistically enhance immune responses and antitumor effects through both immunological and anti-angiogenic mechanisms.

The experiments described herein demonstrate that the methods of the invention can enhance a cellular immune response, particularly, tumor-destructive CTL reactivity, induced by a DNA vaccine encoding an epitope of a human pathogen. Human HPV-16 E7 was used as a model antigen for vaccine development because human papillomaviruses (HPVs), particularly HPV-16, are associated with most human cervical cancers. The oncogenic HPV protein E7 is important in the induction and maintenance of cellular transformation and co-expressed in most HPV-containing cervical cancers and their precursor lesions. Therefore, cancer vaccines, such as the compositions of the invention, that target E7 can be used to control of HPV-associated neoplasms (Wu (1994) *Curr. Opin. Immunol.* 6:746-754).

In one embodiment, the antigen (e.g., the MHC class I-binding peptide epitope) is derived from a pathogen, e.g., it comprises a peptide expressed by a pathogen. The pathogen can be a virus, such as, e.g., a papilloma virus, a herpesvirus, a retrovirus (e.g., an immunodeficiency virus, such as HIV-1), an adenovirus, and the like. The papilloma virus can be a human papilloma virus; for example, the antigen (e.g., the Class I-binding peptide) can be derived from an HPV-16 E7 polypeptide. In one embodiment, the HPV-16 E7 polypeptide is substantially non-oncogenic, i.e., it does not bind retinoblastoma polypeptide (pRB) or binds pRB with such low affinity that the HPV-16 E7 polypeptide is effectively non-oncogenic when expressed or delivered in vivo.

In alternative embodiments, the pathogen is a bacteria, such as *Bordetella pertussis; Ehrlichia chaffeensis; Staphylococcus aureus; Toxoplasma gondii; Legionella pneumophila; Brucella suis; Salmonella enterica; Mycobacterium avium; Mycobacterium tuberculosis; Listeria monocytogenes; Chlamydia trachomatis; Chlamydia pneumoniae; Rickettsia rickettsii*; or, a fungus, such as, e.g., *Paracoccidioides brasiliensis*; or other pathogen, e.g., *Plasmodium falciparum.*

In another embodiment, the MHC class I-binding peptide epitope is derived from a tumor cell. The tumor cell-derived peptide epitope can comprise a tumor associated antigen, e.g., a tumor specific antigen, such as, e.g., a HER-2/neu antigen.

In one embodiment, the isolated or recombinant nucleic acid molecule is operatively linked to a promoter, such as, e.g., a constitutive, an inducible or a tissue-specific promoter. The promoter can be expressed in any cell, including cells of the immune system, including, e.g., antigen presenting cells (APCs), e.g., in a constitutive, an inducible or a tissue-specific manner.

In alternative embodiments, the APCs are dendritic cells, keratinocytes, astrocytes, monocytes, macrophages, B lymphocytes, a microglial cell, or activated endothelial cells, and the like.

Unless defined otherwise, all technical and scientific terms used herein have the meaning commonly understood by a person skilled in the art of this invention. As used herein, the following terms have the meanings ascribed to them unless specified otherwise.

The term "antigen" or "immunogen" as used herein refers to a compound or composition comprising a peptide, polypeptide or protein which is "antigenic" or "immunogenic" when administered (or expressed in vivo by an administered nucleic acid, e.g., a DNA vaccine) in an appropriate amount (an "immunogenically effective amount"), i.e., capable of inducing, eliciting, augmenting or boosting a cellular and/or humoral immune response either alone or in combination or linked or fused to another substance (which can be administered at once or over several intervals). An immunogenic composition can comprise an antigenic peptide of at least about 5 amino acids, a peptide of 10 amino acids in length, a polypeptide fragment of 15 amino acids in length, 20 amino acids in length or longer. Smaller immunogens may require presence of a "carrier" polypeptide e.g., as a fusion protein, aggregate, conjugate or mixture, preferably linked (chemically or otherwise) to the immunogen. The immunogen can be recombinantly expressed from a vaccine vector, which can be naked DNA comprising the immunogen's coding sequence operably linked to a promoter, e.g., an expression cassette as described herein. The immunogen includes one or more antigenic determinants or epitopes which may vary in size from about 3 to about 15 amino acids.

The term "epitope" as used herein refers to an antigenic determinant or antigenic site that interacts with an antibody or a T cell receptor (TCR), e.g., the MHC class I-binding peptide compositions (or expressed products of the nucleic acid compositions of the invention) used in the methods of the invention. An "antigen" is a molecule or chemical structure that either induces an immune response or is specifically recognized or bound by the product or mediator of an immune response, such as an antibody or a CTL. The specific conformational or stereochemical "domain" to which an antibody or a TCR bind is an "antigenic determinant" or "epitope." TCRs bind to peptide epitopes which are physically associated with a third molecule, a major histocompatibility complex (MHC) class I or class II protein.

The term "recombinant" refers to (1) a nucleic acid or polynucleotide synthesized or otherwise manipulated in vitro, (2) methods of using recombinant DNA technology to produce gene products in cells or other biological systems, or (3) a polypeptide encoded by a recombinant nucleic acid. For example, the ETA(dII)-encoding nucleic acid or polypeptide, the nucleic acid encoding an MHC class I-binding peptide epitope (antigen) or the peptide itself can be recombinant. "Recombinant means" includes ligation of nucleic acids having various coding regions or domains or promoter sequences from different sources into a single unit in the form of an expression cassette or vector for expression of the coding sequences in the vectors resulting in production of the encoded polypeptide.

The term "self-replicating RNA replicon" refers to a construct based on an RNA virus, such as alphavirus genome RNAs (e.g., Sindbis virus, Semliki Forest virus, etc.), that have been engineered to allow expression of heterologous RNAs and proteins. These recombinant vectors are self-replicating ("replicons") which can be introduced into cells as naked RNA or DNA, as described in detail in co-pending, commonly assigned U.S. and PCT patent applications by the present inventors, having Ser. No. 10/060,274, and PCT/US02/02598, both filed on 1 Feb. 2002, and entitled "Superior Molecular Vaccine Based on Self-Replicating RNA, Suicidal DNA or Naked DNA Vector, that Links Antigen with Polypeptide that Promotes Antigen Presentation." In one embodiment, the self-replicating RNA replicon comprises a Sindbis virus self-replicating RNA vector SINrep5, which is described in detail in U.S. Pat. No. 5,217,879.

Sequences of Polypeptides and Nucleic Acids

The section that follows lists the sequences of the ETA(dII) polypeptides alone or in fusion with E7 antigen, the nucleic acids encoding some of these peptides and nucleic acids of the vectors into which the sequences encoding these polypeptides are cloned.

The complete coding sequence for *Pseudomonas aeruginosa* exotoxin type A (ETA)-SEQ ID NO:1—GenBank Accession No. K01397, is shown below:

```
  1  ctgcagctgg tcaggccgtt tccgcaacgc ttgaagtcct ggccgatata ccggcagggc
 61  cagccatcgt tcgacgaata aagccacctc agccatgatg ccctttccat ccccagcgga
121  accccgacat ggacgccaaa gccctgctcc tcggcagcct ctgcctggcc gccccattcg
181  ccgacgcggc gacgctcgac aatgctctct ccgcctgcct cgccgccgg ctcggtgcac
241  cgcacacggc ggagggccag ttgcacctgc cactcaccct tgaggcccgg cgctccaccg
301  gcgaatgcgg ctgtacctcg gcgctggtgc gatatcggct gctggccagg ggcgccagcg
361  ccgacagcct cgtgcttcaa gagggctgct cgatagtcgc caggacacgc cgcgcacgct
421  gaccctggcg gcggacgccg gcttggcgag cggccgcgaa ctggtcgtca ccctgggttg
481  tcaggcgcct gactgacagg ccgggctgcc accaccaggc cgagatggac gccctgcatg
541  tatcctccga tcggcaagcc tcccgttcgc acattcacca ctctgcaatc cagttcataa
601  atcccataaa agccctcttc cgctccccgc cagcctcccc gcatcccgca ccctagacgc
661  cccgccgctc tccgccggct cgcccgacaa gaaaaaccaa ccgctcgatc agcctcatcc
721  ttcacccatc acaggagcca tcgcgatgca cctgataccc cattggatcc ccctggtcgc
781  cagcctcggc ctgctcgccg gcggctcgtc cgcgtccgcc gccgaggaag ccttcgacct
```

-continued

```
 841 ctggaacgaa tgcgccaaag cctgcgtgct cgacctcaag gacggcgtgc gttccagccg 901 catgagcgtc gacccggcoa tcgccgacac caacggccag ggcgtgctgc actactccat 961 ggtcctggag ggcggcaacg acgcgctcaa gctggccatc gacaacgccc tcagcatcac 1021 cagcgacggc ctgaccatcc gcctcgaagg cggcgtcgag ccgaacaagc cggtgcgcta 1081 cagctacacg cgccaggcgc gcggcagttg gtcgctgaac tggctggtac cgatcggcca 1141 cgagaagccc tcgaacatca aggtgttcat ccacgaactg aacgccggca accagctcag 1201 ccacatgtcg ccgatctaca ccatcgagat gggcgacgag ttgctggcga agctggcgcg 1261 cgatgccacc ttcttcgtca gggcgcacga gagcaacgag atgcagccga cgctcgccat 1321 cagccatgcc ggggtcagcg tggtcatggc ccagacccag ccgcgccggg aaaagcgctg 1381 gagcgaatgg ccagcggca aggtgttgtg cctgctcgac ccgctggacg gggtctacaa 1441 ctacctcgcc cagcaacgct gcaacctcga cgatacctgg gaaggcaaga tctaccgggt 1501 gctcgccggc aacccggcga agcatgacct ggacatcaaa cccacggtca tcagtcatcg 1561 cctgcacttt cccgagggcg gcagcctggc cgcgctgacc gcgcaccagg cttgccacct 1621 gccgctggag actttcaccc gtcatcgcca gccgcgcggc tgggaacaac tggagcagtg 1681 cggctatccg gtgcagcggc tggtcgccct ctacctggcg cgcggctgt cgtggaacca 1741 ggtcgaccag gtgatccgca acgccctggc cagccccggc agcggcggcg acctgggcga 1801 agcgatccgc gagcagccgg agcaggcccg tctggccctg accctggccg ccgccgagag 1861 cgagcgcttc gtccggcagg gcaccggcaa cgacgaggcc ggcgcggcca acgccgacgt 1921 ggtgagcctg acctgcccgg tcgccgccgg tgaatgcgcg ggccggcgg acagcggcga 1981 cgccctgctg gagcgcaact atcccactgg cgcggagttc ctcggcgacg gcggcgacgt 2041 cagcttcagc acccgcggca cgcagaactg gacggtggag cggctgctcc aggcgcaccg 2101 ccaactggag gagcgcggct atgtgttcgt cggctaccac ggcaccttcc tcgaagcggc 2161 gcaaagcatc gtcttcggcg gggtgcgcgc gcgcagccag gacctcgacg cgatctggcg 2221 cggttctat atcgccggcg atccggcgct ggcctacggc tacgcccagg accaggaacc 2281 cgacgcacgc ggccggatcc gcaacggtgc cctgctgcgg gtctatgtgc cgcgctcgag 2341 cctgccgggc ttctaccgca ccagcctgac cctggccgcg ccggaggcgg cgggcgaggt 2401 cgaacggctg atcgccatc cgctgccgct gcgcctggac gccatcaccg ccccgaggc 2461 ggaaggcggg cgcctggaga ccattctcgg ctggccgctg gccgagcgca ccgtggtgat 2521 tccctcggcg atccccaccg acccgcgcaa cgtcggcggc gacctcgacc cgtccagcat 2581 ccccgacaag gaacaggcga tcagcgccct gccggactac gccagccagc ccggcaaacc 2641 gccgcgcgag gacctgaagt aactgccgcg accggccggc tcccttcgca ggagccgcc 2701 ttctcggggc ctggccatac atcaggtttt cctgatgcca gcccaatcga atatgaattc 2760
```

The amino acid sequence of ETA (SEQ ID NO:2), GenBank
Accession No. K01397, is shown below

```
MHLIPHWIPL VASLGLLAGG SSASAAEEAF DLWNECAKAC VLDLKDGVRS SRMSVDPATA  60

DTNGQGVLHY SMVLEGGNDA LKLAIDNALS ITSDGLTIRL EGGVEPNKPV RYSYTRQARG 120

SWSLNWLVPI GHEKPSNIKV FIHELNAGNQ LSHMSPIYTI EMGDELLAKL ARDATFFVRA 180

HESNEMQPTL AISHAGVSVV MAQTQPRREK RWSEWASGKV LCLLDPLDGV YNYLAQQRCN 240

LDDTWEGKIY RVLAGNPAKH DLDIKPTVIS HRLHFPEGGS LAALTAHQAC HLPLETFTRH 300
```

RQPRGWEQLE QCGYPVQRLV ALYLAARLSW NQVDQVIRNA LASPGSGGDL GEAIREQPEQ 360

ARLALTLAAA ESERFVRQGT GNDEAGAANA DVVSLTCPVA AGECAGPADS GDALLERNYP 420

TGAEFLGDGG DVSFSTRGTQ NWTVERLLQA HRQLEERGYV FVGYHGTFLE AAQSIVFGGV 480

RARSQDLDAI WRGFYIAGDP ALAYGYAQDQ EPDARGRIRN GALLRVYVPR SSLPGFYRTS 540

LTLAAPEAAG EVERLIGHPL PLRLDAITGP EEEGGRLETI LGWPLAERTV VIPSAIPTDP 600

RNVGGDLDPS STPDKEQAIS ALPDYASQPG KPPREDLK 638

Residues 1-25 (italicized) represent the signal peptide; the start of the mature polypeptide is shown as a bold/underlined A. The mature polypeptide is residues 26-638 of SEQ ID NO:2. The ETA(dII) translocation domain (underscored above) spans residues 247-417 of the mature polypeptide (corresponding to residues 272-442 of SEQ ID NO:2) and is presented below separately as SEQ ID NO:3.

RLHFPEGGSL AALTAHQACH LPLETFTRHR QPRGWEQLEQ CGYPVQRLVA LYLAARLSWN 60

QVDQVIRNAL ASPGSGGDLG EAIREQPEQA RLALTLAAAE SERFVRQGTG NDEAGAANAD 120

VVSLTCPVAA GECAGPADSG DALLERNYPT GAEFLGDGGD VSFSTRGTQN W 171

The sequences shown below (nucleotide is SEQ ID NO:4 and amino acid is SEQ ID NO:5) are the construct in which ETA(dII) is fused to the HPV-16 E7 polypeptide. The ETA (dII) sequence appears in plain font, extra codons from pcDNA3 are italicized; those between the ETA(dII) and E7 sequence are also bolded (and result in the interposition of two amino acids between ETA(dII) and E7. The E7 sequence is underscored. The E7 sequence ends in Gln.

```
1/1                                     31/11
atg cgc ctg cac ttt ccc gag ggc ggc agc ctg gcc gcg ctg acc gcg cac cag gct tgc
Met arg leu his phe pro glu gly gly ser leu ala ala leu thr ala his gln ala cys 61/21                                   91/31
cac ctg ccg ctg gag act ttc acc cgt cat cgc cag ccg cgc ggc tgg gaa caa ctg gag
his leu pro leu glu thr phe thr arg his arg gln pro arg gly trp glu gln leu glu 121/41                                  151/51
cag tgc ggc tat ccg gtg cag cgg ctg gtc gcc ctc tac ctg gcg gcg cgg ctg tcg tgg
gln cys gly tyr pro val gln arg leu val ala leu tyr leu ala ala arg leu ser trp 181/61                                  211/71
aac cag gtc gac cag gtg atc cgc aac gcc ctg gcc agc ccc ggc agc ggc ggc gac ctg
asn gln val asp gln val ile arg asn ala leu ala ser pro gly ser gly gly asp leu 241/81                                  271/91
ggc gaa gcg atc cgc gag cag ccg gag cag gcc cgt ctg gcc ctg acc ctg gcc gcc gcc
gly glu ala ile arg glu gln pro glu gln ala arg leu ala leu thr leu ala ala ala 301/101                                 331/111
gag agc gag cgc ttc gtc cgg cag ggc acc ggc aac gac gag gcc ggc gcg gcc aac gcc
glu ser glu arg phe val arg gln gly thr gly asn asp glu ala gly ala ala asn ala 361/121                                 391/131
gac gtg gtg agc ctg acc tgc ccg gtc gcc gcc ggt gaa tgc gcg ggc ccg gcg gac agc
asp val val ser leu thr cys pro val ala ala gly glu cys ala gly pro ala asp ser 421/141                                 451/151
ggc gac gcc ctg ctg gag cgc aac tat ccc act ggc gcg gag ttc ctc ggc gac ggc ggc
gly asp ala leu leu glu arg asn tyr pro thr gly ala glu phe leu gly asp gly gly 481/161                                 511/171
gac gtc agc ttc agc acc cgc ggc acg cag aac gaa ttc atg cat gga gat aca cct aca
asp val ser phe ser thr arg gly thr gln asn glu phe met his gly asp thr pro thr 541/181                                 571/191
ttg cat gaa tat atg tta gat ttg caa cca gag aca act gat ctc tac tgt tat gag caa
leu his glu tyr met leu asp leu gln pro glu thr thr asp leu tyr cys tyr glu gln 601/201                                 631/211
tta aat gac agc tca gag gag gag gat gaa ata gat ggt cca gct gga caa gca gaa ccg
leu asn asp ser ser glu glu glu asp glu ile asp gly pro ala ply gln ala glu pro
```

```
661/221                              691/231
gac aga gcc cat tac aat att gta acc ttt tgt tgc aag tgt gac tct acg ctt cgg ttg
asp arg ala his tyr asn ile val thr phe cys cys lys cys asp ser thr leu arg leu 721/241                              751/251
tgc gta caa agc aca cac gta gac att cgt act ttg gaa gac ctg tta atg ggc aca cta
cys val gln ser thr his val asp ile arg thr leu glu asp leu leu met gly thr leu 781/261                              811/271
gga att gtg tgc ccc atc tgt tct caa gga tcc gag ctc ggt acc aag ctt aag ttt aaa
gly ile val cys pro ile cys ser gln gly ser glu leu gly thr lys leu lys phe lys 841/281
ccg ctg atc agc ctc gac tgt gcc ttc tag
pro leu ile ser 2eu asp cys ala phe AMB
```

Compared to the GenBank sequence of E7 (SEQ ID NO: 6 & 7) shown below, three C-terminal amino acids have been deleted.

The HPV E7 sequence (nucleotide sequence is SEQ ID NO:6 and amino acid sequence is SEQ ID NO:7) is shown below:

```
1/1                                  31/11
atg cat gga gat aca cct aca ttg cat gaa tat atg tta gat ttg caa cca gag aca act
Met his gly asp thr pro thr leu his glu tyr met leu asp leu gln pro glu thr thr 61/21                                91/31
gat ctc tac tgt tat gag caa tta aat gac agc tca gag gag gag gat gaa ata gat ggt
asp leu tyr cys tyr glu gln leu asn asp ser ser glu glu glu asp glu ile asp gly 121/41                               151/51
cca gct gga caa gca gaa ccg gac aga gcc cat tac aat att gta acc ttt tgt tgc aag
pro ala gly gln ala glu pro asp arg ala his tyr asn ile val thr phe cys cys lys 181/61                               211/71
tgt gac tct acg ctt cgg ttg tgc gta caa agc aca cac gta gac att cgt act ttg gaa
cys asp ser thr leu arg leu cys val gln ser thr his val asp ile arg thr leu glu 241/81                               271/91
gac ctg tta atg ggc aca cta gga att gtg tgc ccc atc tgt tct cag gat aag ctt
asp leu leu met gly thr leu gly ile val cys pro ile cys ser gln asp lys leu
```

The sequence of the pcDNA3 plasmid vector (SEQ ID NO:8) is:

```
GACGGATCGG GAGATCTCCC GATCCCCTAT GGTCGACTCT CAGTACAATC TGCTCTGATG CCGCATAGTT AAGCCAGTAT CTGCTCCCTG

CTTGTGTGTT GGAGGTCGCT GAGTAGTGCG CGAGCAAAAT TTAAGCTACA ACAAGGCAAG GCTTGACCGA CAATTGCATG AAGAATCTGC

TTAGGGTTAG GCGTTTTGCG CTGCTTCGCG ATGTACGGGC CAGATATACG CGTTGACATT GATTATTGAC TAGTTATTAA TAGTAATCAA

TTACGGGGTC ATTAGTTCAT AGCCCATATA TGGAGTTCCG CGTTACATAA CTTACGGTAA ATGGCCCGCC TGGCTGACCG CCCAACGACC

CCCGCCCATT GACGTCAATA ATGACGTATG TTCCCATAGT AACGCCAATA GGGACTTTCC ATTGACGTCA ATGGGTGGAC TATTTACGGT

AAACTGCCCA CTTGGCAGTA CATCAAGTGT ATCATATGCC AAGTACGCCC CCTATTGACG TCAATGACGG TAAATGGCCC GCCTGGCATT

ATGCCCAGTA CATGACCTTA TGGGACTTTC CTACTTGGCA GTACATCTAC GTATTAGTCA TCGCTATTAC CATGGTGATG CGGTTTTGGC

AGTACATCAA TGGGCGTGGA TAGCGGTTTG ACTCACGGGG ATTTCCAAGT CTCCACCCCA TTGACGTCAA TGGGAGTTTG TTTTGGCACC

AAAATCAACG GGACTTTCCA AAATGTCGTA ACAACTCCGC CCCATTGACG CAAATGGGCG GTAGGCGTGT ACGGTGGGAG GTCTATATAA

GCAGAGCTCT CTGGCTAACT AGAGAACCCA CTGCTTACTG GCTTATCGAA ATTAATACGA CTCACTATAG GGAGACCCAA GCTGGCTAGC

GTTTAAACGG GCCCTCTAGA CTCGAGCGGC CGCCACTGTG CTGGATATCT GCAGAATTCC ACCACACTGG ACTAGTGGAT CCGAGCTCGG

TACCAAGCTT AAGTTTAAAC CGCTGATCAG CCTCGACTGT GCCTTCTAGT TGCCAGCCAT CTGTTGTTTG CCCCTCCCCC GTGCCTTCCT

TGACCCTGGA AGGTGCCACT CCCACTGTCC TTTCCTAATA AAATGAGGAA ATTGCATCGC ATTGTCTGAG TAGGTGTCAT TCTATTCTGG

GGGGTGGGGT GGGGCAGGAC AGCAAGGGGG AGGATTGGGA AGACAATAGC AGGCATGCTG GGGATGCGGT GGGCTCTATG GCTTCTGAGG

CGGAAAGAAC CAGCTGGGGC TCTAGGGGGT ATCCCCACGC GCCCTGTAGC GGCGCATTAA GCGCGGCGGG TGTGGTGGTT ACGCGCAGCG

TGACCGCTAC ACTTGCCAGC GCCCTAGCGC CCGCTCCTTT CGCTTTCTTC CCTTCCTTTC TCGCCACGTT CGCCGGCTTT CCCCGTCAAG

CTCTAAATCG GGGCATCCCT TTAGGGTTCC GATTTAGTGC TTTACGGCAC CTCGACCCCA AAAACTTGA TTAGGGTGAT GGTTCACGTA
```

```
GTGGGCCATC GCCCTGATAG ACGGTTTTTC GCCCTTTGAC GTTGGAGTCC ACGTTCTTTA ATAGTGGACT CTTGTTCCAA ACTGGAACAA
CACTCAACCC TATCTCGGTC TATTCTTTTG ATTTATAAGG GATTTGGGG ATTTCGGCCT ATTGGTTAAA AAATGAGCTG ATTTAACAAA
AATTTAACGC GAATTAATTC TGTGGAATGT GTGTCAGTTA GGGTGTGGAA AGTCCCCAGG CTCCCCAGGC AGGCAGAAGT ATGCAAAGCA
TGCATCTCAA TTAGTCAGCA ACCAGGTGTG GAAAGTCCCC AGGCTCCCCA GCAGGCAGAA GTATGCAAAG CATGCATCTC AATTAGTCAG
CAACCATAGT CCCGCCCCTA ACTCCGCCCA TCCCGCCCCT AACTCCGCCC AGTTCCGCCC ATTCTCCGCC CCATGGCTGA CTAATTTTTT
TTATTTATGC AGAGGCCGAG GCCGCCTCTG CCTCTGAGCT ATTCCAGAAG TAGTGAGGAG GCTTTTTTGG AGGCCTAGGC TTTTGCAAAA
AGCTCCCGGG AGCTTGTATA TCCATTTTCG GATCTGATCA AGAGACAGGA TGAGGATCGT TTCGCATGAT TGAACAAGAT GGATTGCACG
CAGGTTCTCC GGCCGCTTGG GTGGAGAGGC TATTCGGCTA TGACTGGGCA ACAGACAA TCGGCTGCTC TGATGCCGCC GTGTTCCGGC
TGTCAGCGCA GGGGCGCCCG GTTCTTTTTG TCAAGACCGA CCTGTCCGGT GCCCTGAATG AACTGCAGGA CGAGGCAGCG CGGCTATCGT
GGCTGGCCAC GACGGGCGTT CCTTGCGCAG CTGTGCTCGA CGTTGTCACT GAAGCGGGAA GGGACTGGCT GCTATTGGGC GAAGTGCCGG
GGCAGGATCT CCTGTCATCT CACCTTGCTC CTGCCGAGAA AGTATCCATC ATGGCTGATG CAATGCGGCG GCTGCATACG CTTGATCCGG
CTACCTGCCC ATTCGACCAC CAAGCGAAAC ATCGCATCGA GCGAGCACGT ACTCGGATGG AAGCCGGTCT TGTCGATCAG GATGATCTGG
ACGAAGAGCA TCAGGGGCTC GCGCCAGCCG AACTGTTCGC CAGGCTCAAG GCGCGCATGC CCGACGGCGA GGATCTCGTC GTGACCCATG
GCGATGCCTG CTTGCCGAAT ATCATGGTGG AAAATGGCCG CTTTTCTGGA TTCATCGACT GTGGCCGGCT GGGTGTGGCG GACCGCTATC
AGGACATAGC GTTGGCTACC CGTGATATTG CTGAAGAGCT TGGCGGCGAA TGGGCTGACC GCTTCCTCGT GCTTTACGGT ATCGCCGCTC
CCGATTCGCA GCGCATCGCC TTCTATCGCC TTCTTGACGA GTTCTTCTGA GCGGACTCT GGGGTTCGAA ATGACCGACC AAGCGACGCC
CAACCTGCCA TCACGAGATT TCGATTCCAC CGCCGCCTTC TATGAAAGGT TGGGCTTCGG AATCGTTTTC CGGGACGCCG GCTGGATGAT
CCTCCAGCGC GGGGATCTCA TGCTGGAGTT CTTCGCCCAC CCCAACTTGT TTATTGCAGC TTATAATGGT TACAAATAAA GCAATAGCAT
CACAAATTTC ACAAATAAAG CATTTTTTTC ACTGCATTCT AGTTGTGGTT TGTCCAAACT CATCAATGTA TCTTATCATG TCTGTATACC
GTCGACCTCT AGCTAGAGCT TGGCGTAATC ATGGTCATAG CTGTTTCCTG TGTGAAATTG TTATCCGCTC ACAATTCCAC ACAACATACG
AGCCGGAAGC ATAAAGTGTA AAGCCTGGGG TGCCTAATGA GTGAGCTAAC TCACATTAAT TGCGTTGCGC TCACTGCCCG CTTTCCAGTC
GGGAAACCTG TCGTGCCAGC TGCATTAATG AATCGGCCAA CGCGCGGGA GAGGCGGTTT GCGTATTGGG CGCTCTTCCG CTTCCTCGCT
CACTGACTCG CTGCGCTCGG TCGTTCGGCT GCGGCGAGCG GTATCAGCTC ACTCAAAGGC GGTAATACGG TTATCCACAG AATCAGGGGA
TAACGCAGGA AAGAACATGT GAGCAAAAGG CCAGCAATAG GCCAGGAACC GTAAAAAGGC CGCGTTGCTG GCGTTTTTCC ATAGGCTCCG
CCCCCCTGAC GAGCATCACA AAAATCGACG CTCAAGTCAG AGGTGGCGAA ACCCGACAGG ACTATAAAGA TACCAGGCGT TTCCCCCTGG
AAGCTCCCTC GTGCGCTCTC CTGTTCCGAC CCTGCCGCTT ACCGGATACC TGTCCGCCTT TCTCCCTTCG GGAAGCGTGG CGCTTTCTCA
ATGCTCACGC TGTAGGTATC TCAGTTCGGT GTAGGTCGTT CGCTCCAAGC TGGGCTGTGT GCACGAACCC CCCGTTCAGC CCGACCGCTG
CGCCTTATCC GGTAACTATC GTCTTGAGTC AACCCGGTA AGACACGACT TATCGCCACT GGCAGCAGCC ACTGGTAACA GGATTAGCAG
AGCGAGGTAT GTAGGCGGTG CTACAGAGTT CTTGAAGTGG TGGCCTAACT ACGGCTACAC TAGAAGGACA GTATTTGGTA TCTGCGCTCT
GCTGAAGCCA GTTACCTTCG GAAAAAGAGT TGGTAGCTCT TGATCCGGCA ACAAACCAC CGCTGGTAGC GGTGGTTTTT TTGTTTGCAA
GCAGCAGATT ACGCGCAGAA AAAAAGGATC TCAAGAAGAT CCTTTGATCT TTTCTACGGG GTCTGACGCT CAGTGGAACG AAAACTCACG
TTAAGGGATT TTGGTCATGA GATTATCAAA AAGGATCTTC ACCTAGATCC TTTTAAATTA AAAATGAAGT TTTAAATCAA TCTAAAGTAT
ATATGAGTAA ACTTGGTCTG ACAGTTACCA ATGCTTAATC AGTGAGGCAC CTATCTCAGC GATCTGTCTA TTTCGTTCAT CCATAGTTGC
CTGACTCCCC GTCGTGTAGA TAACTACGAT ACGGGAGGGC TTACCATCTG GCCCCAGTGC TGCAATGATA CCGCGAGACC CACGCTCACC
GGCTCCAGAT TTATCAGCAA TAAACCAGCC AGCCGGAAGG GCCGAGCGCA GAAGTGGTCC TGCAACTTTA TCCGCCTCCA TCCAGTCTAT
TAATTGTTGC CGGGAAGCTA GAGTAAGTAG TTCGCCAGTT AATAGTTTGC GCAACGTTGT TGCCATTGCT ACAGGCATCG TGGTGTCACG
CTCGTCGTTT GGTATGGCTT CATTCAGCTC CGGTTCCCAA CGATCAAGGC GAGTTACATG ATCCCCCATG TTGTGCAAAA AAGCGGTTAG
CTCCTTCGGT CCTCCGATCG TTGTCAGAAG TAAGTTGGCC GCAGTGTTAT CACTCATGGT TATGGCAGCA CTGCATAATT CTCTTACTGT
CATGCCATCC GTAAGATGCT TTTCTGTGAC TGGTGAGTAC TCAACCAAGT CATTCTGAGA ATAGTGTATG CGGCGACCGA GTTGCTCTTG
CCCGGCGTCA ATACGGGATA ATACCGCGCC ACATAGCAGA ACTTTAAAAG TGCTCATCAT TGGAAAACGT TCTTCGGGGC GAAAACTCTC
```

-continued
```
AAGGATCTTA CCGCTGTTGA GATCCAGTTC GATGTAACCC ACTCGTGCAC CCAACTGATC TTCAGCATCT TTTACTTTCA CCAGCGTTTC TGGGTGAGCA AAAACAGGAA GGCAAAATGC CGCAAAAAAG GGAATAAGGG CGACACGGAA ATGTTAATA CTCATACTCT TCCTTTTTCA ATATTATTGA AGCATTTATC AGGGTTATTG TCTCATGAGC GGATACATAT TTGAATGTAT TTAGAAAAAT AAACAAATAG GGGTTCCGCG

CACATTTCCC CGAAAAGTGC CACCTGACGT C
```

The nucleic acid sequence of plasmid construct pcDNA3-ETA(dII)/E7 (SEQ ID NO:9) is shown below. ETA(dII)/E7 is ligated in the EcoRI/BamHI sites of pcDNA3 vector. The nucleotides encoding ETA(dII)/E7 are shown in lower case bold.

```
           |    10     |    20     |    30     |    40     |    50     |    60     |    70     |    80
   1 GACGGATCGG GAGATCTCCC GATCCCCTAT GGTCGACTCT CAGTACAATC TGCTCTGATG CCGCATAGTT AAGCCAGTAT    80

81 CTGCTCCCTG CTTGTGTGTT GGAGGTCGCT GAGTAGTGCG CGAGCAAAAT TAAGCTACA ACAAGGCAAG GCTTGACCGA   160

161 CAATTGCATG AAGAATCTGC TTAGGGTTAG GCGTTTTGCG CTGCTTCGCG ATGTACGGGC CAGATATACG CGTTGACATT   240

241 GATTATTGAC TAGTTATTAA TAGTAATCAA TTACGGGGTC ATTAGTTCAT AGCCCATATA TGGAGTTCCG CGTTACATAA   320

321 CTTACGGTAA ATGGCCCGCC TGGCTGACCG CCCAACGACC CCCGCCCATT GACGTCAATA ATGACGTATG TTCCCATAGT   400

401 AACGCCAATA GGGACTTTCC ATTGACGTCA ATGGGTGGAC TATTTACGGT AAACTGCCCA CTTGGCAGTA CATCAAGTGT   480

481 ATCATATGCC AAGTACGCCC CCTATTGACG TCAATGACGG TAAATGGCCC GCCTGGCATT ATGCCCAGTA CATGACCTTA   560

561 TGGGACTTTC CTACTTGGCA GTACATCTAC GTATTAGTCA TCGCTATTAC CATGGTGATG CGGTTTTGGC AGTACATCAA   640

641 TGGGCGTGGA TAGCGGTTTG ACTCACGGGG ATTTCCAAGT CTCCACCCCA TTGACGTCAA TGGGAGTTTG TTTTGGCACC   720

721 AAAATCAACG GGACTTTCCA AAATGTCGTA ACAACTCCGC CCCATTGACG CAAATGGGCG GTAGGCGTGT ACGGTGGGAG   800

801 GTCTATATAA GCAGAGCTCT CTGGCTAACT AGAGAACCCA CTGCTTACTG GCTTATCGAA ATTAATACGA CTCACTATAG   880

881 GGAGACCCAA GCTGGCTAGC GTTTAAACG GCCCTCTAGA CTCGAGCGG CGCCACTGTG CTGGATATCT GCAGAATTCa    960

961 tgcgcctgca ctttcccgag ggcggcagcc tggccgcgct gaccgcgcac caggcttgcc acctgccgct ggagactttc  1040

1041 acccgtcatc gccagccgcg cggctgggaa caactggagc agtgcggcta tccggtgcag cggctggtcg ccctctacct  1120

1121 ggcggcgcgg ctgtcgtgga accaggtcga ccaggtgatc cgcaacgccc tggccagccc cggcagcggc ggcgacctgg  1200

1201 gcgaagcgat ccgcgagcag ccggagcagg cccgtctggc cctgacctg gccgccgccg agagcgagcg cttcgtccgg  1280

1281 cagggcaccg gcaacgacga ggccggcgcg gccaacgccg acgtggtgag cctgacctgc ccggtcgccg ccggtgaatg  1360

1361 cgcgggcccg gcggacagcg gcgacgccct gctggagcgc aactatccca ctggcgcgga gttcctcggc gacggcggcg  1440

1441 acgtcagctt cagcacccgc ggcacgcaga acgaattcat gcatggagat acacctacat tgcatgaata tatgttagat  1520

1521 ttgcaaccag agacaactga tctctactgt tatgagcaat aaatgacag ctcagaggag gaggatgaaa tagatggtcc  1600

1601 agctggacaa gcagaaccgg acagagccca ttacaatatt gtaacctttt gttgcaagtg tgactctacg cttcggttgt  1680

1681 gcgtacaaag cacacacgta gacattcgta ctttggaaga cctgttaatg ggcacactag gaattgtgtg ccccatctgt  1760

1761 tctcaaGGAT CCGAGCTCGG TACCAAGCTT AAGTTTAAAC CGCTGATCAG CCTCGACTGT GCCTTCTAGT TGCCAGCCAT   1840

1841 CTGTTGTTTG CCCCTCCCCC GTGCCTTCCT TGACCCTGGA AGGTGCCACT CCCACTGTCC TTTCCTAATA AAATGAGGAA   1920

1921 ATTGCATCGC ATTGTCTGAG TAGGTGTCAT TCTATTCTGG GGGGTGGGGT GGGGCAGGAC AGCAAGGGGG AGGATTGGGA   2000

2001 AGACAATAGC AGGCATGCTG GGGATGCGGT GGGCTCTATG GCTTCTGAGG CGGAAAGAAC CAGCTGGGGC TCTAGGGGGT   2080

2081 ATCCCCACGC GCCCTGTAGC GGCGCATTAA GCGCGGCGGG TGTGGTGGTT ACGCGCAGCG TGACCGCTAC ACTTGCCAGC   2160

2161 GCCCTAGCGC CCGCTCCTTT CGCTTTCTTC CCTTCCTTTC TCGCCACGTT CGCCGGCTTT CCCCGTCAAG CTCTAAATCG   2240

2241 GGGCATCCCT TTAGGGTTCC GATTTAGTGC TTTACGCAC CTCGACCCCA AAAAACTTGA TTAGGGTGAT GGTTCACGTA   2320

2321 GTGGGCCATC GCCCTGATAG ACGGTTTTTC GCCCTTTGAC GTTGGAGTCC ACGTTCTTTA ATAGTGGACT CTTGTTCCAA   2400

2401 ACTGGAACAA CACTCAACCC TATCTCGGTC TATTCTTTTG ATTTATAAGG GATTTTGGGG ATTTCGGCCT ATTGGTTAAA   2480

2481 AAATGAGCTG ATTTAACAAA AATTTAACGC GAATTAATTC TGTGGAATGT GTGTCAGTTA GGGTGTGGAA AGTCCCCAGG   2560
```

-continued

```
2561 CTCCCCAGGC AGGCAGAAGT ATGCAAAGCA TGCATCTCAA TTAGTCAGCA ACCAGGTGTG GAAAGTCCCC AGGCTCCCCA 2640
2641 GCAGGCAGAA GTATGCAAAG CATGCATCTC AATTAGTCAG CAACCATAGT CCCGCCCCTA ACTCCGCCCA TCCCGCCCCT 2720
2721 AACTCCGCCC AGTTCCGCCC ATTCTCCGCC CCATGGCTGA CTAATTTTTT TTATTTATGC AGAGGCCGAG GCCGCCTCTG 2800
2801 CCTCTGAGCT ATTCCAGAAG TAGTGAGGAG GCTTTTTTGG AGGCCTAGGC TTTTGCAAAA AGCTCCCGGG AGCTTGTATA 2880
2881 TCCATTTTCG GATCTGATCA AGAGACAGGA TGAGGATCGT TTCGCATGAT TGAACAAGAT GGATTGCACG CAGGTTCTCC 2960
2961 GGCCGCTTGG GTGGAGAGGC TATTCGGCTA TGACTGGGCA CAACAGACAA TCGGCTGCTC TGATGCCGCC GTGTTCCGGC 3040
3041 TGTCAGCGCA GGGGCGCCCG GTTCTTTTTG TCAAGACCGA CCTGTCCGGT GCCCTGAATG AACTGCAGGA CGAGGCAGCG 3120
3121 CGGCTATCGT GGCTGGCCAC GACGGGCGTT CCTTGCGCAG CTGTGCTCGA CGTTGTCACT GAAGCGGGAA GGGACTGGCT 3200
3201 GCTATTGGGC GAAGTGCCGG GGCAGGATCT CCTGTCATCT CACCTTGCTC CTGCCGAGAA AGTATCCATC ATGGCTGATG 3280
3281 CAATGCGGCG GCTGCATACG CTTGATCCGG CTACCTGCCC ATTCGACCAC CAAGCGAAAC ATCGCATCGA GCGAGCACGT 3360
3361 ACTCGGATGG AAGCCGGTCT TGTCGATCAG GATGATCTGG ACGAAGAGCA TCAGGGGCTC GCGCCAGCCG AACTGTTCGC 3440
3441 CAGGCTCAAG GCGCGCATGC CCGACGGCGA GGATCTCGTC GTGACCCATG GCGATGCCTG CTTGCCGAAT ATCATGGTGG 3520
3521 AAAATGGCCG CTTTTCTGGA TTCATCGACT GTGGCCGGCT GGGTGTGGCG GACCGCTATC AGGACATAGC GTTGGCTACC 3600
3601 CGTGATATTG CTGAAGAGCT TGGCGGCGAA TGGGCTGACC GCTTCCTCGT GCTTTACGGT ATCGCCGCTC CCGATTCGCA 3680
3681 GCGCATCGCC TTCTATCGCC TTCTTGACGA GTTCTTCTGA GCGGGACTCT GGGGTTCGAA ATGACCGACC AAGCGACGCC 3760
3761 CAACCTGCCA TCACGAGATT TCGATTCCAC CGCCGCCTTC TATGAAAGGT TGGGCTTCGG AATCGTTTTC CGGGACGCCG 3840
3841 GCTGGATGAT CCTCCAGCGC GGGGATCTCA TGCTGGAGTT CTTCGCCCAC CCCAACTTGT TTATTGCAGC TTATAATGGT 3920
3921 TACAAATAAA GCAATAGCAT CACAAATTTC ACAAATAAAG CATTTTTTTC ACTGCATTCT AGTTGTGGTT TGTCCAAACT 4000
4001 CATCAATGTA TCTTATCATG TCTGTATACC GTCGACCTCT AGCTAGAGCT TGGCGTAATC ATGGTCATAG CTGTTTCCTG 4080
4081 TGTGAAATTG TTATCCGCTC ACAATTCCAC ACAACATACG AGCCGGAAGC ATAAAGTGTA AAGCCTGGGG TGCCTAATGA 4160
4161 GTGAGCTAAC TCACATTAAT TGCGTTGCGC TCACTGCCCG CTTTCCAGTC GGGAAACCTG TCGTGCCAGC TGCATTAATG 4240
4241 AATCGGCCAA CGCGCGGGGA GAGGCGGTTT GCGTATTGGG CGCTCTTCCG CTTCCTCGCT CACTGACTCG CTGCGCTCGG 4320
4321 TCGTTCGGCT GCGGCGAGCG GTATCAGCTC ACTCAAAGGC GGTAATACGG TTATCCACAG AATCAGGGGA TAACGCAGGA 4400
4401 AAGAACATGT GAGCAAAAGG CCAGCAAAAG GCCAGGAACC GTAAAAAGGC CGCGTTGCTG GCGTTTTTCC ATAGGCTCCG 4480
4481 CCCCCCTGAC GAGCATCACA AAAATCGACG CTCAAGTCAG AGGTGGCGAA ACCCGACAGG ACTATAAAGA TACCAGGCGT 4560
4561 TTCCCCCTGG AAGCTCCCTC GTGCGCTCTC CTGTTCCGAC CCTGCCGCTT ACCGGATACC TGTCCGCCTT TCTCCCTTCG 4640
4641 GGAAGCGTGG CGCTTTCTCA ATGCTCACGC TGTAGGTATC TCAGTTCGGT GTAGGTCGTT CGCTCCAAGC TGGGCTGTGT 4720
4721 GCACGAACCC CCCGTTCAGC CCGACCGCTG CGCCTTATCC GGTAACTATC GTCTTGAGTC AACCCGGTA AGACACGACT 4800
4801 TATCGCCACT GGCAGCAGCC ACTGGTAACA GGATTAGCAG AGCGAGGTAT GTAGGCGGTG CTACAGAGTT CTTGAAGTGG 4880
4881 TGGCCTAACT ACGGCTACAC TAGAAGGACA GTATTTGGTA TCTGCGCTCT GCTGAAGCCA GTTACCTTCG GAAAAGAGT 4960
4961 TGGTAGCTCT TGATCCGGCA ACAAACCAC CGCTGGTAGC GGTGGTTTTT TGTTTGCAA GCAGCAGATT ACGCGCAGAA 5040
5041 AAAAGGATC TCAAGAAGAT CCTTTGATCT TTTCTACGGG GTCTGACGCT CAGTGGAACG AAAACTCACG TTAAGGGATT 5120
5121 TTGGTCATGA GATTATCAAA AAGGATCTTC ACCTAGATCC TTTTAAATTA AAAATGAAGT TTTAAATCAA TCTAAAGTAT 5200
5201 ATATGAGTAA ACTTGGTCTG ACAGTTACCA ATGCTTAATC AGTGAGGCAC CTATCTCAGC GATCTGTCTA TTTCGTTCAT 5280
5281 CCATAGTTGC CTGACTCCCC GTCGTGTAGA TAACTACGAT ACGGGAGGGC TTACCATCTG GCCCCAGTGC TGCAATGATA 5360
5361 CCGCGAGACC CACGCTCACC GGCTCCAGAT TTATCAGCAA TAAACCAGCC AGCCGGAAGG GCCGAGCGCA GAAGTGGTCC 5440
5441 TGCAACTTTA TCCGCCTCCA TCCAGTCTAT TAATTGTTGC CGGGAAGCTA GAGTAAGTAG TTCGCCAGTT AATAGTTTGC 5520
5521 GCAACGTTGT TGCCATTGCT ACAGGCATCG TGGTGTCACG CTCGTCGTTT GGTATGGCTT CATTCAGCTC CGGTTCCCAA 5600
5601 CGATCAAGGC GAGTTACATG ATCCCCCATG TTGTGCAAAA AAGCGGTTAG CTCCTTCGGT CCTCCGATCG TTGTCAGAAG 5680
5681 TAAGTTGGCC GCAGTGTTAT CACTCATGGT TATGGCAGCA CTGCATAATT CTCTTACTGT CATGCCATCC GTAAGATGCT 5760
```

-continued
```
5761 TTTCTGTGAC TGGTGAGTAC TCAACCAAGT CATTCTGAGA ATAGTGTATG CGGCGACCGA GTTGCTCTTG CCCGGCGTCA 5840

5841 ATACGGGATA ATACCGCGCC ACATAGCAGA ACTTTAAAAG TGCTCATCAT TGGAAAACGT TCTTCGGGGC GAAAACTCTC 5920

5921 AAGGATCTTA CCGCTGTTGA GATCCAGTTC GATGTAACCC ACTCGTGCAC CCAACTGATC TTCAGCATCT TTTACTTTCA 6000

6001 CCAGCGTTTC TGGGTGAGCA AAAACAGGAA GGCAAAATGC CGCAAAAAAG GGAATAAGGG CGACACGGAA ATGTTGAATA 6080

6081 CTCATACTCT TCCTTTTTCA ATATTATTGA AGCATTTATC AGGGTTATTG TCTCATGAGC GGATACATAT TTGAATGTAT 6160

6161 TTAGAAAAAT AAACAAATAG GGGTTCCGCG CACATTTCCC CGAAAAGTGC CACCTGACGT C                      6221
      |   10     |   20     |   30     |   40     |   50     |   60     |   70     |   80     |
```

General Recombinant DNA Methods

Basic texts disclosing general methods of molecular biology, all of which are incorporated by reference, include: Sambrook, J et al., *Molecular Cloning: A Laboratory Manual*, 2$^{nd}$ Edition, Cold Spring Harbor Press, Cold Spring Harbor, N.Y., 1989; Ausubel, F M et al. *Current Protocols in Molecular Biology*, Vol. 2, Wiley-Interscience, New York, (current edition); Kriegler, *Gene Transfer and Expression: A Laboratory Manual* (1990); Glover, D M, ed, DNA *Cloning: A Practical Approach*, vol. I & II, IRL Press, 1985; Albers, B. et al., *Molecular Biology of the Cell*, 2$^{nd}$ Ed., Garland Publishing, Inc., New York, N.Y. (1989); Watson, J D et al, *Recombinant DNA*, 2$^{nd}$ Ed., Scientific American Books, New York, 1992; and Old, R W et al., *Principles of Gene Manipulation: An Introduction to Genetic Engineering*, 2$^{nd}$ Ed., University of California Press, Berkeley, Calif. (1981).

Unless otherwise indicated, a particular nucleic acid sequence is intended to encompasses conservative substitution variants thereof (e.g., degenerate codon substitutions) and a complementary sequence. The term "nucleic acid" is synonymous with "polynucleotide" and is intended to include a gene, a cDNA molecule, an mRNA molecule, as well as a fragment of any of these such as an oligonucleotide, and further, equivalents thereof (explained more fully below). Sizes of nucleic acids are stated either as kilobases (kb) or base pairs (bp). These are estimates derived from agarose or polyacrylamide gel electrophoresis (PAGE), from nucleic acid sequences which are determined by the user or published. Protein size is stated as molecular mass in kilodaltons (kDa) or as length (number of amino acid residues). Protein size is estimated from PAGE, from sequencing, from presumptive amino acid sequences based on the coding nucleic acid sequence or from published amino acid sequences.

Specifically, cDNA molecules encoding the amino acid sequence corresponding to the fusion polypeptide of the present invention or fragments or derivatives thereof can be synthesized by the polymerase chain reaction (PCR) (see, for example, U.S. Pat. No. 4,683,202) using primers derived the sequence of the protein disclosed herein. These cDNA sequences can then be assembled into a eukaryotic or prokaryotic expression vector and the resulting vector can be used to direct the synthesis of the fusion polypeptide or its fragment or derivative by appropriate host cells, for example COS or CHO cells.

This invention includes isolated nucleic acids having a nucleotide sequence encoding the novel fusion polypeptides that comprise a translocation polypeptide and an antigen, fragments thereof or equivalents thereof. The term nucleic acid as used herein is intended to include such fragments or equivalents. The nucleic acid sequences of this invention can be DNA or RNA.

A cDNA nucleotide sequence the fusion polypeptide can be obtained by isolating total mRNA from an appropriate cell line. Double stranded cDNA is prepared from total mRNA. cDNA can be inserted into a suitable plasmid, bacteriophage or viral vector using any one of a number of known techniques.

In reference to a nucleotide sequence, the term "equivalent" is intended to include sequences encoding structurally homologous and/or a functionally equivalent proteins. For example, a natural polymorphism in ETA(dII) nucleotide sequence (especially at the third base of a codon) may be manifest as "silent" mutations which do not change the amino acid sequence. Furthermore, there may be one or more naturally occurring isoforms or related, immunologically cross-reactive family members of these proteins. Such isoforms or family members are defined as proteins that share function amino acid sequence similarity to, for example, ETA(dII)

Fragment of Nucleic Acid

A fragment of the nucleic acid sequence is defined as a nucleotide sequence having fewer nucleotides than the nucleotide sequence encoding the full length translocation polypeptide, antigenic polypeptide or the fusion thereof. This invention includes such nucleic acid fragments that encode polypeptides which retain (1) the ability of the fusion polypeptide to induce increases in frequency or reactivity of T cells, preferably CD8+ T cells, that are specific for the antigen part of the fusion polypeptide.

For example, a nucleic acid fragment as intended herein encodes a ETA(dII) polypeptide that retains the ability to improve the immunogenicity of an antigen when administered as a fusion polypeptide with an antigenic polypeptide or peptide.

Generally, the nucleic acid sequence encoding a fragment of a ETA(dII) polypeptide comprises of nucleotides from the sequence encoding the mature protein (or an active fragment thereof).

Nucleic acid sequences of this invention may also include linker sequences, natural or modified restriction endonuclease sites and other sequences that are useful for manipulations related to cloning, expression or purification of encoded protein or fragments. These and other modifications of nucleic acid sequences are described herein or are well-known in the art.

The techniques for assembling and expressing DNA coding sequences for translocation types of proteins, and DNA coding sequences for antigenic polypeptides, include synthesis of oligonucleotides, PCR, transforming cells, constructing vectors, expression systems, and the like; these are well-established in the art such that those of ordinary skill are familiar with standard resource materials, specific conditions and procedures.

Expression Vectors and Host Cells

This invention includes an expression vector comprising a nucleic acid sequence encoding a translocation polypeptide/ antigen fusion polypeptide, preferably a ETA(dII)/antigen fusion polypeptide operably linked to at least one regulatory sequence.

The term "expression vector" or "expression cassette" as used herein refers to a nucleotide sequence which is capable of affecting expression of a protein coding sequence in a host compatible with such sequences. Expression cassettes include at least a promoter operably linked with the polypeptide coding sequence; and, optionally, with other sequences, e.g., transcription termination signals. Additional factors necessary or helpful in effecting expression may also be included, e.g., enhancers.

"Operably linked" means that the coding sequence is linked to a regulatory sequence in a manner that allows expression of the coding sequence. Known regulatory sequences are selected to direct expression of the desired protein in an appropriate host cell. Accordingly, the term "regulatory sequence" includes promoters, enhancers and other expression control elements. Such regulatory sequences are described in, for example, Goeddel, *Gene Expression Technology. Methods in Enzymology*, vol. 185, Academic Press, San Diego, Calif. (1990)).

Thus, expression cassettes include plasmids, recombinant viruses, any form of a recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons (see Example 1, below), bacteriophages) to which fragments of DNA may be attached and become replicated. Vectors thus include, but are not limited to RNA, autonomous self-replicating circular or linear DNA or RNA, e.g., plasmids, viruses, and the like (U.S. Pat. No. 5,217,879), and includes both the expression and nonexpression plasmids. Where a recombinant microorganism or cell culture is described as hosting an "expression vector" this includes both extrachromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

Those skilled in the art appreciate that the particular design of an expression vector of this invention depends on considerations such as the host cell to be transfected and/or the type of protein to be expressed.

The present expression vectors comprise the full range of nucleic acid molecules encoding the various embodiments of the fusion polypeptide and its functional derivatives (defined herein) including polypeptide fragments, variants, etc.

Such expression vectors are used to transfect host cells (in vitro, ex vivo or in vivo) for expression of the DNA and production of the encoded proteins which include fusion proteins or peptides. It will be understood that a genetically modified cell expressing the fusion polypeptide may transiently express the exogenous DNA for a time sufficient for the cell to be useful for its stated purpose.

The present in invention provides methods for producing the fusion polypeptides, fragments and derivatives. For example, a host cell transfected with a nucleic acid vector that encodes the fusion polypeptide is cultured under appropriate conditions to allow expression of the polypeptide.

Host cells may also be transfected with one or more expression vectors that singly or in combination comprise DNA encoding at least a portion of the fusion polypeptide and DNA encoding at least a portion of a second protein, so that the host cells produce yet further fusion polypeptides that include both the portions.

A culture typically includes host cells, appropriate growth media and other byproducts. Suitable culture media are well known in the art. The fusion polypeptide can be isolated from medium or cell lysates using conventional techniques for purifying proteins and peptides, including ammonium sulfate precipitation, fractionation column chromatography (e.g. ion exchange, gel filtration, affinity chromatography, etc.) and/or electrophoresis (see generally, "Enzyme Purification and Related Techniques", *Methods in Enzymology*, 22:233-577 (1971)). Once purified, partially or to homogeneity, the recombinant polypeptides of the invention can be utilized in pharmaceutical compositions as described in more detail herein.

The term "isolated" as used herein, when referring to a molecule or composition, such as a translocation polypeptide or a nucleic acid coding therefor, means that the molecule or composition is separated from at least one other compound (protein, other nucleic acid, etc.) or from other contaminants with which it is natively associated or becomes associated during processing. An isolated composition can also be substantially pure. An isolated composition can be in a homogeneous state and can be dry or in aqueous solution. Purity and homogeneity can be determined, for example, using analytical chemical techniques such as polyacrylamide gel electrophoresis (PAGE) or high performance liquid chromatography (HPLC). Even where a protein has been isolated so as to appear as a homogenous or dominant band in a gel pattern, there are trace contaminants which co-purify with it.

Prokaryotic or eukaryotic host cells transformed or transfected to express the fusion polypeptide or a homologue or functional derivative thereof are within the scope of the invention. For example, the fusion polypeptide may be expressed in bacterial cells such as *E. coli*, insect cells (baculovirus), yeast, or mammalian cells such as Chinese hamster ovary cells (CHO) or human cells. Other suitable host cells may be found in Goeddel, (1990) supra or are otherwise known to those skilled in the art.

Expression in eukaryotic cells leads to partial or complete glycosylation and/or formation of relevant inter- or intra-chain disulfide bonds of the recombinant protein.

Although preferred vectors are described in the Examples, other examples of expression vectors are provided here. Examples of vectors for expression in yeast *S. cerevisiae* include pYepSec1 (Baldari et al., (1987) *EMBO J.* 6:229-234), pMFa (Kuijan et al (1982) *Cell* 30:933-943), pJRY88 (Schultz et al., (1987) *Gene* 54:113-123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3:2156-2165,) and the pVL series (Lucklow, V. A., and Summers, M. D., (1989) *Virology* 170:31-39). Generally, COS cells (Gluzman, Y., (1981) *Cell* 23:175-182) are used in conjunction with such vectors as pCDM 8 (Aruffo A. and Seed, B., supra, for transient amplification/expression in mammalian cells, while CHO (dhfr-negative CHO) cells are used with vectors such as pMT2PC (Kaufman et al. (1987), *EMBO J.* 6:187-195) for stable amplification/expression in mammalian cells. The NSO myeloma cell line (a glutamine synthetase expression system.) is available from Celltech Ltd.

Often, in fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al, (1988) *Gene* 69:301-315) and pET 11d (Studier et al., *Gene Expression Technology: Methods in Enzymology* 185, Academic Press, San Diego, Calif. (1990) 60-89). While target gene expression relies on host RNA polymerase transcription from the hybrid trp-lac fusion promoter in pTrc, expression of target genes inserted into pET 11d relies on transcription from the T7 gn10-lacO fusion promoter mediated by coexpressed viral RNA polymerase (T7gn1). Th is viral polymerase is supplied by host strains BL21(DE3) or HMS174(DE3) from a resident λ prophage harboring a T7gn1 under the transcriptional control of the lacUV 5 promoter.

One embodiment of this invention is a transfected cell which expresses novel fusion polypeptide.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and re-ligated in the form desired.

The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al, *Science* (1984) 223:1299; and Jay, E., *J Biol Chem* (1984) 259:6311.

Synthetic oligonucleotides are prepared by either the phosphotriester method as described by references cited above or the phosphoramidite method as described by Beaucage, S. L., and Caruthers, M. H., *Tet Lett* (1981) 22:1859; and Matteucci, M. D., and Caruthers, M. H., *J Am Chem Soc* (1981) 103:3185 and can be prepared using commercially available automated oligonucleotide synthesizers. Kinase treatment of single strands prior to annealing or for labeling is achieved using an excess, e.g., about 10 units of polynucleotide kinase to 1 nmole substrate in the presence of 50 mM Tris, pH 7.6, 10 mM $MgCl_2$, 5 mM dithiothreitol, 1-2 mM ATP, 1.7 pmoles γ-$^{32}$P-ATP (2.9 mCi/mmole), 0.1 mM spermidine, 0.1 mM EDTA.

Once the components of the desired vectors are thus available, they can be excised and ligated using standard restriction and ligation procedures. Site-specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 mg of plasmid or DNA sequence is cleaved by one unit of enzyme in about 20 ml of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using conventional methods and conditions. Ligations are performed using known, conventional methods. In vector construction employing "vector fragments", the fragment is commonly treated with bacterial alkaline phosphatase (BAP) or calf intestinal alkaline phosphatase (CIAP) in order to remove the 5' phosphate and prevent self-Alternatively, re-ligation can be prevented in vectors which have been double digested by additional restriction enzyme and separation of the unwanted fragments.

Any of a number of methods are used to introduce mutations into the coding sequence to generate the variants of the invention. These mutations include simple deletions or insertions, systematic deletions, insertions or substitutions of clusters of bases or substitutions of single bases.

For example, modifications of the ETA(dII) polypeptide or the antigenic polypeptide DNA sequence are created by site-directed mutagenesis, a well-known technique for which protocols and reagents are commercially available (Zoller, M J et al., *Nucleic Acids Res* (1982) 10:6487-6500 and Adelman, J P et al., *DNA* (1983) 2:183-193)). Correct ligations for plasmid construction are confirmed, for example, by first transforming *E. coli* strain MC1061 (Casadaban, M., et al., *J Mol Biol* (1980) 138:179-207) or other suitable host with the ligation mixture. Using conventional methods, transformants are selected based on the presence of the ampicillin-, tetracycline- or other antibiotic resistance gene (or other selectable marker) depending on the mode of plasmid construction. Plasmids are then prepared from the transformants with optional chloramphenicol amplification optionally following chloramphenicol amplification ((Clewell, D B et al., *Proc Natl Acad Sci USA* (1969)62:1159; Clewell, D. B., *J Bacteriol* (1972)110:667). Several mini DNA preps are commonly used. See, e.g., Holmes, D S, et al., *Anal Biochem* (1981) 114:193-197; Bimboim, H C et al., *Nucleic Acids Res* (1979) 7:1513-1523. The isolated DNA is analyzed by restriction and/or sequenced by the dideoxy nucleotide method of Sanger (*Proc Natl Acad Sci USA* (1977) 74:5463) as further described by Messing, et al., *Nucleic Acids Res* (1981) 9:309, or by the method of Maxam et al. *Methods in Enzymology* (1980) 65:499.

Vector DNA can be introduced into mammalian cells via conventional techniques such as calcium phosphate or calcium chloride co-precipitation, DEAE-dextran-mediated transfection, lipofection, or electroporation. Suitable methods for transforming host cells can be found in Sambrook et al. supra and other standard texts.

Often, in fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

Known fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). While target gene expression relies on host RNA polymerase transcription from the hybrid trp-lac fusion promoter in pTrc, expression of target genes inserted into pET 11d relies on transcription from the T7 gn10-lacO fusion promoter mediated by coexpressed viral RNA polymerase (T7gn1). Th is viral polymerase is supplied by host strains BL21(DE3) or HMS174(DE3) from a resident λ prophage harboring a T7gn1 under the transcriptional control of the lacUV 5 promoter.

Promoters and Enhancers

A promoter region of a DNA or RNA molecule binds RNA polymerase and promotes the transcription of an "operably linked" nucleic acid sequence. As used herein, a "promoter sequence" is the nucleotide sequence of the promoter which is found on that strand of the DNA or RNA which is transcribed by the RNA polymerase. Two sequences of a nucleic acid molecule, such as a promoter and a coding sequence, are "operably linked" when they are linked to each other in a manner which permits both sequences to be transcribed onto the same RNA transcript or permits an RNA transcript begun in one sequence to be extended into the second sequence. Thus, two sequences, such as a promoter sequence and a coding sequence of DNA or RNA are operably linked if transcription commencing in the promoter sequence will produce an RNA transcript of the operably linked coding sequence. In order to be "operably linked" it is not necessary that two sequences be immediately adjacent to one another in the linear sequence.

The preferred promoter sequences of the present invention must be operable in mammalian cells and may be either eukaryotic or viral promoters. Although preferred promoters are described in the Examples, other useful promoters and regulatory elements are discussed below. Suitable promoters may be inducible, repressible or constitutive. A "constitutive" promoter is one which is active under most conditions encountered in the cell's environmental and throughout development. An "inducible" promoter is one which is under environmental or developmental regulation. A "tissue specific" promoter is active in certain tissue types of an organism. An example of a constitutive promoter is the viral promoter MSV-LTR, which is efficient and active in a variety of cell types, and, in contrast to most other promoters, has the same enhancing activity in arrested and growing cells. Other preferred viral promoters include that present in the CMV-LTR (from cytomegalovirus) (Bashart, M. et al., *Cell* 41:521 (1985)) or in the RSV-LTR (from Rous sarcoma virus) (Gorman, C. M., *Proc. Natl. Acad. Sci. USA* 79:6777 (1982). Also useful are the promoter of the mouse metallothionein I gene (Hamer, D., et al., *J. Mol. Appl. Gen.* 1:273-288 (1982)); the TK promoter of Herpes virus (McKnight, S., *Cell* 31:355-365 (1982)); the SV40 early promoter (Benoist, C., et al., *Nature* 290:304-310 (1981)); and the yeast gal4 gene promoter (Johnston, S. A., et al., *Proc. Natl. Acad. Sci.* (USA) 79:6971-6975 (1982); Silver, P. A., et al., *Proc. Natl. Acad. Sci.* (USA) 81:5951-5955 (1984)). Other illustrative descriptions of transcriptional factor association with promoter regions and the separate activation and DNA binding of transcription factors include: Keegan et al, *Nature* (1986) 231:699; Fields et al., *Nature* (1989) 340:245; Jones, *Cell* (1990) 61:9; Lewin, *Cell* (1990) 61:1161; Ptashne et al., *Nature* (1990) 346:329; Adams et al., *Cell* (1993) 72:306. The relevant disclosure of all of these above-listed references is hereby incorporated by reference.

The promoter region may further include an octamer region which may also function as a tissue specific enhancer, by interacting with certain proteins found in the specific tissue. The enhancer domain of the DNA construct of the present invention is one which is specific for the target cells to be transfected, or is highly activated by cellular factors of such target cells. Examples of vectors (plasmid or retrovirus) are disclosed in (Roy-Burman et al., U.S. Pat. No. 5,112,767). For a general discussion of enhancers and their actions in transcription, see, Lewin, B. M., *Genes IV*, Oxford University Press, Oxford, (1990), pp. 552-576. Particularly useful are retroviral enhancers (e.g., viral LTR). The enhancer is preferably placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency.

Nucleic acids of the invention can also be chemically synthesized using standard techniques. Various methods of chemically synthesizing polydeoxynucleotides are known, including solid-phase synthesis which, like peptide synthesis, has been fully automated with commercially available DNA synthesizers (See, e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

Proteins and Polypeptides

The terms "polypeptide," "protein," and "peptide" when referring to compositions of the invention are meant to include variants, analogues, and mimetics with structures and/or activity that substantially correspond to the polypeptide or peptide from which the variant, etc., was derived.

The present invention includes an "isolated" fusion polypeptide comprising a translocation polypeptide linked to an antigenic polypeptide. A preferred translocation polypeptide is ETA(dII), preferably SEQ ID NO:3. A preferred fusion polypeptide is ETA(dII)/E7, e.g., residues 1-269 of SEQ ID NO:5. While the present disclosure exemplifies a particular ETA(dII) sequence, it is to be understood that homologues of ETA(dII) from other bacteria (or from eukaryotic origin if such are found) and mutants thereof that possess the characteristics disclosed herein are intended within the scope of this invention.

The term "chimeric" or "fusion" polypeptide or protein refers to a composition comprising at least one polypeptide or peptide sequence or domain that is chemically bound in a linear fashion with a second polypeptide or peptide domain. One embodiment of this invention is an isolated or recombinant nucleic acid molecule encoding a fusion protein comprising at least two domains, wherein the first domain comprises a translocation polypeptide, e.g., ETA(dII), and the second domain comprising an antigenic epitope, e.g., an MHC class I-binding peptide epitope. Additional domains can comprise a polypeptide, peptide, polysaccharide, or the like. The "fusion" can be an association generated by a peptide bond, a chemical linking, a charge interaction (e.g., electrostatic attractions, such as salt bridges, H-bonding, etc.) or the like. If the polypeptides are recombinant, the "fusion protein" can be translated from a common mRNA. Alternatively, the compositions of the domains can be linked by any chemical or electrostatic means. The chimeric molecules of the invention (e.g., translocation polypeptide fusion proteins) can also include additional sequences, e.g., linkers, epitope tags, enzyme cleavage recognition sequences, signal sequences, secretion signals, and the like. Alternatively, a peptide can be linked to a carrier simply to facilitate manipulation or identification/location of the peptide.

Also included is a "functional derivative" of ETA(dII), which refers to an amino acid substitution variant, a "fragment," or a "chemical derivative" of the protein, which terms are defined below. A functional derivative retains measurable ETA(dII)-like activity, preferably that of promoting immunogenicity of one or more antigenic epitopes fused thereto by, e.g., promoting presentation by class I pathways which permits the "functional derivative's" utility in accordance with the present invention. "Functional derivatives" encompass "variants" and "fragments" regardless of whether the terms are used in the conjunctive or the alternative herein.

A functional homologue must possess the above biochemical and biological activity. In view of this functional characterization, use of homologous ETA(dII) proteins including proteins not yet discovered, fall within the scope of the invention if these proteins have sequence similarity and the recited biochemical and biological activity.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred method of alignment, Cys residues are aligned.

In a preferred embodiment, the length of a sequence being compared is at least 30%, preferably at least 40%, more preferably at least 50%, even more preferably at least 60%, and even more preferably at least 70%, 80%, or 90% of the length of the reference sequence (e.g., ETA(dII), SEQ ID NO:3). The amino acid residues (or nucleotides) at corresponding amino acid (or nucleotide) positions are then compared. When a position in the first sequence is occupied by the same amino acid residue (or nucleotide) as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to ETA(dII) nucleic acid molecules. BLAST protein searches can be performed with the XBLAST program, score=50, wordlength=3 to obtain amino acid sequences homologous to HVP22 protein molecules. To obtain gapped alignments for comparison purposes, Gapped BLAST can be utilized as described in Altschul et al. (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

Thus, a homologue of ETA(dII) as described above is characterized as having (a) functional activity of native ETA(dII) and (b) sequence similarity to a native ETA(dII) protein (such as SEQ ID NO:3) when determined as above, of at least about 20% (at the amino acid level), preferably at least about 40%, more preferably at least about 70%, even more preferably at least about 90%.

It is within the skill in the art to obtain and express such a protein using DNA probes based on the disclosed sequences of ETA(dII). Then, the fusion protein's biochemical and biological activity can be tested readily using art-recognized methods such as those described herein, for example, a T cell proliferation, cytokine secretion or a cytolytic assay, or an in vivo assay of tumor protection or tumor therapy. A biological assay of the stimulation of antigen-specific T cell reactivity will indicate whether the homologue has the requisite activity to qualify as a "functional" homologue.

A "variant" refers to a molecule substantially identical to either the full protein or to a fragment thereof in which one or more amino acid residues have been replaced (substitution variant) or which has one or several residues deleted (deletion variant) or added (addition variant). A "fragment" of ETA (dII) refers to any subset of the molecule, that is, a shorter polypeptide of the full-length protein.

A number of processes can be used to generate fragments, mutants and variants of the isolated DNA sequence. Small subregions or fragments of the nucleic acid encoding the spreading protein, for example 1-30 bases in length, can be prepared by standard, chemical synthesis. Antisense oligonucleotides and primers for use in the generation of larger synthetic fragment.

A preferred group of variants are those in which at least one amino acid residue and preferably, only one, has been substituted by different residue. For a detailed description of protein chemistry and structure, see Schulz, G E et al., *Principles of Protein Structure*, Springer-Verlag, New York, 1978, and Creighton, T. E., *Proteins: Structure and Molecular Properties*, W.H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIGS. 3-9 of Creighton (supra). Based on such an analysis, conservative substitutions are defined herein as exchanges within one of the following five groups:

| | | |
|---|---|---|
| 1 | Small aliphatic, nonpolar or slightly polar residues | Ala, Ser, Thr (Pro, Gly); |
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

More substantial changes in biochemical, functional (or immunological) properties are made by selecting substitutions that are less conservative, such as between, rather than within, the above five groups. Such changes will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (i) substitution of Gly and/or Pro by another amino acid or deletion or insertion of Gly or Pro; (ii) substitution of a hydrophilic residue, e.g., Ser or Thr, for (or by) a hydrophobic residue, e.g., Leu, Ile, Phe, Val or Ala; (iii) substitution of a Cys residue for (or by) any other residue; (iv) substitution of a residue having an electropositive side chain, e.g., Lys, Arg or His, for (or by) a residue having an electronegative charge, e.g., Glu or Asp; or (v) substitution of a residue having a bulky side chain, e.g., Phe, for (or by) a residue not having such a side chain, e.g., Gly.

Most acceptable deletions, insertions and substitutions according to the present invention are those that do not produce radical changes in the characteristics of the wild-type or native protein in terms of its intercellular spreading activity and its ability to stimulate antigen specific T cell reactivity to an antigenic epitope or epitopes that are fused to the spreading protein. However, when it is difficult to predict the exact effect of the substitution, deletion or insertion in advance of doing so, one skilled in the art will appreciate that the effect can be evaluated by routine screening assays such as those described here, without requiring undue experimentation.

Whereas shorter chain variants can be made by chemical synthesis, for the present invention, the preferred longer chain variants are typically made by site-specific mutagenesis of the nucleic acid encoding the polypeptide, expression of the variant nucleic acid in cell culture, and, optionally, purification of the polypeptide from the cell culture, for example, by immunoaffinity chromatography using specific antibody immobilized to a column (to absorb the variant by binding to at least one epitope).

The term "chemically linked" refers to any chemical bonding of two moieties, e.g., as in one embodiment of the invention, where a translocation polypeptide is chemically linked to an antigenic peptide. Such chemical linking includes the peptide bonds of a recombinantly or in vivo generated fusion protein.

Chemical Derivatives

"Chemical derivatives" of the polypeptide or fusion polypeptide of the invention contain additional chemical moieties not normally a part of the protein. Covalent modifications of the polypeptide are included within the scope of this invention. Such derivatized moieties may improve the solubility, absorption, biological half life, and the like. Moieties capable of mediating such effects are disclosed, for example, in *Remington's Pharmaceutical Sciences,* $16^{th}$ ed., Mack Publishing Co., Easton, Pa. (1980).

Such modifications may be introduced into the molecule by reacting targeted amino acid residues of the polypeptide with an organic derivatizing agent that is capable of reacting with selected side chains or terminal residues. Another modification is cyclization of the protein. Examples of chemical derivatives of the polypeptide follow.

Lysinyl and amino terminal residues are derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Carboxyl side groups, aspartyl or glutamyl, may be selectively modified by reaction with carbodiimides (R—N═C═N—R') such as 1-cyclohexyl-3-(2-morpholinyl-(4-ethyl)carbodiimide or 1-ethyl-3-(4-azonia-4,4-dimethylpentyl)carbodiimide. Furthermore, aspartyl and glutamyl residues can be converted to asparaginyl and glutaminyl residues by reaction with ammonia.

Other modifications include hydroxylation of proline and lysine, phosphorylation of hydroxyl groups of seryl or threonyl residues, methylation of the amino group of lysine (Creighton, supra, pp. 79-86), acetylation of the N-terminal amine, and amidation of the C-terminal carboxyl groups.

Also included are peptides wherein one or more D-amino acids are substituted for one or more L-amino acids.

Multimeric Peptides

The present invention also includes longer polypeptides in which a basic peptidic sequence obtained from the sequence of a translocation polypeptide, or the antigenic polypeptide or peptide unit, is repeated from about two to about 100 times, with or without intervening spacers or linkers. It is understood that such multimers may be built from any of the peptide variants defined herein. Moreover, a peptide multimer may comprise different combinations of peptide monomers and the disclosed substitution variants thereof. Such oligomeric or multimeric peptides can be made by chemical synthesis or by recombinant DNA techniques as discussed herein. When produced chemically, the oligomers preferably have from 2-12 repeats of the basic peptide sequence. When produced recombinantly, the multimers may have as many repeats as the expression system permits, for example from two to about 100 repeats.

In tandem multimers, preferably dimers and trimers, of the fusion polypeptide, the chains bonded by interchain disulfide bonds or other "artificial" covalent bonds between the chains such that the chains are "side-by-side" rather than "end to end."

Therapeutic Compositions and their Administration

A vaccine composition comprising the nucleic acid encoding the fusion polypeptide, or a cell expressing this nucleic acid is administered to a mammalian subject, preferably a human. The vaccine composition is administered in a pharmaceutically acceptable carrier in a biologically effective or a therapeutically effective amount. The composition may be given alone or in combination with another protein or peptide such as an immunostimulatory molecule. Treatment may include administration of an adjuvant, used in its broadest sense to include any nonspecific immune stimulating compound such as an interferon. Adjuvants contemplated herein include resorcinols, non-ionic surfactants such as polyoxyethylene oleyl ether and n-hexadecyl polyethylene ether.

A therapeutically effective amount is a dosage that, when given for an effective period of time, achieves the desired immunological or clinical effect.

A therapeutically active amount of a nucleic acid encoding the fusion polypeptide may vary according to factors such as the disease state, age, sex, and weight of the individual, and the ability of the peptide to elicit a desired response in the individual. Dosage regimes may be adjusted to provide the optimum therapeutic response. For example, several divided doses may be administered daily or the dose may be proportionally reduced as indicated by the exigencies of the therapeutic situation. A therapeutically effective amounts of the protein, in cell associated form may be stated in terms of the protein or cell equivalents.

Thus an effective amount is between about 1 nanogram and about 1 gram per kilogram of body weight of the recipient, more preferably between about 0.1 µg/kg and about 10 mg/kg, more preferably between about 1 µg/kg and about 1 mg/kg. Dosage forms suitable for internal administration preferably contain (for the latter dose range) from about 0.1 µg to 100 µg of active ingredient per unit. The active ingredient may vary from 0.5 to 95% by weight based on the total weight of the composition. Alternatively, an effective dose of cells expressing the nucleic acid is between about $10^4$ and $10^8$ cells. Those skilled in the art of immunotherapy will be able to adjust these doses without undue experimentation.

The active compound may be administered in a convenient manner, e.g., injection by a convenient and effective route. Preferred routes include subcutaneous, intradermal, intravenous and intramuscular routes. Other possible routes include oral administration, intrathecal, inhalation, transdermal application, or rectal administration. For the treatment of existing tumors which have not been completely resected or which have recurred, direct intratumoral injection is also intended.

Depending on the route of administration, the active compound may be coated in a material to protect the compound from the action of enzymes, acids and other natural conditions which may inactivate the compound. Thus it may be necessary to coat the composition with, or co-administer the composition with, a material to prevent its inactivation. For example, an enzyme inhibitors of nucleases or proteases (e.g., pancreatic trypsin inhibitor, diisopropylfluorophosphate and trasylol).or in an appropriate carrier such as liposomes (including water-in-oil-in-water emulsions as well as conventional liposomes (Strejan et al., (1984) *J. Neuroimmunol* 7:27).

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

Preferred pharmaceutically acceptable diluents include saline and aqueous buffer solutions. Pharmaceutical compositions suitable for injection include sterile aqueous solutions (where water soluble) or dispersions and sterile powders for the extemporaneous preparation of sterile injectable solutions or dispersion. Isotonic agents, for example, sugars, polyalcohols such as mannitol, sorbitol, sodium chloride may be included in the pharmaceutical composition. In all cases, the composition should be sterile and should be fluid. It should be stable under the conditions of manufacture and storage and must include preservatives that prevent contamination with microorganisms such as bacteria and fungi. Dispersions can also be prepared in glycerol, liquid polyethylene glycols, and mixtures thereof and in oils. Under ordinary conditions of storage and use, these preparations may contain a preservative to prevent the growth of microorganisms.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like.

Compositions are preferably formulated in dosage unit form for ease of administration and uniformity of dosage. Dosage unit form refers to physically discrete units suited as unitary dosages for a mammalian subject; each unit contains a predetermined quantity of active material (e.g., the nucleic acid vaccine) calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects For lung instillation, aerosolized solutions are used. In a sprayable aerosol preparations, the active protein may be in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the protein of the invention.

Other pharmaceutically acceptable carriers for the nucleic acid vaccine compositions according to the present invention are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Those skilled in the art will appreciate other suitable embodiments of the present liposomal formulations.

Antigens Associated with Pathogens

A major use for the present invention is the use of the present nucleic acid compositions in therapeutic vaccine for cancer and for major chronic viral infections that cause morbidity and mortality worldwide. Such vaccines are designed to eliminate infected cells—this requires T cell responses as antibodies are often ineffective. The vaccines of the present invention are designed to meet these needs.

Preferred antigens are epitopes of pathogenic microorganisms against which the host is defended by effector T cells responses, including cytotoxic T lymphocyte (CTL) and delayed type hypersensitivity. These typically include viruses, intracellular parasites such as malaria, and bacteria that grow intracellularly such as Mycobacteria and Listeria species. Thus, the types of antigens included in the vaccine compositions of this invention are any of those associated with such pathogens (in addition, of course, to tumor-specific antigens). It is noteworthy that some viral antigens are also tumor antigens in the case where the virus is a causative factor in cancer.

In fact, the two most common cancers worldwide, hepatoma and cervical cancer, are associated with viral infection. Hepatitis B virus (HBV) (Beasley, R. P. et al., *Lancet* 2, 1129-1133 (1981) has been implicated as etiologic agent of hepatomas. 80-90% of cervical cancers express the E6 and E7 antigens (exemplified herein) from one of four "high risk" human papillomavirus types: HPV-16, HPV-18, HPV-31 and HPV-45 (Gissmann, L. et al., *Ciba Found Symp.* 120, 190-207 (1986); Beaudenon, S., et al. *Nature* 321, 246-249 (1986). The HPV E6 and E7 antigens are the most promising targets for virus associated cancers in immunocompetent individuals because of their ubiquitous expression in cervical cancer. In addition to their importance as targets for therapeutic cancer vaccines, virus associated tumor antigens are also ideal candidates for prophylactic vaccines. Indeed, introduction of prophylactic HBV vaccines in Asia have decreased the incidence of hepatoma (Chang, M. H., et al. *New Engl. J Med.* 336, 1855-1859 (1997), representing a great impact on cancer prevention.

Among the most important viruses in chronic human viral infections are HPV, HBV, hepatitis C Virus (HCV), human immunodeficiency virus (HIV-1 and HIV-2), herpesviruses such as Epstein Barr Virus (EBV), cytomegalovirus (CMV) and HSV-1 and HSV-2 and influenza virus. Useful antigens include HBV surface antigen or HBV core antigen; ppUL83 or pp89 of CMV; antigens of gp120, gp41 or p24 proteins of HIV-1; ICP27, gD2, gB of HSV; or influenza nucleoprotein (Anthony, L S et al., *Vaccine* 1999; 17:373-83). Other antigens associated with pathogens that can be utilized as described herein are antigens of various parasites, includes malaria, preferably malaria peptide (NANP)40.

In addition to its applicability to human cancer and infectious diseases, the present invention is also intended for use in treating animal diseases in the veterinary medicine context. Thus, the approaches described herein may be readily applied by one skilled in the art to treatment of veterinary herpesvirus infections including equine herpesviruses, bovine viruses such as bovine viral diarrhea virus (for example, the E2 antigen), bovine herpesviruses, Marek's disease virus in chickens and other fowl; animal retroviral and lentiviral diseases (e.g., feline leukemia, feline immunodeficiency, simian immunodeficiency viruses, etc.); pseudorabies and rabies; and the like.

As for tumor antigens, any tumor-associated or tumor-specific antigen that can be recognized by T cells, preferably by CTL, can be used. In addition to the HPV-E7 antigen exemplified herein is mutant p53 or HER2/neu or a peptide thereof. Any of a number of melanoma-associated antigens may be used, such as MAGE-1, MAGE-3, MART-1/Melan-A, tyrosinase, gp75, gp100, BAGE, GAGE-1, GAGE-2, GnT-V, and p15 (see, U.S. Pat. No. 6,187,306).

The following references set forth principles and current information in the field of basic, medical and veterinary virology and are incorporated by reference: *Fields Virology*, Fields, B N et al., eds., Lippincott Williams & Wilkins, NY, 1996; *Principles of Virology: Molecular Biology, Pathogenesis, and Control*, Flint, S. J. et al., eds., Amer Society for Microbiology, Washington, 1999; *Principles and Practice of Clinical Virology*, 4th Edition, Zuckerman. A. J. et al., eds, John Wiley & Sons, NY, 1999; *The Hepatitis C Viruses*, by Hagedorn, C H et al., eds., Springer Verlag, 1999; *Hepatitis B Virus: Molecular Mechanisms in Disease and Novel Strategies for Therapy*, Koshy, R. et al., eds, World Scientific Pub Co, 1998; *Veterinary Virology*, Murphy, F. A. et al., eds., Academic Press, NY, 1999; *Avian Viruses: Function and Control Ritchie*, B. W., Iowa State University Press, Ames, 2000; *Virus Taxonomy: Classification and Nomenclature of Viruses: Seventh Report of the International Committee on Taxonomy of Viruses*, by M. H. V. Van Regenmortel, M H V et al., eds., Academic Press; NY, 2000.

Delivery of Vaccine Nucleic Acid to Cells and Animals

The Examples below describe certain preferred approaches to delivery of the vaccines of the present invention. A broader description of other approaches including viral and nonviral vectors and delivery mechanisms follow.

DNA delivery involves introduction of a "foreign" DNA into a cell ex vivo and ultimately, into a live animal or directly into the animal. Several general strategies for gene delivery (=delivery of nucleic acid vectors) for purposes that include "gene therapy" have been studied and reviewed extensively (Yang, N-S., *Crit. Rev. Biotechnol.* 12:335-356 (1992); Anderson, W. F., *Science* 256:808-813 (1992); Miller, A. S., *Nature* 357:455-460 (1992); Crystal, R. G., *Amer. J. Med.* 92(suppl 6A):44S-52S (1992); Zwiebel, J. A. et al., *Ann. N. Y. Acad. Sci.* 618:394-404 (1991); McLachlin, J. R. et al., *Prog. Nucl. Acid Res. Molec. Biol.* 38:91-135 (1990); Kohn, D. B. et al., *Cancer Invest.* 7:179-192 (1989), which references are herein incorporated by reference in their entirety).

One approach comprises nucleic acid transfer into primary cells in culture followed by autologous transplantation of the ex vivo transformed cells into the host, either systemically or into a particular organ or tissue.

The term "systemic administration" refers to administration of a composition or agent such as a molecular vaccine as described herein, in a manner that results in the introduction of the composition into the subject's circulatory system or otherwise permits its spread throughout the body. "Regional" administration refers to administration into a specific, and somewhat more limited, anatomical space, such as intraperitoneal, intrathecal, subdural, or to a specific organ. The term "local administration" refers to administration of a composition or drug into a limited, or circumscribed, anatomic space, such as intratumoral injection into a tumor mass, subcutaneous injections, intramuscular injections. One of skill in the art would understand that local administration or regional administration may also result in entry of a composition into the circulatory system.

For accomplishing the objectives of the present invention, nucleic acid therapy would be accomplished by direct transfer of a the functionally active DNA into mammalian somatic tissue or organ in vivo. DNA transfer can be achieved using a number of approaches described below. These systems can be tested for successful expression in vitro by use of a selectable marker (e.g., G418 resistance) to select transfected clones expressing the DNA, followed by detection of the presence of the antigen-containing expression product (after treatment with the inducer in the case of an inducible system) using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a "carrier".

Examples of successful "gene transfer" reported in the art include: (a) direct injection of plasmid DNA into mouse muscle tissues, which led to expression of marker genes for an indefinite period of time (Wolff, J. A. et al., *Science* 247:1465 (1990); Acsadi, G. et al., *The New Biologist* 3:71 (1991)); (b) retroviral vectors are effective for in vivo and in situ infection of blood vessel tissues; (c) portal vein injection and direct injection of retrovirus preparations into liver effected gene transfer and expression in vivo (Horzaglou, M. et al., *J. Biol. Chem.* 265:17285 (1990); Koleko, M. et al., *Human Gene Therapy* 2:27 (1991); Ferry, N. et al., *Proc. Natl. Acad. Sci. USA* 88:8387 (1991)); (d) intratracheal infusion of recombinant adenovirus into lung tissues was effective for in vivo transfer and prolonged expression of foreign genes in lung respiratory epithelium (Rosenfeld, M. A. et al., *Science* 252: 431 (1991); (e) Herpes simplex virus vectors achieved in vivo gene transfer into brain tissue (Ahmad, F. et al., eds, *Miami Short Reports—Advances in Gene Technology: The Molecular Biology of Human Genetic Disease*, Vol 1, Boehringer Manneheim1 Biochemicals, USA, 1991).

Retroviral-mediated human therapy utilizes amphotrophic, replication-deficient retrovirus systems (Temin, H. M., *Human Gene Therapy* 1:111 (1990); Temin et al., U.S. Pat. No. 4,980,289; Temin et al, U.S. Pat. No. 4,650,764; Temin et al., U.S. Pat. No. 5,124,263; Wills, J. W. U.S. Pat. No. 5,175,099; Miller, A. D., U.S. Pat. No. 4,861,719). Such vectors have been used to introduce functional DNA into human cells or tissues, for example, the adenosine deaminase gene into lymphocytes, the NPT-II gene and the gene for tumor necrosis factor into tumor infiltrating lymphocytes. Retrovirus-mediated gene delivery generally requires target cell proliferation for gene transfer (Miller, D. G. et al., *Mol. Cell. Biol.* 10:4239 (1990). This condition is met by certain of the preferred target cells into which the present DNA molecules are to be introduced, i.e., actively growing tumor cells. Gene therapy of cystic fibrosis using transfection by plasmids using any of a number of methods and by retroviral vectors has been described by Collins et al., U.S. Pat. No. 5,240,846.

The DNA molecules encoding the fusion polypeptides of the present invention may be packaged into retrovirus vectors using packaging cell lines that produce replication-defective retroviruses, as is well-known in the art (see, for example, Cone, R. D. et al., *Proc. Natl. Acad. Sci. USA* 81:6349-6353 (1984); Mann, R. F. et al., *Cell* 33:153-159 (1983); Miller, A. D. et al., *Molec. Cell. Biol.* 5:431-437 (1985); Sorge, J., et al., *Molec. Cell. Biol.* 4:1730-1737 (1984); Hock, R. A. et al., *Nature* 320:257 (1986); Miller, A. D. et al., *Molec. Cell. Biol.* 6:2895-2902 (1986). Newer packaging cell lines which are efficient an safe for gene transfer have also been described (Bank et al., U.S. Pat. No. 5,278,056.

This approach can be utilized in a site specific manner to deliver the retroviral vector to the tissue or organ of choice. Thus, for example, a catheter delivery system can be used (Nabel, E G et al., *Science* 244:1342 (1989)). Such methods, using either a retroviral vector or a liposome vector, are particularly useful to deliver the nucleic acid to be expressed to a blood vessel wall, or into the blood circulation of a tumor.

Other virus vectors may also be used, including recombinant adenoviruses (Horowitz, M. S., In: *Virology*, Fields, B N et al., eds, Raven Press, New York, 1990, p. 1679; Berkner, K. L., *Biotechniques* 6:616 9191988), Strauss, S. E., In: *The Adenoviruses*, Ginsberg, H S, ed., Plenum Press, New York, 1984, chapter 11), herpes simplex virus (HSV) for neuron-specific delivery and persistence. Advantages of adenovirus vectors for human gene delivery include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms. Adeno-associated virus is also useful for human therapy (Samulski, R. J. et al., *EMBO J.* 10:3941 (1991) according to the present invention.

Another vector which can express the DNA molecule of the present invention, and is useful in the present therapeutic setting, particularly in humans, is vaccinia virus, which can be rendered non-replicating (U.S. Pat. Nos. 5,225,336; 5,204, 243; 5,155,020; 4,769,330; Sutter, G et al., *Proc. Natl. Acad. Sci. USA* (1992) 89:10847-10851; Fuerst, T. R. et al., *Proc. Natl. Acad. Sci. USA* (1989) 86:2549-2553; Falkner F. G. et al.; *Nucl. Acids Res* (1987) 15:7192; Chakrabarti, S et al., *Molec. Cell. Biol.* (1985) 5:3403-3409). Descriptions of recombinant vaccinia viruses and other viruses containing heterologous DNA and their uses in immunization and DNA therapy are reviewed in: Moss, B., *Curr. Opin. Genet. Dev.* (1993) 3:86-90; Moss, B. *Biotechnology* (1992) 20:345-362; Moss, B., *Curr Top Microbiol Immunol* (1992) 158:25-38; Moss, B., *Science* (1991) 252:1662-1667; Piccini, A et al., *Adv. Virus Res.* (1988) 34:43-64; Moss, B. et al., *Gene Amplif Anal* (1983) 3:201-213.

In addition to naked DNA or RNA, or viral vectors, engineered bacteria may be used as vectors. A number of bacterial strains including Salmonella, BCG and *Listeria monocytogenes*(LM) (Hoiseth & Stocker, *Nature* 291, 238-239 (1981); Poirier, T P et al. *J. Exp. Med.* 168, 25-32 (1988); (Sadoff, J. C., et al., *Science* 240, 336-338 (1988); Stover, C. K., et al., *Nature* 351, 456-460 (1991); Aldovini, A. et al., *Nature* 351, 479-482 (1991); Schafer, R., et al., *J. Immunol.* 149, 53-59 (1992); Ikonomidis, G. et al., *J. Exp. Med.* 180, 2209-2218 (1994)). These organisms display two promising characteristics for use as vaccine vectors: (1) enteric routes of infection, providing the possibility of oral vaccine delivery; and (2) infection of monocytes/macrophages thereby targeting antigens to professional APCs.

In addition to virus-mediated gene transfer in vivo, physical means well-known in the art can be used for direct transfer of DNA, including administration of plasmid DNA (Wolff et al., 1990, supra) and particle-bombardment mediated gene transfer (Yang, N.-S., et al., *Proc. Natl. Acad. Sci. USA* 87:9568 (1990); Williams, R. S. et al., *Proc. Natl. Acad. Sci. USA* 88:2726 (1991); Zelenin, A. V. et al., *FEBS Lett.* 280:94 (1991); Zelenin, A. V. et al., *FEBS Lett.* 244:65 (1989); Johnston, S. A. et al., *In Vitro Cell. Dev. Biol.* 27:11 (1991)). Furthermore, electroporation, a well-known means to transfer genes into cell in vitro, can be used to transfer DNA molecules according to the present invention to tissues in vivo (Titomirov, A. V. et al, *Biochim. Biophys. Acta* 1088:131 ((1991)).

"Carrier mediated gene transfer" has also been described (Wu, C. H. et al., *J. Biol. Chem.* 264:16985 (1989); Wu, G. Y. et al., *J. Biol. Chem.* 263:14621 (1988); Soriano, P. et al., *Proc. Natl. Acad. Sci. USA* 80:7128 (1983); Wang, C-Y. et al., *Proc. Natl. Acad. Sci. USA* 84:7851 (1982); Wilson, J. M. et al., *J. Biol. Chem.* 267:963 (1992)). Preferred carriers are targeted liposomes (Nicolau, C. et al., *Proc. Natl. Acad. Sci.*

USA 80:1068 (1983); Soriano et al., supra) such as immunoliposomes, which can incorporate acylated mAbs into the lipid bilayer (Wang et al., supra). Polycations such as asialoglycoprotein/polylysine (Wu et al., 1989, supra) may be used, where the conjugate includes a molecule which recognizes the target tissue (e.g., asialoorosomucoid for liver) and a DNA binding compound to bind to the DNA to be transfected. Polylysine is an example of a DNA binding molecule which binds DNA without damaging it. This conjugate is then complexed with plasmid DNA according to the present invention for transfer.

Plasmid DNA used for transfection or microinjection may be prepared using methods well-known in the art, for example using the Quiagen procedure (Quiagen), followed by DNA purification using known methods, such as the methods exemplified herein.

Having now generally described the invention, the same will be more readily understood through reference to the following examples which are provided by way of illustration, and are not intended to be limiting of the present invention, unless specified.

Example I

Materials and Methods (These examples incorporate by reference C-F Hung et al, *Canc Res.* 61:3698-3703 (2001))

Plasmid DNA Constructs and Preparation

The generation of pcDNA3-E7 has been described previously (5). For the generation of pcDNA3-ETA(dII), the pGW601 plasmid (Wozniak, D J et al, Proc Natl Acad Sci USA. 85: 8880-8884, 1988) (provided by Dr. Darrell R. Galloway at Ohio State University) was used as the template for amplification of ETA(dII). The DNA fragment containing ETA(dII) was generated using PCR with a set of primers: 5'-ccgggaattcatgcgcctgcactttcccgagggc-3' (SEQ ID NO:10) and 5'-ccggaattcgttctgcgtgccgcgggtgctgaa-3'. (SEQ ID NO:11)

The amplified DNA fragment was then cloned into the EcoRI site of pcDNA3 (Invitrogen, Carlsbad, Calif.). For the generation of pcDNA3-ETA(dII)/E7, the DNA fragment containing ETA(dII) DNA was cloned into the EcoRI site of pcDNA3-E7. For the generation of pcDNA3-GFP, DNA fragment encoding the green fluorescent protein (GFP) was first amplified with PCR using pEGFPN1 DNA (Clontech, Palo Alto, Calif.) and a set of primers: 5'-atcggatccatggtgagcaagggcgaggag-3' (SEQ ID NO:12) and 5'-gggaagctttacttgtacagctcgtccatg-3'. (SEQ ID NO: 13).

The amplified product was then cloned into the BamHI/HindIII cloning sites of pcDNA3. For the generation of pcDNA3-E7/GFP, E7 was subcloned from pcDNA3-E7 into the EcoRI/BamHI sites of pcDNA3-GFP. For the generation of pcDNA3-ETA(dII)/E7/GFP, the ETA(dII) fragment was amplified using 5'-gggtctagaatgcgcctgcactttcccgagggc-3' (SEQ ID NO:14) and
5'-ccggaattcgttctgcgtgccgcgggtgctgaa-3' (SEQ ID NO: 15)
as primers and cloned into the XbaI/EcoRI sites of pcDNA3-E7/GFP. The accuracy of all the constructs was confirmed by DNA sequencing. DNA for vaccination was prepared using an endotoxin-free kit (Qiagen, Valencia, Calif.).

Western Blot Analysis

20 μg of pcDNA3, E7, or ETA(dII)/E7 DNA were transfected into $5\times10^6$ 293 $D^bK^b$ cells (Bloom, M B et al., J Exp Med. 185: 453-459, 1997) using lipofectamine 2000 (Life Technologies, Rockville, Md.). 24 hr after transfection, cell lysates were used for Western blot analysis. Equal amounts of proteins (50 μg) were separated by SDS-PAGE using a 12% polyacrylamide gel and were electroblotted to a polyvinylidene difluoride membrane (Bio-Rad, Hercules, Calif.). Membranes were probed with E7-specific mouse monoclonal antibody (Zymed, San Francisco, Calif.) at a concentration of 0.25 μg/ml and then incubated with goat anti-mouse IgG conjugated to alkaline phosphatase (1:1000 dilution; Amersham, Piscataway, N.J.). Membranes were treated with ECL and developed using Hyperfilm-ECL (Amersham, Piscataway, N.J.).

Mice: 6- to 8-week old female C57BL/6 mice from the National Cancer Institute (Frederick, Md.) were purchased and kept in the oncology animal facility of the Johns Hopkins Hospital (Baltimore, Md.). All animal procedures were performed according to approved protocols and in accordance with recommendations for the proper use and care of laboratory animals.

CTL Assay using Transfected 293 $D^bK^b$ Cells as Target Cells

A human embryonic kidney 293 cell line expressing the $D^b$ and $K^b$ (293 $D^bK^b$) two C57BL/6 mouse MHC class I molecules, was kindly provided by Dr. J C Yang (National Cancer Institute, National Institutes of Health, Bethesda). 20 μg of pcDNA3 (no insert), ETA(dII), E7, or ETA(dII)/E7 DNA were transfected into $5\times10^6$ 293 $D^bK^b$ cells using lipofectamine 2000 (Life Technologies, Rockville, Md.). Cells were collected 40-44 hr after transfection. Transfected 293 $D^bD^b$ cells (Bloom et al., supra) were used as target cells while a $D^b$-restricted E7-specific CD8+ T cell line (Wang, T-L et al al., Gene Therapy. 7: 726-733, 2000) served as effector cells. Untransfected 293 $D^bK^b$ cells were used as a negative control. Cytolysis was determined by quantitative measurements of lactate dehydrogenase (LDH) using CytoTox96, non-radioactive cytotoxicity assay kits (Promega, Madison, Wis.) according to the manufacturer's protocol. CTL assays were performed with effector cells and targets cells ($10^4$ per well) mixed together at various ratios (1:1, 3:1, 9:1, and 27:1) in a final volume of 200 μl. After a 5 hr incubation at 37° C., 50 μl of the cultured media were collected to assess the amount of LDH in the cultured media. The percentage of lysis was calculated from the following equation:

$$\% \text{ Lysis}=100\times(A-B)/(C-D)$$

where A is the reading of experimental-effector signal value, B is the effector spontaneous background signal value, C is maximum signal value from target cells, D is the target spontaneous background signal value.

CTL Assay using DCs Pulsed with Lysates of Transfected 293 $D^bK^b$ Cells as Target Cells CTL assays were performed with freshly isolated bone marrow-derived DCs pulsed with cell lysates as target cells and E7-specific CD8+ T cells as effector cells using a protocol similar to that described previously (Lu, Z et al., J Exp Med. 191: 541-550, 2000). The protein concentration was determined using the BioRad protein assay (Bio-Rad, Hercules, Calif.) according to vendor's protocol. 293 $D^bK^b$ cells were transfected as described earlier. Cell lysates from E7 or ETA (dII)/E7 DNA-transfected 293 $D^bK^b$ cells were standardized for E7 protein concentration using an ELISA. DCs were prepared by pulsing them with different concentrations of cell lysates of various DNA-transfected 293 $D^bK^b$ cells (50 μg/ml, 10 μg/ml, 2 μg/ml and 0.4 μg/ml) in a final volume of 2 ml for 16-20 hrs. CTL assays were performed at a fixed E/T (9/1) ratio with $9\times10^4$ E7-specific T cells mixed with $1\times10^4$ prepared DCs in a final volume of 200 μl. Cytolysis was determined by quantitative measurements of LDH as described earlier.

DNA Vaccination

Preparation of DNA-coated gold particles and gene gun particle-mediated DNA vaccination was performed using a helium-driven gene gun (Bio-Rad, Hercules, Calif.) according to a previously described protocol (5). DNA-coated gold particles (1 µg DNA/bullet) were delivered to the shaved abdominal region of mice using a helium-driven gene gun (Bio-Rad, Hercules, Calif.) with a discharge pressure of 400 p.s.i.

Intracytoplasmic Cytokine Staining and Flow Cytometry Analysis

Cell surface marker staining of CD8 or CD4 and intracellular cytokine staining for IFN-γ and IL-4 as well as FACScan analysis was performed using conditions described previously (Ji et al., 1999, supra). Prior to FACScan, splenocytes from naïve or vaccinated groups of mice were incubated for 20 hours with either 1 µg/ml of E7 peptide (aa 49-57) containing MHC class I epitope for detecting E7-specific CD8$^+$ T cell precursors or 10 µg/ml of E7 peptide (aa 30-67) containing MHC class II peptide for detecting E7-specific CD4$^+$ T cell precursors.

ELISA

For detection of HPV-16 E7-specific antibodies in the sera of vaccinated mice, we performed a direct ELISA with 1:100, 1:500, and 1:1000 dilutions of sera in 1×PBS as previously described (Wu, T-C et al., Proc. Natl. Acad. Sci. 92: 11671-11675, 1995). Briefly, sera was added to microwell plates coated with bacteria-derived BPV-16 E7 proteins followed by incubation with peroxidase-conjugated rabbit anti-mouse IgG antibody (Zymed, San Francisco, Calif.).

In Vivo Tumor Protection Experiments

For the tumor protection experiment, mice (5 per group) were vaccinated via gene gun with 2 µg of pcDNA3 without insert, ETA(dII) DNA, E7 DNA, ETA(dII) mixed with E7, or chimeric ETA(dII)/E7 DNA. One week later, the mice were boosted with the same regimen as the first vaccination. One week after the last vaccination, mice were subcutaneously challenged with 5×10$^4$ cells/mouse TC-1 tumor cells (Lin et al., supra) in the right leg and then monitored twice a week.

In Vivo Tumor Treatment Experiments

Mice were intravenously challenged with 1 cells/mouse TC-1 tumor cells via tail vein on day 0. Three days after challenge with TC-1 tumor cells, mice treated with 2 µg of pcDNA3 without insert, ETA(dII) DNA, E7 DNA, or chimeric ETA(dII)/E7 DNA via gene gun. One week later, these mice were boosted with the same regimen as the first vaccination. Mice were sacrificed on day 25. The number of pulmonary metastatic nodules of each mouse was evaluated and counted by experimenters blinded to sample identity.

In Vivo Antibody Depletion Experiments

In vivo antibody depletions were performed as described previously (Lin et al., supra.) Briefly, mice were vaccinated with 2 µg ETA(dII)/E7 DNA via gene gun, boosted one week later, and challenged with 5×10$^4$ cells/mouse TC-1 tumor cells subcutaneously. Depletions were started one week prior to tumor challenge. MAb GK1.5 was used for CD4 depletion, MAb 2.43 was used for CD8 depletion, and MAb PK136 was used for NK1.1 depletion. Depletion was terminated on day 63 after tumor challenge.

Example II

Generation and Characterization of the ETA(dII)/E7 DNA Vaccine

A schematic diagram showing the domains of full-length ETA and the construct of chimeric ETA(dII)/E7 is presented in FIG. 1A. Chimeric ETA(dII)/E7 was created by linking ETA(dII) (aa 247-416) to the E7 protein. We performed a Western blot analysis to characterize protein expression in E7 and ETA(dII)/E7 DNA-transfected cells (FIG. 1B). Analysis of lysates of E7 DNA-transfected 293 D$^b$K$^b$ cells revealed a protein band with a size of approximately 15 kDa corresponding to E7 protein. Analysis of lysates of ETA(dII)/E7 DNA-transfected 293 D$^b$K$^b$ cells generated a protein band with a size of approximately 35 kDa corresponding to ETA(dII)/E7 protein. Immunoblotting with an E7-specific antibody indicated that ETA(dII)/E7 DNA-transfected cells exhibited similar levels of E7 protein expression compared to E7 DNA-transfected cells (FIG. 1B).

Example III

Figure 2:
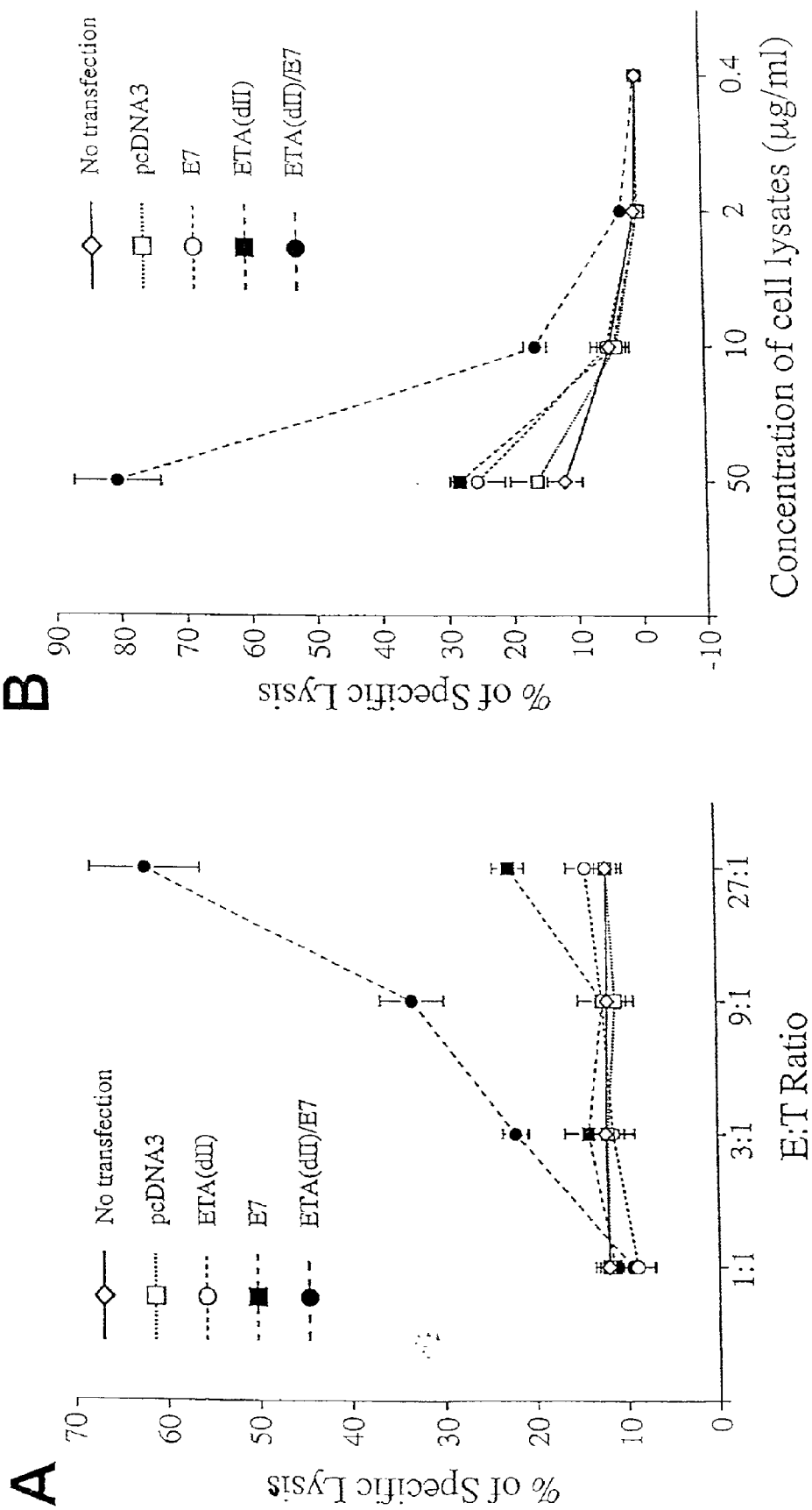
FIGS. 2A and 2B. CTL assays.
Figure 3:
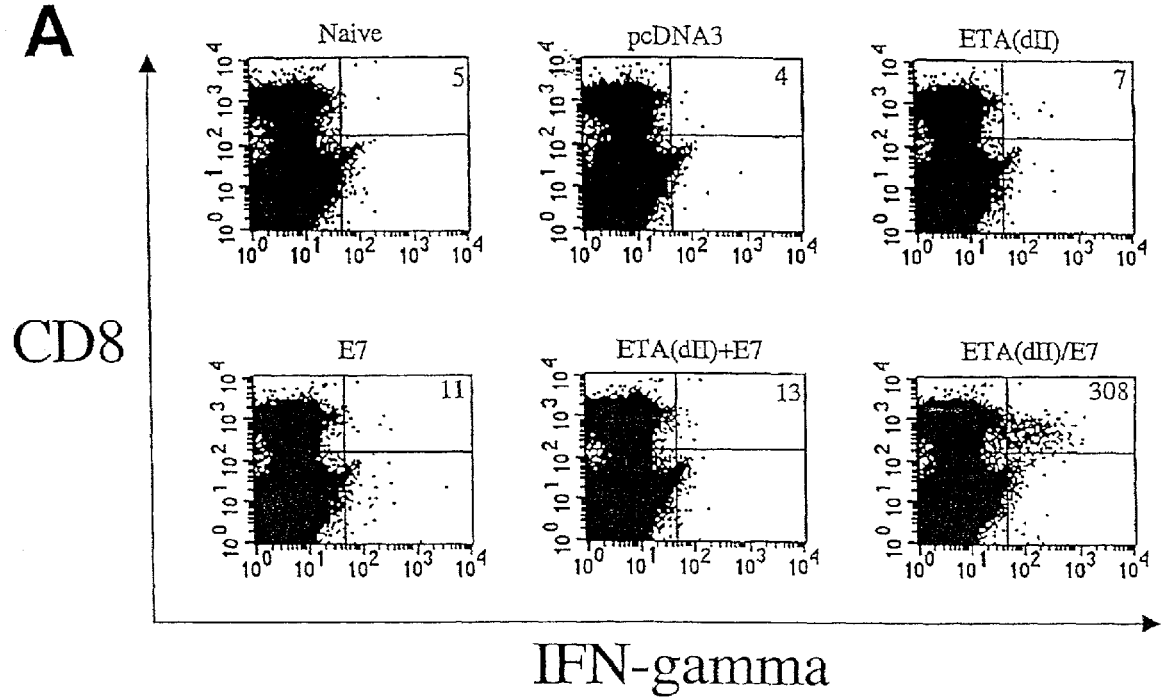
FIGS. 3A and 3B. Intracellular cytokine staining and flow cytometric analysis.
Figure 3:
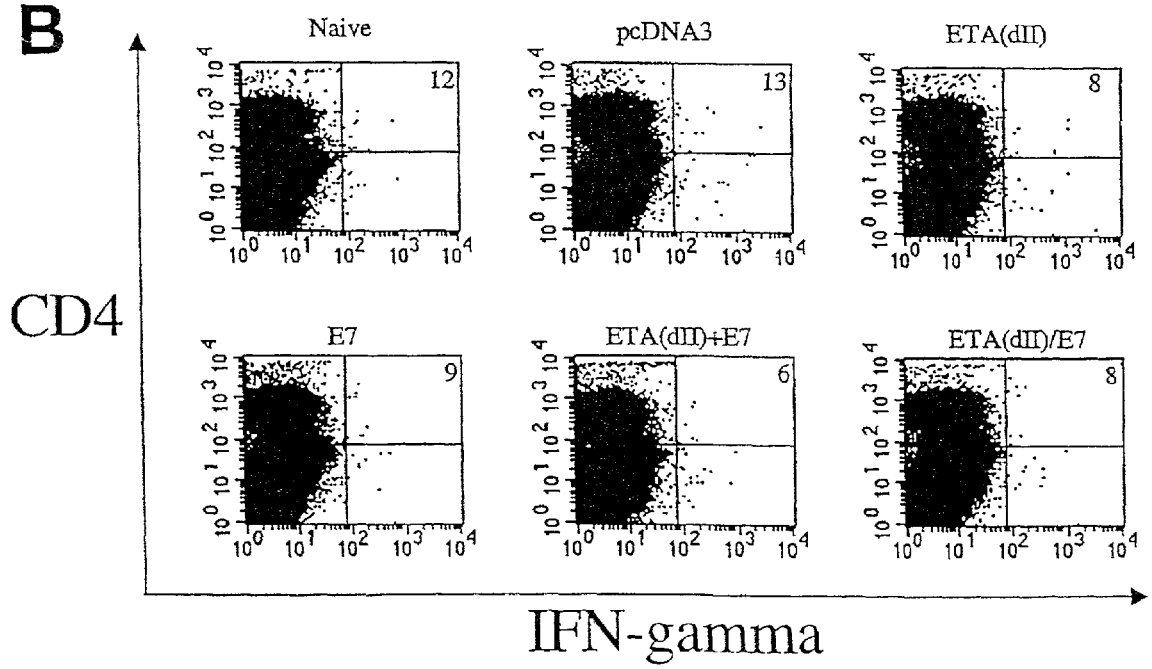
Figure 4:
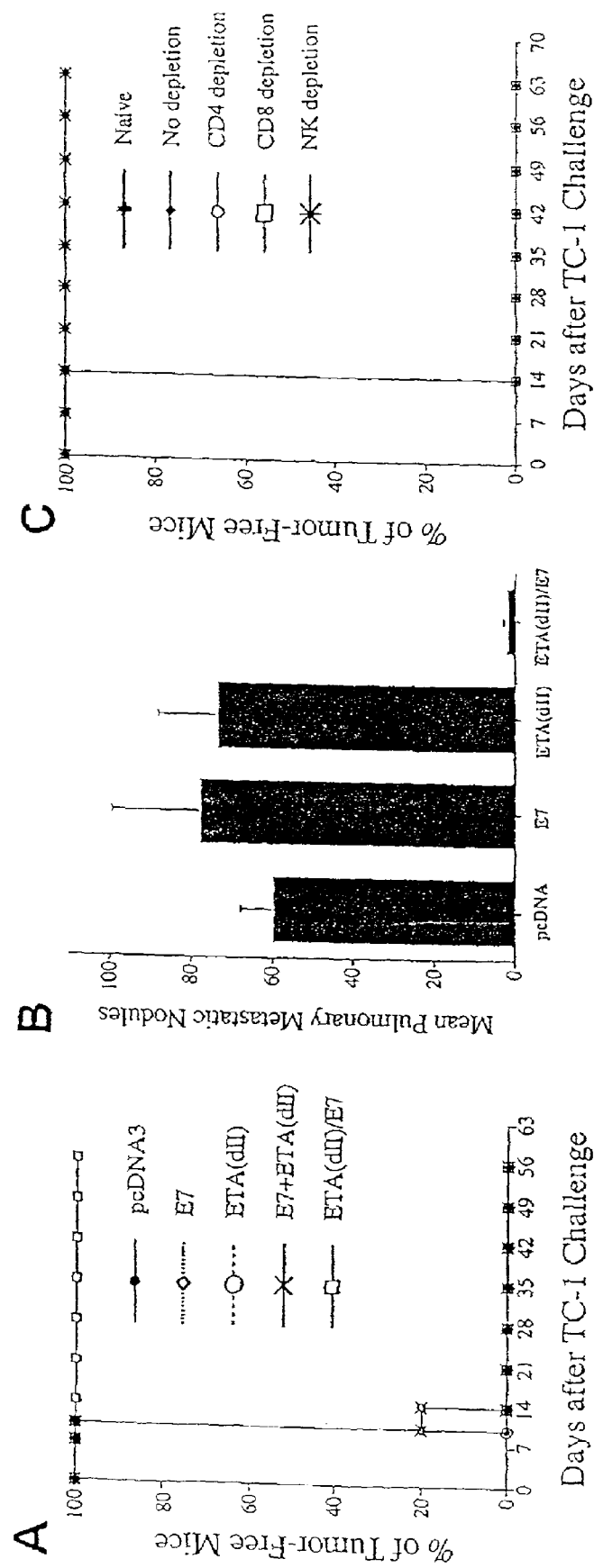
FIGS. 4A, 4B and 4C. In vivo tumor protection and therapy experiments using the TC-1 tumor, and the role of lymphocyte subsets on antitumor effects.

Enhanced Presentation of E7 Through MHC Class I Pathway in Cells Transfected with ETA(dII)/E7 DNA To test whether addition of the translocation domain of ETA to E7 can directly enhance MHC class I presentation of E7, we performed CTL assays to characterize the MHC class I presentation of E7 by 293 D$^b$K$^b$ cells transfected with various DNA constructs. We chose 293 D$^b$K$^b$ cells as target cells because they have a stable high transfection efficiency (up to 80%) and high expression of the C57BL/6 MHC class I D$^b$ molecule. T cells of A D$^b$-restricted E7-specific CD8$^+$ T cell line (26) served as effector cells. As shown in FIG. 2A, 293 D$^b$K$^b$ cells transfected with ETA(dII)/E7 DNA were killed at a significantly higher level at the 9:1 E:T ratio (33.3±3.3% versus 12.5±1.1%, p<0.001) and 27:1 (62.1±6.0% versus 22.6±3.0%, p<0.001) compared to cells transfected with wild-type E7 DNA. These results indicate that cells transfected with ETA(dII)/E7 DNA present E7 antigen through the MHC class I pathway more efficiently than cells transfected with wild-type E7 DNA.

Example IV

Enhanced Presentation of E7 through the MHC Class I Pathway in Dendritic Cells Pulsed with Lysates of Cells Transfected with Chimeric ETA(dII)/E7 DNA To demonstrate if the addition of the translocation domain of ETA to E7 can lead to enhanced MHC class I presentation of E7 via a "cross-priming" mechanism (Huang, A Y et al., Science. 264: 961-965, 1994), we performed CTL assays to characterize the MHC class I presentation of E7 using bone marrow-derived DCs pulsed with cell lysates of 293 D$^b$K$^b$ cells transfected with various DNA constructs. As shown in FIG. 2B, DCs pulsed with lysates of 293 D$^b$K$^b$ cells transfected with ETA(dII)/E7 DNA were lysed at significantly higher levels compared to (1) DCs pulsed with lysates of 293 D$^b$K$^b$ cells transfected with the other DNA constructs or (2) naïve DCs (p<0.001). These results revealed that the fusion of ETA(dII) to E7 enhances MHC class I presentation of E7 via a "cross-priming" mechanism.

Example V

Significant Enhancement of E7-Specific CD8$^+$ T Cell Precursors in Mice Vaccinated with ETA(dII)/E7 DNA To determine whether mice vaccinated with various DNA vaccine constructs generate E7-specific CD8$^+$ T cell precursors, we performed intracellular cytokine staining to detect E7-specific CD8+ T cell precursors in spleens of vaccinated mice (5). As shown in FIG. 3A, mice vaccinated with ETA (dII)/E7 DNA generated an approximately 30-fold increase in the number of E7-specific IFN-$\gamma^+$ CD8+ T cell precursors ($308/3 \times 10^5$ splenocytes) compared to mice vaccinated with E7 DNA ($11/3 \times 10^5$ splenocytes) (p<0.01). Fusion of ETA (dII) to E7 was required for enhancement of E7-specific CD8+ T cell activity because a mixture of ETA(dII) with E7 ("ETA(dII)+E7 DNA" group) did not generate enhanced CD8+ T cell activity. Furthermore, the linkage of irrelevant proteins (such as GFP and CTLA-4) to E7 did not generate enhanced E7-specific CD8+ T cell activity.

No significant differences were observed in the number of E7-specific CD4+ IFN-$\gamma^+$ T cells (FIG. 3B) or CD4+ IL-4+ T cells among each of the vaccination groups. No significant enhancement of E7-specific antibody responses was observed in mice vaccinated with ETA(dII)/E7 DNA compared to the other vaccination groups using ELISA.

Example VI

Vaccination with ETA(dII)/E7 Fusion DNA Enhances Protection Against the Growth of E7-Expressing Tumors To determine if the observed enhancement in E7-specific CD8+ T cell-mediated immunity translated to a significant E7-specific antitumor effect, we performed in vivo tumor protection studies using a previously characterized E7-expressing tumor model, TC-1 (4). As shown in FIG. 4A, 100% of mice vaccinated with ETA(dII)/E7 DNA remained tumor-free at 56 days after TC-1 challenge, while all other groups developed tumors within 15 days of challenge. Here again, fusion of ETA(dII) to E7 was required for antitumor immunity, because ETA(dII) mixed with E7 ("ETA(dII)+E7 DNA") did not enhance antitumor immunity. Furthermore, the linkage of irrelevant proteins (such as GFP and CTLA-4) to E7 did not enhance tumor protection.

Example VII

Treatment with ETA(dII)/E7 Fusion DNA Eradicates Established E7-Expressing Tumors in the Lungs To determine the therapeutic potential of chimeric ETA (dII)/E7 DNA in treating TC-1 tumor metastases in the lungs, an in vivo tumor treatment experiment was performed using a lung metastasis model (Ji, H et al., Int J Cancer. 78: 41-45, 1998). As shown in FIG. 4B, mice vaccinated with ETA(dII)/E7 DNA revealed the lowest mean number of pulmonary nodules (1.6±1.1) compared to mice vaccinated with wild-type E7 DNA (77.6±22.1), or ETA(dII) DNA (73.4±14.6) (one-way ANOVA, p<0.001). These results show that treatment with ETA(dII)/E7 could control and eradicate established E7-expressing tumors in the lungs.

Example VIII

CD8+ T Cells But Not CD4+ T cells or NK cells are Essential for the Antitumor Effect of Chimeric ETA(dII)/E7 DNA To determine the class of classes of lymphocytes participating in the rejection of E7+ tumor cells stimulated by the vaccine, we performed in vivo antibody depletion experiments. As shown in FIG. 4C, all naïve (unvaccinated) mice and all vaccinated mice depleted of CD8+ T cells grew tumors within 14 days after challenge. In contrast, all non-depleted mice and all mice depleted of CD4+ T cells or NK1.1+ cells remained tumor-free 60 days after tumor challenge. These results suggest that CD8+ T cells, but not CD4+ T cells or NK cells, are essential for the anti-tumor immunity induced by the ETA(dII)/E7 DNA vaccine.

Discussion of Examples II-VIII

Direct linkage of ETA(dII) to E7 dramatically enhanced the potency of HPV-16 E7-containing DNA vaccines. A DNA vaccine encoding ETA(dII) fused to HPV-16 E7 elicited strong E7-specific CD8+ T cell-mediated immunity and generated significant CD8+ T cell-dependent preventive effects against HPV-16 E7-expressing murine tumors. Furthermore, the chimeric ETA(dII)/E7 DNA vaccine was capable of inducing a state of immunity that successfully controlled lethal metastatic lung tumors.

The vaccine of this invention represents a successful case of employing the translocation domain of a bacterial toxin in the broader context of "gene therapy." Others employed ETA (dII) linked to a DNA-binding protein to facilitate the entry of DNA into the cytosol (Fominaya, J et al., 1996 and 1998, supra). Truncated forms of this chimeric protein lacking the translocation domain failed to facilitate efficient DNA transfer. These studies suggested the utility of ETA(dII) for introducing exogenous DNA (to be expressed as protein) into the cytosol. The precise mechanism of such translocation nevertheless remains unclear.

One explanation for the observed enhancement of E7-specific CD8+ T cell activity in mice vaccinated with ETA(dII)/E7 DNA is enhanced MHC class I presentation of E7 in cells expressing this chimeric protein. Indeed, in the in vitro studies above showed that cells transfected with ETA(dII)/E7 DNA presented E7 through the MHC class I pathway more efficiently than did cells transfected with wild-type E7 DNA (FIG. 2A). Since biolistic DNA delivery can introduce DNA directly into professional APCs in the dermis, ETA(dII)/E7 DNA-transfected APCs may directly enhance the presentation of E7 through the MHC class I pathway to CD8+ T cells and thereby contribute to the proliferation and differentiation of E7-specific CD8+ CTL precursors in vivo.

Another important mechanism contributing to the enhanced CD8+ T cell responses in vivo is the "cross-priming" effect of the chimeric protein, whereby release of ETA (dII)E7 antigen leads to uptake and re-processing by other APCs via the MHC class I-restricted pathway (Huang et al., supra). The present results show that linkage of ETA(dII) to E7 leads to enhanced priming of E7-specific CD8+ T cells presumably via "cross-priming" (FIG. 2B). One previous report disclosed that exogenous ETA (domains I and II) fused to influenza A protein or nucleoprotein resulted in MHC class I processing and presentation of the antigen to CTLs (Donnelly, J J et al., Proc Natl Acad Sci USA. 90: 3530-3534, 1993). The present results suggest that linkage to domain II alone is sufficient for delivery of exogenous antigen into the MHC class I presentation pathway.

The success of the ETA(dII)/E7 DNA vaccine described herein, and the importance of domain II in this construct points to strategies using translocation domains of other bacterial toxins to enhance vaccine potency. Translocation domains for several bacterial toxins have are known, including diphtheria toxin (Umata, T et al., J Biol Chem. 273: 8351-8359, 1998; Oh, K J et al., Proc Natl Acad Sci USA. 96: 8467-8470, 1999), clostridial neurotoxins such as tetanus neurotoxins and botulinum neurotoxins (Finkelstein, A. J Physiol. 84: 188-190, 1990; Pellizzari, R et al., Philos Trans Roy Soc Lond B Biol Sci. 354: 259-268, 1999), anthrax toxin lethal factor (Arora, N et al., Infect Immun. 62: 4955-4961, 1994; Collier, R J. J Appl Microbiol. 87: 283-288, 1999), Shiga toxin (Sandvig, K et al., Nature. 358: 510-512, 1992), E. coli heat-labile toxin (Sixma, T K et al., Nature. 355: 561-564, 1992), Yersinia cytotoxins (YopE and YopH) (Sory, M P et al., Proc Natl Acad Sci USA. 92: 11998-12002, 1995), Listeria toxin (listeriolysin 0) (Parrisius, J et al., Infect Immun. 51: 314-319, 1986), and pertussis adenylate cyclase toxin (Karimova, G et al., Proc Natl Acad Sci USA. 95: 12532-12537, 1998). Better understanding of these translocation domains may allow such molecules to be incorporated in vaccine designs similar to that described here.

ETA(dII)/E7 stimulated potent E7-specific CD8+ T cell responses through enhanced MHC class I presentation, and the antitumor effect was completely CD4-independent. Interestingly, these features resemble those recently described by the present inventors' group using a chimeric DNA vaccine that included Mycobacterium tuberculosis heat shock protein 70 (HSP70) linked to E7 (Chen, C-H et al., 2000, supra).

While the ETA(dII)/E7 targets antigen to the MHC class I presentation pathway for the enhancement of CD8+ T cell activity, other constructs that target antigen to MHC class II presentation pathways may provide enhanced CD4+ T cell responses. This realization raises the notion of co-administration of vaccines that directly enhance MHC class I and class II restricted pathways. The present inventors and their collaborators previously developed a chimeric Sig/E7/LAMP-1 DNA vaccine that uses the LAMP-1 endosomal/lysosomal targeting signal for enhancing the MHC class II presentation pathway of E7 (Ji, H et al., Human Gene Therapy. 10: 2727-2740, 1999). The ETA(dII)/E7 vaccine of the present invention used in conjunction with a MHC class II-targeting vaccine such as Sig/E7/LAMP-1 may activate multiple arms of the immune system in a synergistic fashion, leading to significantly enhanced CD4+ and CD8+ T cell responses and potent antitumor effects.

In summary, the results disclosed herein provide methods to enhance vaccine potency by linking ETA(dII) to antigen, allowing enhanced stimulation of antigen-specific CD8+ T cells leading to potent antitumor effects in vivo. Since a majority of cervical cancers express HPV E7, the present vaccine is useful for the prevention and treatment of HPV-associated tumors. This approach is useful for the control of cancer, infectious diseases and any other conditions where enhanced T cell reactivity, primarily CD8+ T cell reactivity, is associated with prophylactic or therapeutic outcomes.

The references cited above are all incorporated by reference herein, whether specifically incorporated or not.

Citation of the documents herein is not intended as an admission that any of them is pertinent prior art. All statements as to the date or representation as to the contents of these documents is based on the information available to the applicant and does not constitute any admission as to the correctness of the dates or contents of these documents.

What is claimed is:

1. A particle comprising a nucleic acid encoding a chimeric or fusion polypeptide that is an expression vector expressible in a eukaryotic cell, which nucleic acid comprises:
   (a) a first nucleotide sequence encoding a first polypeptide domain which consists of the *Pseudomonas aeruginosa* exotoxin A domain II (ETA(dII)) having SEQ ID NO: 3;
   (b) a second nucleotide sequence encoding a second polypeptide domain comprising at least one antigenic peptide; and
   (c) operably linked thereto, a promoter active in said eukaryotic cell;
   wherein the nucleic acid does not comprise a nucleotide sequence encoding a *Pseudomonas aeruginosa* exotoxin A protein other than the first polypeptide domain.

2. The particle of claim 1, wherein the antigenic peptide comprises an epitope that binds to and is presented on the cell surface by MHC class I proteins.

3. The particle of claim 2 wherein the epitope is between about 8 and about 11 amino acid residues in length.

4. The particle of claim 1, wherein the antigen
   (i) is derived from a pathogen selected from the group consisting of a mammalian cell, a microorganism or a virus; or
   (ii) cross-reacts with an antigen of the pathogen.

5. The particle of claim 1, wherein the antigen is a tumor-specific or tumor-associated antigen.

6. The particle of claim 4, wherein the virus is a human papilloma virus.

7. The particle of claim 1, wherein the antigen is an HPV-16 E6 peptide or polypeptide.

8. The particle of claim 6, wherein the antigen is an HPV-16 E7 peptide or polypeptide.

9. The particle of claim 8, wherein the HPV-16 E7 peptide or polypeptide is non-oncogenic.

10. The particle of claim 4, wherein the pathogen is a bacterium.

11. The particle of claim 8, wherein the first and the second nucleotide sequences are fused together and encode a fusion protein comprising the amino acid sequence from amino acid 1 to amino acid 269 of SEQ ID NO: 5.

12. The particle of claim 1, wherein the promoter is one that is active in a mammalian cell so that said nucleic acid is expressible in the mammalian cell.

13. The particle of claim 12, wherein the promoter is one which is expressed in an antigen presenting cell (APC).

14. The particle of claim 13, wherein the APC is a dendritic cell.

15. The particle of claim 1, wherein the promoter is one that is active in a human cell so that said nucleic acid is expressible in the human cell.

16. The particle of claim 1, wherein the first and the second nucleotide sequences are fused together and encode a fusion protein comprising the first polypeptide domain fused to the second domain.

17. The particle of claim 1, further comprising one or more regulatory elements that enhance expression of said nucleic acid in said cell.

18. The particle of claim 1, wherein the vector is a viral vector or a plasmid.

19. The particle of claim 1, wherein the vector is a self-replicating RNA replicon.

20. The particle of claim 19, wherein the self-replicating RNA replicon is a Sindbis virus RNA replicon.

21. The nucleic acid particle of claim 20, wherein the Sindbis virus RNA replicon is SINrep5.

22. The particle of claim 1, which comprises a material that is suitable for introduction into a cell or an animal by particle bombardment.

23. The particle of claim 22, wherein the material is gold.

24. An isolated mammalian cell which has been modified to comprise the particle of claim 1, and which expresses said nucleic acid.

25. The cell of claim 24, which is an APC.

26. The cell of claim 25, wherein the APC is a dendritic cell, a keratinocyte, a macrophage, a monocyte, a B lymphocyte, a microglial cell, an astrocyte, or an activated endothelial cell.

27. An isolated mammalian cell which has been modified to comprise the particle of claim 12, and which expresses said nucleic acid.

28. An isolated mammalian cell which has been modified to comprise the particle of claim 6, and which expresses said nucleic acid.

29. An isolated human cell which has been modified to comprise the particle of claim 1, and which expresses said nucleic acid.

30. A pharmaceutical composition capable of inducing or enhancing an antigen specific immune response, comprising the particle of claim 1, and a pharmaceutically acceptable carrier or excipient.

31. A pharmaceutical composition capable of inducing or enhancing an antigen specific immune response, comprising the particle of claim 6, and a pharmaceutically acceptable carrier or excipient.

32. A pharmaceutical composition capable of inducing or enhancing an antigen specific immune response, comprising the particle of claim 23, and a pharmaceutically acceptable carrier or excipient.

33. A pharmaceutical composition capable of inducing or enhancing an antigen specific immune response, comprising the cell of claim 29, and a pharmaceutically acceptable carrier or excipient.

34. A pharmaceutical composition capable of inducing or enhancing an antigen specific immune response, comprising the cell of claim 25, and a pharmaceutically acceptable carrier or excipient.

35. A pharmaceutical composition capable of inducing or enhancing an antigen specific immune response, comprising the cell of claim 24, and a pharmaceutically acceptable carrier or excipient.

36. A pharmaceutical composition capable of inducing or enhancing an antigen specific immune response, comprising the particle of claim 12, and a pharmaceutically acceptable carrier or excipient.

* * * * *

SEQUENCE LISTING

```
<160> NUMBER OF SEQ ID NOS: 15

<210> SEQ ID NO 1
<211> LENGTH: 2760
<212> TYPE: DNA
<213> ORGANISM: Pseudomonas aeruginosa
<220> FEATURE:
<221> NAME/KEY: CDS
<222> LOCATION: (746)..(2659)
<223> OTHER INFORMATION:

<400> SEQUENCE: 1
ctgcagctgg tcaggccgtt tccgcaacgc ttgaagtcct ggccgatata ccggcagggc      60
cagccatcgt tcgacgaata aagccacctc agccatgatg ccctttccat ccccagcgga     120
accccgacat ggacgccaaa gccctgctcc tcggcagcct ctgcctggcc gccccattcg     180
ccgacgcggc gacgctcgac aatgctctct ccgcctgcct cgccgcccgg ctcggtgcac     240
cgcacacggc ggagggccag ttgcacctgc cactcaccct tgaggcccgg cgctccaccg     300
gcgaatgcgg ctgtacctcg gcgctggtgc gatatcggct gctggccagg ggcgccagcg     360
ccgacagcct cgtgcttcaa gagggctgct cgatagtcgc caggacacgc cgcgcacgct     420
gaccctggcg gcggacgccg gcttggcgag cggccgcgaa ctggtcgtca ccctgggttg     480
tcaggcgcct gactgacagg ccgggctgcc accaccaggc cgagatggac gccctgcatg     540
tatcctccga tcggcaagcc tcccgttcgc acattcacca ctctgcaatc cagttcataa     600
atcccataaa agccctcttc cgctccccgc cagcctcccc gcatcccgca ccctagacgc     660
cccgccgctc tccgccggct cgcccgacaa gaaaaaccaa ccgctcgatc agcctcatcc     720
ttcacccatc acaggagcca tcgcg atg cac ctg ata ccc cat tgg atc ccc      772
                              Met His Leu Ile Pro His Trp Ile Pro
                                1               5
```

|     |     |     |     |     |     |     |     |     |     |     |     |     |     |     |     | |
|---|---|---|---|---|---|---|---|---|---|---|---|---|---|---|---|---|
| ctg | gtc | gcc | agc | ctc | ggc | ctg | ctc | gcc | ggc | ggc | tcg | tcc | gcg | tcc | gcc | 820 |
| Leu | Val | Ala | Ser | Leu | Gly | Leu | Leu | Ala | Gly | Gly | Ser | Ser | Ala | Ser | Ala | |
| 10 |     |     |     | 15 |     |     |     |     | 20 |     |     |     |     | 25 |     | |

|     |     |     |     |     |     |     |     |     |     |     |     |     |     |     |     | |
|---|---|---|---|---|---|---|---|---|---|---|---|---|---|---|---|---|
| gcc | gag | gaa | gcc | ttc | gac | ctc | tgg | aac | gaa | tgc | gcc | aaa | gcc | tgc | gtg | 868 |
| Ala | Glu | Glu | Ala | Phe | Asp | Leu | Trp | Asn | Glu | Cys | Ala | Lys | Ala | Cys | Val | |
|     |     |     |     | 30 |     |     |     |     | 35 |     |     |     |     | 40 |     | |

|     |     |     |     |     |     |     |     |     |     |     |     |     |     |     |     | |
|---|---|---|---|---|---|---|---|---|---|---|---|---|---|---|---|---|
| ctc | gac | ctc | aag | gac | ggc | gtg | cgt | tcc | agc | cgc | atg | agc | gtc | gac | ccg | 916 |
| Leu | Asp | Leu | Lys | Asp | Gly | Val | Arg | Ser | Ser | Arg | Met | Ser | Val | Asp | Pro | |
|     |     |     | 45 |     |     |     |     | 50 |     |     |     |     | 55 |     |     | |

|     |     |     |     |     |     |     |     |     |     |     |     |     |     |     |     | |
|---|---|---|---|---|---|---|---|---|---|---|---|---|---|---|---|---|
| gcc | atc | gcc | gac | acc | aac | ggc | cag | ggc | gtg | ctg | cac | tac | tcc | atg | gtc | 964 |
| Ala | Ile | Ala | Asp | Thr | Asn | Gly | Gln | Gly | Val | Leu | His | Tyr | Ser | Met | Val | |
|     |     | 60 |     |     |     |     | 65 |     |     |     |     | 70 |     |     |     | |

|     |     |     |     |     |     |     |     |     |     |     |     |     |     |     |     | |
|---|---|---|---|---|---|---|---|---|---|---|---|---|---|---|---|---|
| ctg | gag | ggc | ggc | aac | gac | gcg | ctc | aag | ctg | gcc | atc | gac | aac | gcc | ctc | 1012 |
| Leu | Glu | Gly | Gly | Asn | Asp | Ala | Leu | Lys | Leu | Ala | Ile | Asp | Asn | Ala | Leu | |
|     | 75 |     |     |     |     | 80 |     |     |     |     | 85 |     |     |     |     | |

|     |     |     |     |     |     |     |     |     |     |     |     |     |     |     |     | |
|---|---|---|---|---|---|---|---|---|---|---|---|---|---|---|---|---|
| agc | atc | acc | agc | gac | ggc | ctg | acc | atc | cgc | ctc | gaa | ggc | ggc | gtc | gag | 1060 |
| Ser | Ile | Thr | Ser | Asp | Gly | Leu | Thr | Ile | Arg | Leu | Glu | Gly | Gly | Val | Glu | |
| 90 |     |     |     |     | 95 |     |     |     |     | 100 |     |     |     |     | 105 | |

|     |     |     |     |     |     |     |     |     |     |     |     |     |     |     |     | |
|---|---|---|---|---|---|---|---|---|---|---|---|---|---|---|---|---|
| ccg | aac | aag | ccg | gtg | cgc | tac | agc | tac | acg | cgc | cag | gcg | cgc | ggc | agt | 1108 |
| Pro | Asn | Lys | Pro | Val | Arg | Tyr | Ser | Tyr | Thr | Arg | Gln | Ala | Arg | Gly | Ser | |
|     |     |     |     | 110 |     |     |     |     | 115 |     |     |     |     | 120 |     | |

|     |     |     |     |     |     |     |     |     |     |     |     |     |     |     |     | |
|---|---|---|---|---|---|---|---|---|---|---|---|---|---|---|---|---|
| tgg | tcg | ctg | aac | tgg | ctg | gta | ccg | atc | ggc | cac | gag | aag | ccc | tcg | aac | 1156 |
| Trp | Ser | Leu | Asn | Trp | Leu | Val | Pro | Ile | Gly | His | Glu | Lys | Pro | Ser | Asn | |
|     |     |     | 125 |     |     |     |     | 130 |     |     |     |     | 135 |     |     | |

|     |     |     |     |     |     |     |     |     |     |     |     |     |     |     |     | |
|---|---|---|---|---|---|---|---|---|---|---|---|---|---|---|---|---|
| atc | aag | gtg | ttc | atc | cac | gaa | ctg | aac | gcc | ggc | aac | cag | ctc | agc | cac | 1204 |
| Ile | Lys | Val | Phe | Ile | His | Glu | Leu | Asn | Ala | Gly | Asn | Gln | Leu | Ser | His | |
|     |     | 140 |     |     |     |     | 145 |     |     |     |     | 150 |     |     |     | |

|     |     |     |     |     |     |     |     |     |     |     |     |     |     |     |     | |
|---|---|---|---|---|---|---|---|---|---|---|---|---|---|---|---|---|
| atg | tcg | ccg | atc | tac | acc | atc | gag | atg | ggc | gac | gag | ttg | ctg | gcg | aag | 1252 |
| Met | Ser | Pro | Ile | Tyr | Thr | Ile | Glu | Met | Gly | Asp | Glu | Leu | Leu | Ala | Lys | |
| 155 |     |     |     |     | 160 |     |     |     |     | 165 |     |     |     |     |     | |

|     |     |     |     |     |     |     |     |     |     |     |     |     |     |     |     | |
|---|---|---|---|---|---|---|---|---|---|---|---|---|---|---|---|---|
| ctg | gcg | cgc | gat | gcc | acc | ttc | ttc | gtc | agg | gcg | cac | gag | agc | aac | gag | 1300 |
| Leu | Ala | Arg | Asp | Ala | Thr | Phe | Phe | Val | Arg | Ala | His | Glu | Ser | Asn | Glu | |
| 170 |     |     |     | 175 |     |     |     |     | 180 |     |     |     |     | 185 |     | |

|     |     |     |     |     |     |     |     |     |     |     |     |     |     |     |     | |
|---|---|---|---|---|---|---|---|---|---|---|---|---|---|---|---|---|
| atg | cag | ccg | acg | ctc | gcc | atc | agc | cat | gcc | ggg | gtc | agc | gtg | gtc | atg | 1348 |
| Met | Gln | Pro | Thr | Leu | Ala | Ile | Ser | His | Ala | Gly | Val | Ser | Val | Val | Met | |
|     |     |     | 190 |     |     |     |     | 195 |     |     |     |     | 200 |     |     | |

|     |     |     |     |     |     |     |     |     |     |     |     |     |     |     |     | |
|---|---|---|---|---|---|---|---|---|---|---|---|---|---|---|---|---|
| gcc | cag | acc | cag | ccg | cgc | cgg | gaa | aag | cgc | tgg | agc | gaa | tgg | gcc | agc | 1396 |
| Ala | Gln | Thr | Gln | Pro | Arg | Arg | Glu | Lys | Arg | Trp | Ser | Glu | Trp | Ala | Ser | |
|     |     |     |     | 205 |     |     |     |     | 210 |     |     |     |     | 215 |     | |

|     |     |     |     |     |     |     |     |     |     |     |     |     |     |     |     | |
|---|---|---|---|---|---|---|---|---|---|---|---|---|---|---|---|---|
| ggc | aag | gtg | ttg | tgc | ctg | ctc | gac | ccg | ctg | gac | ggg | gtc | tac | aac | tac | 1444 |
| Gly | Lys | Val | Leu | Cys | Leu | Leu | Asp | Pro | Leu | Asp | Gly | Val | Tyr | Asn | Tyr | |
|     |     | 220 |     |     |     |     | 225 |     |     |     |     | 230 |     |     |     | |

|     |     |     |     |     |     |     |     |     |     |     |     |     |     |     |     | |
|---|---|---|---|---|---|---|---|---|---|---|---|---|---|---|---|---|
| ctc | gcc | cag | caa | cgc | tgc | aac | ctc | gac | gat | acc | tgg | gaa | ggc | aag | atc | 1492 |
| Leu | Ala | Gln | Gln | Arg | Cys | Asn | Leu | Asp | Asp | Thr | Trp | Glu | Gly | Lys | Ile | |
| 235 |     |     |     |     | 240 |     |     |     |     | 245 |     |     |     |     |     | |

|     |     |     |     |     |     |     |     |     |     |     |     |     |     |     |     | |
|---|---|---|---|---|---|---|---|---|---|---|---|---|---|---|---|---|
| tac | cgg | gtg | ctc | gcc | ggc | aac | ccg | gcg | aag | cat | gac | ctg | gac | atc | aaa | 1540 |
| Tyr | Arg | Val | Leu | Ala | Gly | Asn | Pro | Ala | Lys | His | Asp | Leu | Asp | Ile | Lys | |
| 250 |     |     |     | 255 |     |     |     |     | 260 |     |     |     |     | 265 |     | |

|     |     |     |     |     |     |     |     |     |     |     |     |     |     |     |     | |
|---|---|---|---|---|---|---|---|---|---|---|---|---|---|---|---|---|
| ccc | acg | gtc | atc | agt | cat | cgc | ctg | cac | ttt | ccc | gag | ggc | ggc | agc | ctg | 1588 |
| Pro | Thr | Val | Ile | Ser | His | Arg | Leu | His | Phe | Pro | Glu | Gly | Gly | Ser | Leu | |
|     |     |     |     | 270 |     |     |     |     | 275 |     |     |     |     | 280 |     | |

|     |     |     |     |     |     |     |     |     |     |     |     |     |     |     |     | |
|---|---|---|---|---|---|---|---|---|---|---|---|---|---|---|---|---|
| gcc | gcg | ctg | acc | gcg | cac | cag | gct | tgc | cac | ctg | ccg | ctg | gag | act | ttc | 1636 |
| Ala | Ala | Leu | Thr | Ala | His | Gln | Ala | Cys | His | Leu | Pro | Leu | Glu | Thr | Phe | |
|     |     |     |     | 285 |     |     |     |     | 290 |     |     |     |     | 295 |     | |

|     |     |     |     |     |     |     |     |     |     |     |     |     |     |     |     | |
|---|---|---|---|---|---|---|---|---|---|---|---|---|---|---|---|---|
| acc | cgt | cat | cgc | cag | ccg | cgc | ggc | tgg | gaa | caa | ctg | gag | cag | tgc | ggc | 1684 |
| Thr | Arg | His | Arg | Gln | Pro | Arg | Gly | Trp | Glu | Gln | Leu | Glu | Gln | Cys | Gly | |
|     |     |     |     | 300 |     |     |     |     | 305 |     |     |     |     | 310 |     | |

|     |     |     |     |     |     |     |     |     |     |     |     |     |     |     |     | |
|---|---|---|---|---|---|---|---|---|---|---|---|---|---|---|---|---|
| tat | ccg | gtg | cag | cgg | ctg | gtc | gcc | ctc | tac | ctg | gcg | gcg | cgg | ctg | tcg | 1732 |
| Tyr | Pro | Val | Gln | Arg | Leu | Val | Ala | Leu | Tyr | Leu | Ala | Ala | Arg | Leu | Ser | |
|     | 315 |     |     |     |     | 320 |     |     |     |     | 325 |     |     |     |     | |

-continued

| | |
|---|---|
| tgg aac cag gtc gac cag gtg atc cgc aac gcc ctg gcc agc ccc ggc<br>Trp Asn Gln Val Asp Gln Val Ile Arg Asn Ala Leu Ala Ser Pro Gly<br>330                    335                    340                    345 | 1780 |
| agc ggc ggc gac ctg ggc gaa gcg atc cgc gag cag ccg gag cag gcc<br>Ser Gly Gly Asp Leu Gly Glu Ala Ile Arg Glu Gln Pro Glu Gln Ala<br>              350                    355                    360 | 1828 |
| cgt ctg gcc ctg acc ctg gcc gcc gcc gag agc gag cgc ttc gtc cgg<br>Arg Leu Ala Leu Thr Leu Ala Ala Ala Glu Ser Glu Arg Phe Val Arg<br>              365                    370                    375 | 1876 |
| cag ggc acc ggc aac gac gag gcc ggc gcg gcc aac gcc gac gtg gtg<br>Gln Gly Thr Gly Asn Asp Glu Ala Gly Ala Ala Asn Ala Asp Val Val<br>380                    385                    390 | 1924 |
| agc ctg acc tgc ccg gtc gcc gcc ggt gaa tgc gcg ggc ccg gcg gac<br>Ser Leu Thr Cys Pro Val Ala Ala Gly Glu Cys Ala Gly Pro Ala Asp<br>395                    400                    405 | 1972 |
| agc ggc gac gcc ctg ctg gag cgc aac tat ccc act ggc gcg gag ttc<br>Ser Gly Asp Ala Leu Leu Glu Arg Asn Tyr Pro Thr Gly Ala Glu Phe<br>410                    415                    420                    425 | 2020 |
| ctc ggc gac ggc ggc gac gtc agc ttc agc acc cgc ggc acg cag aac<br>Leu Gly Asp Gly Gly Asp Val Ser Phe Ser Thr Arg Gly Thr Gln Asn<br>                    430                    435                    440 | 2068 |
| tgg acg gtg gag cgg ctg ctc cag gcg cac cgc caa ctg gag gag cgc<br>Trp Thr Val Glu Arg Leu Leu Gln Ala His Arg Gln Leu Glu Glu Arg<br>              445                    450                    455 | 2116 |
| ggc tat gtg ttc gtc ggc tac cac ggc acc ttc ctc gaa gcg gcg caa<br>Gly Tyr Val Phe Val Gly Tyr His Gly Thr Phe Leu Glu Ala Ala Gln<br>460                    465                    470 | 2164 |
| agc atc gtc ttc ggc ggg gtg cgc gcg cgc agc cag gac ctc gac gcg<br>Ser Ile Val Phe Gly Gly Val Arg Ala Arg Ser Gln Asp Leu Asp Ala<br>475                    480                    485 | 2212 |
| atc tgg cgc ggt ttc tat atc gcc ggc gat ccg gcg ctg gcc tac ggc<br>Ile Trp Arg Gly Phe Tyr Ile Ala Gly Asp Pro Ala Leu Ala Tyr Gly<br>490                    495                    500                    505 | 2260 |
| tac gcc cag gac cag gaa ccc gac gca cgc ggc cgg atc cgc aac ggt<br>Tyr Ala Gln Asp Gln Glu Pro Asp Ala Arg Gly Arg Ile Arg Asn Gly<br>                    510                    515                    520 | 2308 |
| gcc ctg ctg cgg gtc tat gtg ccg cgc tcg agc ctg ccg ggc ttc tac<br>Ala Leu Leu Arg Val Tyr Val Pro Arg Ser Ser Leu Pro Gly Phe Tyr<br>              525                    530                    535 | 2356 |
| cgc acc agc ctg acc ctg gcc gcg ccg gag gcg gcg ggc gag gtc gaa<br>Arg Thr Ser Leu Thr Leu Ala Ala Pro Glu Ala Ala Gly Glu Val Glu<br>540                    545                    550 | 2404 |
| cgg ctg atc ggc cat ccg ctg ccg ctg cgc ctg gac gcc atc acc ggc<br>Arg Leu Ile Gly His Pro Leu Pro Leu Arg Leu Asp Ala Ile Thr Gly<br>555                    560                    565 | 2452 |
| ccc gag gag gaa ggc ggg cgc ctg gag acc att ctc ggc tgg ccg ctg<br>Pro Glu Glu Glu Gly Gly Arg Leu Glu Thr Ile Leu Gly Trp Pro Leu<br>570                    575                    580                    585 | 2500 |
| gcc gag cgc acc gtg gtg att ccc tcg gcg atc ccc acc gac ccg cgc<br>Ala Glu Arg Thr Val Val Ile Pro Ser Ala Ile Pro Thr Asp Pro Arg<br>                    590                    595                    600 | 2548 |
| aac gtc ggc ggc gac ctc gac ccg tcc agc atc ccc gac aag gaa cag<br>Asn Val Gly Gly Asp Leu Asp Pro Ser Ser Ile Pro Asp Lys Glu Gln<br>              605                    610                    615 | 2596 |
| gcg atc agc gcc ctg ccg gac tac gcc agc cag ccc ggc aaa ccg ccg<br>Ala Ile Ser Ala Leu Pro Asp Tyr Ala Ser Gln Pro Gly Lys Pro Pro<br>620                    625                    630 | 2644 |
| cgc gag gac ctg aag taactgccgc gaccggccgg ctcccttcgc aggagccggc<br>Arg Glu Asp Leu Lys<br>            635 | 2699 |

```
cttctcgggg cctggccata catcaggttt tcctgatgcc agcccaatcg aatatgaatt    2759
c                                                                    2760
```

<210> SEQ ID NO 2
<211> LENGTH: 638
<212> TYPE: PRT
<213> ORGANISM: Pseudomonas aeruginosa

<400> SEQUENCE: 2

```
Met His Leu Ile Pro His Trp Ile Pro Leu Val Ala Ser Leu Gly Leu
1               5                   10                  15

Leu Ala Gly Gly Ser Ser Ala Ser Ala Ala Glu Glu Ala Phe Asp Leu
            20                  25                  30

Trp Asn Glu Cys Ala Lys Ala Cys Val Leu Asp Leu Lys Asp Gly Val
        35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Glu Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Thr Gln Pro Arg Arg
        195                 200                 205

Glu Lys Arg Trp Ser Glu Trp Ala Ser Gly Lys Val Leu Cys Leu Leu
    210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270

Leu His Phe Pro Glu Gly Gly Ser Leu Ala Ala Leu Thr Ala His Gln
        275                 280                 285

Ala Cys His Leu Pro Leu Glu Thr Phe Thr Arg His Arg Gln Pro Arg
    290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
            340                 345                 350

Ala Ile Arg Glu Gln Pro Glu Gln Ala Arg Leu Ala Leu Thr Leu Ala
        355                 360                 365
```

```
Ala Ala Glu Ser Glu Arg Phe Val Arg Gln Gly Thr Gly Asn Asp Glu
    370                 375                 380

Ala Gly Ala Ala Asn Ala Asp Val Val Ser Leu Thr Cys Pro Val Ala
385                 390                 395                 400

Ala Gly Glu Cys Ala Gly Pro Ala Asp Ser Gly Asp Ala Leu Leu Glu
                405                 410                 415

Arg Asn Tyr Pro Thr Gly Ala Glu Phe Leu Gly Asp Gly Gly Asp Val
            420                 425                 430

Ser Phe Ser Thr Arg Gly Thr Gln Asn Trp Thr Val Glu Arg Leu Leu
        435                 440                 445

Gln Ala His Arg Gln Leu Glu Glu Arg Gly Tyr Val Phe Val Gly Tyr
    450                 455                 460

His Gly Thr Phe Leu Glu Ala Ala Gln Ser Ile Val Phe Gly Gly Val
465                 470                 475                 480

Arg Ala Arg Ser Gln Asp Leu Asp Ala Ile Trp Arg Gly Phe Tyr Ile
                485                 490                 495

Ala Gly Asp Pro Ala Leu Ala Tyr Gly Tyr Ala Gln Asp Gln Glu Pro
            500                 505                 510

Asp Ala Arg Gly Arg Ile Arg Asn Gly Ala Leu Leu Arg Val Tyr Val
        515                 520                 525

Pro Arg Ser Ser Leu Pro Gly Phe Tyr Arg Thr Ser Leu Thr Leu Ala
    530                 535                 540

Ala Pro Glu Ala Ala Gly Glu Val Arg Leu Ile Gly His Pro Leu
545                 550                 555                 560

Pro Leu Arg Leu Asp Ala Ile Thr Gly Pro Glu Glu Gly Gly Arg
                565                 570                 575

Leu Glu Thr Ile Leu Gly Trp Pro Leu Ala Glu Arg Thr Val Val Ile
            580                 585                 590

Pro Ser Ala Ile Pro Thr Asp Pro Arg Asn Val Gly Gly Asp Leu Asp
        595                 600                 605

Pro Ser Ser Ile Pro Asp Lys Glu Gln Ala Ile Ser Ala Leu Pro Asp
    610                 615                 620

Tyr Ala Ser Gln Pro Gly Lys Pro Pro Arg Glu Asp Leu Lys
625                 630                 635

<210> SEQ ID NO 3
<211> LENGTH: 171
<212> TYPE: PRT
<213> ORGANISM: Pseudomonas aeruginosa

<400> SEQUENCE: 3

Arg Leu His Phe Pro Glu Gly Gly Ser Leu Ala Ala Leu Thr Ala His
1               5                   10                  15

Gln Ala Cys His Leu Pro Leu Glu Thr Phe Thr Arg His Arg Gln Pro
            20                  25                  30

Arg Gly Trp Glu Gln Leu Glu Gln Cys Gly Tyr Pro Val Gln Arg Leu
        35                  40                  45

Val Ala Leu Tyr Leu Ala Ala Arg Leu Ser Trp Asn Gln Val Asp Gln
    50                  55                  60

Val Ile Arg Asn Ala Leu Ala Ser Pro Gly Ser Gly Gly Asp Leu Gly
65                  70                  75                  80

Glu Ala Ile Arg Glu Gln Pro Glu Gln Ala Arg Leu Ala Leu Thr Leu
                85                  90                  95

Ala Ala Ala Glu Ser Glu Arg Phe Val Arg Gln Gly Thr Gly Asn Asp
            100                 105                 110
```

```
Glu Ala Gly Ala Ala Asn Ala Asp Val Val Ser Leu Thr Cys Pro Val
        115                 120                 125
Ala Ala Gly Glu Cys Ala Gly Pro Ala Asp Ser Gly Asp Ala Leu Leu
130                 135                 140
Glu Arg Asn Tyr Pro Thr Gly Ala Glu Phe Leu Gly Asp Gly Gly Asp
145                 150                 155                 160
Val Ser Phe Ser Thr Arg Gly Thr Gln Asn Trp
            165                 170

<210> SEQ ID NO 4
<211> LENGTH: 870
<212> TYPE: DNA
<213> ORGANISM: Human papillomavirus
<220> FEATURE:
<221> NAME/KEY: CDS
<222> LOCATION: (1)..(867)
<223> OTHER INFORMATION:

<400> SEQUENCE: 4
```

| | | | | | | | | | | | | | | | | |
|---|---|---|---|---|---|---|---|---|---|---|---|---|---|---|---|---|
| atg | cgc | ctg | cac | ttt | ccc | gag | ggc | ggc | agc | ctg | gcc | gcg | ctg | acc | gcg | 48 |
| Met | Arg | Leu | His | Phe | Pro | Glu | Gly | Gly | Ser | Leu | Ala | Ala | Leu | Thr | Ala | |
| 1 | | | | 5 | | | | | 10 | | | | | 15 | | |
| cac | cag | gct | tgc | cac | ctg | ccg | ctg | gag | act | ttc | acc | cgt | cat | cgc | cag | 96 |
| His | Gln | Ala | Cys | His | Leu | Pro | Leu | Glu | Thr | Phe | Thr | Arg | His | Arg | Gln | |
| | | | 20 | | | | | 25 | | | | | 30 | | | |
| ccg | cgc | ggc | tgg | gaa | caa | ctg | gag | cag | tgc | ggc | tat | ccg | gtg | cag | cgg | 144 |
| Pro | Arg | Gly | Trp | Glu | Gln | Leu | Glu | Gln | Cys | Gly | Tyr | Pro | Val | Gln | Arg | |
| | | 35 | | | | | 40 | | | | | 45 | | | | |
| ctg | gtc | gcc | ctc | tac | ctg | gcg | gcg | cgg | ctg | tcg | tgg | aac | cag | gtc | gac | 192 |
| Leu | Val | Ala | Leu | Tyr | Leu | Ala | Ala | Arg | Leu | Ser | Trp | Asn | Gln | Val | Asp | |
| | 50 | | | | | 55 | | | | | 60 | | | | | |
| cag | gtg | atc | cgc | aac | gcc | ctg | gcc | agc | ccc | ggc | agc | ggc | ggc | gac | ctg | 240 |
| Gln | Val | Ile | Arg | Asn | Ala | Leu | Ala | Ser | Pro | Gly | Ser | Gly | Gly | Asp | Leu | |
| 65 | | | | | 70 | | | | | 75 | | | | | 80 | |
| ggc | gaa | gcg | atc | cgc | gag | cag | ccg | gag | cag | gcc | cgt | ctg | gcc | ctg | acc | 288 |
| Gly | Glu | Ala | Ile | Arg | Glu | Gln | Pro | Glu | Gln | Ala | Arg | Leu | Ala | Leu | Thr | |
| | | | | 85 | | | | | 90 | | | | | 95 | | |
| ctg | gcc | gcc | gcc | gag | agc | gag | cgc | ttc | gtc | cgg | cag | ggc | acc | ggc | aac | 336 |
| Leu | Ala | Ala | Ala | Glu | Ser | Glu | Arg | Phe | Val | Arg | Gln | Gly | Thr | Gly | Asn | |
| | | | 100 | | | | | 105 | | | | | 110 | | | |
| gac | gag | gcc | ggc | gcg | gcc | aac | gcc | gac | gtg | gtg | agc | ctg | acc | tgc | ccg | 384 |
| Asp | Glu | Ala | Gly | Ala | Ala | Asn | Ala | Asp | Val | Val | Ser | Leu | Thr | Cys | Pro | |
| | | 115 | | | | | 120 | | | | | 125 | | | | |
| gtc | gcc | gcc | ggt | gaa | tgc | gcg | ggc | ccg | gcg | gac | agc | ggc | gac | gcc | ctg | 432 |
| Val | Ala | Ala | Gly | Glu | Cys | Ala | Gly | Pro | Ala | Asp | Ser | Gly | Asp | Ala | Leu | |
| | 130 | | | | | 135 | | | | | 140 | | | | | |
| ctg | gag | cgc | aac | tat | ccc | act | ggc | gcg | gag | ttc | ctc | ggc | gac | ggc | ggc | 480 |
| Leu | Glu | Arg | Asn | Tyr | Pro | Thr | Gly | Ala | Glu | Phe | Leu | Gly | Asp | Gly | Gly | |
| 145 | | | | | 150 | | | | | 155 | | | | | 160 | |
| gac | gtc | agc | ttc | agc | acc | cgc | ggc | acg | cag | aac | gaa | ttc | atg | cat | gga | 528 |
| Asp | Val | Ser | Phe | Ser | Thr | Arg | Gly | Thr | Gln | Asn | Glu | Phe | Met | His | Gly | |
| | | | | 165 | | | | | 170 | | | | | 175 | | |
| gat | aca | cct | aca | ttg | cat | gaa | tat | atg | tta | gat | ttg | caa | cca | gag | aca | 576 |
| Asp | Thr | Pro | Thr | Leu | His | Glu | Tyr | Met | Leu | Asp | Leu | Gln | Pro | Glu | Thr | |
| | | | 180 | | | | | 185 | | | | | 190 | | | |
| act | gat | ctc | tac | tgt | tat | gag | caa | tta | aat | gac | agc | tca | gag | gag | gag | 624 |
| Thr | Asp | Leu | Tyr | Cys | Tyr | Glu | Gln | Leu | Asn | Asp | Ser | Ser | Glu | Glu | Glu | |
| | | 195 | | | | | 200 | | | | | 205 | | | | |
| gat | gaa | ata | gat | ggt | cca | gct | gga | caa | gca | gaa | ccg | gac | aga | gcc | cat | 672 |
| Asp | Glu | Ile | Asp | Gly | Pro | Ala | Gly | Gln | Ala | Glu | Pro | Asp | Arg | Ala | His | |
| | 210 | | | | | 215 | | | | | 220 | | | | | |

```
tac aat att gta acc ttt tgt tgc aag tgt gac tct acg ctt cgg ttg      720
Tyr Asn Ile Val Thr Phe Cys Cys Lys Cys Asp Ser Thr Leu Arg Leu
225                 230                 235                 240 tgc gta caa agc aca cac gta gac att cgt act ttg gaa gac ctg tta      768
Cys Val Gln Ser Thr His Val Asp Ile Arg Thr Leu Glu Asp Leu Leu
                245                 250                 255 atg ggc aca cta gga att gtg tgc ccc atc tgt tct caa gga tcc gag      816
Met Gly Thr Leu Gly Ile Val Cys Pro Ile Cys Ser Gln Gly Ser Glu
        260                 265                 270 ctc ggt acc aag ctt aag ttt aaa ccg ctg atc agc ctc gac tgt gcc      864
Leu Gly Thr Lys Leu Lys Phe Lys Pro Leu Ile Ser Leu Asp Cys Ala
            275                 280                 285 ttc tag                                                              870
Phe

<210> SEQ ID NO 5
<211> LENGTH: 289
<212> TYPE: PRT
<213> ORGANISM: Human papillomavirus

<400> SEQUENCE: 5

Met Arg Leu His Phe Pro Glu Gly Gly Ser Leu Ala Ala Leu Thr Ala
1               5                   10                  15

His Gln Ala Cys His Leu Pro Leu Glu Thr Phe Thr Arg His Arg Gln
            20                  25                  30

Pro Arg Gly Trp Glu Gln Leu Glu Gln Cys Gly Tyr Pro Val Gln Arg
        35                  40                  45

Leu Val Ala Leu Tyr Leu Ala Ala Arg Leu Ser Trp Asn Gln Val Asp
    50                  55                  60

Gln Val Ile Arg Asn Ala Leu Ala Ser Pro Gly Ser Gly Gly Asp Leu
65                  70                  75                  80

Gly Glu Ala Ile Arg Glu Gln Pro Glu Gln Ala Arg Leu Ala Leu Thr
                85                  90                  95

Leu Ala Ala Ala Glu Ser Glu Arg Phe Val Arg Gln Gly Thr Gly Asn
            100                 105                 110

Asp Glu Ala Gly Ala Ala Asn Ala Asp Val Val Ser Leu Thr Cys Pro
        115                 120                 125

Val Ala Ala Gly Glu Cys Ala Gly Pro Ala Asp Ser Gly Asp Ala Leu
    130                 135                 140

Leu Glu Arg Asn Tyr Pro Thr Gly Ala Glu Phe Leu Gly Asp Gly Gly
145                 150                 155                 160

Asp Val Ser Phe Ser Thr Arg Gly Thr Gln Asn Glu Phe Met His Gly
                165                 170                 175

Asp Thr Pro Thr Leu His Glu Tyr Met Leu Asp Leu Gln Pro Glu Thr
            180                 185                 190

Thr Asp Leu Tyr Cys Tyr Glu Gln Leu Asn Asp Ser Ser Glu Glu Glu
        195                 200                 205

Asp Glu Ile Asp Gly Pro Ala Gly Gln Ala Glu Pro Asp Arg Ala His
    210                 215                 220

Tyr Asn Ile Val Thr Phe Cys Cys Lys Cys Asp Ser Thr Leu Arg Leu
225                 230                 235                 240

Cys Val Gln Ser Thr His Val Asp Ile Arg Thr Leu Glu Asp Leu Leu
                245                 250                 255

Met Gly Thr Leu Gly Ile Val Cys Pro Ile Cys Ser Gln Gly Ser Glu
            260                 265                 270

Leu Gly Thr Lys Leu Lys Phe Lys Pro Leu Ile Ser Leu Asp Cys Ala
```

```
                275                 280                 285
Phe

<210> SEQ ID NO 6
<211> LENGTH: 297
<212> TYPE: DNA
<213> ORGANISM: Human papillomavirus
<220> FEATURE:
<221> NAME/KEY: CDS
<222> LOCATION: (1)..(297)
<223> OTHER INFORMATION:

<400> SEQUENCE: 6 atg cat gga gat aca cct aca ttg cat gaa tat atg tta gat ttg caa        48
Met His Gly Asp Thr Pro Thr Leu His Glu Tyr Met Leu Asp Leu Gln
1               5                   10                  15 cca gag aca act gat ctc tac tgt tat gag caa tta aat gac agc tca        96
Pro Glu Thr Thr Asp Leu Tyr Cys Tyr Glu Gln Leu Asn Asp Ser Ser
            20                  25                  30 gag gag gag gat gaa ata gat ggt cca gct gga caa gca gaa ccg gac       144
Glu Glu Glu Asp Glu Ile Asp Gly Pro Ala Gly Gln Ala Glu Pro Asp
        35                  40                  45 aga gcc cat tac aat att gta acc ttt tgt tgc aag tgt gac tct acg       192
Arg Ala His Tyr Asn Ile Val Thr Phe Cys Cys Lys Cys Asp Ser Thr
    50                  55                  60 ctt cgg ttg tgc gta caa agc aca cac gta gac att cgt act ttg gaa       240
Leu Arg Leu Cys Val Gln Ser Thr His Val Asp Ile Arg Thr Leu Glu
65                  70                  75                  80 gac ctg tta atg ggc aca cta gga att gtg tgc ccc atc tgt tct cag       288
Asp Leu Leu Met Gly Thr Leu Gly Ile Val Cys Pro Ile Cys Ser Gln
                85                  90                  95 gat aag ctt                                                            297
Asp Lys Leu <210> SEQ ID NO 7
<211> LENGTH: 99
<212> TYPE: PRT
<213> ORGANISM: Human papillomavirus

<400> SEQUENCE: 7

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Asp Lys Leu

<210> SEQ ID NO 8
<211> LENGTH: 5431
<212> TYPE: DNA
<213> ORGANISM: Plasmid pcDNA3

<400> SEQUENCE: 8
gacggatcgg gagatctccc gatcccctat ggtcgactct cagtacaatc tgctctgatg     60
```

```
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggac tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaacgg gccctctaga ctcgagcggc cgccactgtg ctggatatct gcagaattcc      960
accacactgg actagtggat ccgagctcgg taccaagctt aagtttaaac cgctgatcag     1020
cctcgactgt gccttctagt tgccagccat ctgttgtttg cccctccccc gtgccttcct     1080
tgaccctgga aggtgccact cccactgtcc tttcctaata aaatgaggaa attgcatcgc     1140
attgtctgag taggtgtcat tctattctgg ggggtggggt ggggcaggac agcaaggggg     1200
aggattggga agacaatagc aggcatgctg gggatgcggt gggctctatg gcttctgagg     1260
cggaaagaac cagctggggc tctaggggt atccccacgc gccctgtagc ggcgcattaa      1320
gcgcggcggg tgtggtggtt acgcgcagcg tgaccgctac acttgccagc gccctagcgc     1380
ccgctccttt cgctttcttc ccttcctttc tcgccacgtt cgccggcttt cccgtcaag      1440 ctctaaatcg gggcatccct ttagggttcc gatttagtgc tttacggcac ctcgacccca     1500
aaaaacttga ttagggtgat ggttcacgta gtgggccatc gccctgatag acggttttc      1560 gccctttgac gttggagtcc acgttcttta atagtggact cttgttccaa actggaacaa     1620
cactcaaccc tatctcggtc tattcttttg atttataagg gattttgggg atttcggcct     1680
attggttaaa aaatgagctg atttaacaaa aatttaacgc gaattaattc tgtggaatgt     1740
gtgtcagtta gggtgtggaa agtccccagg ctccccaggc aggcagaagt atgcaaagca     1800
tgcatctcaa ttagtcagca accaggtgtg gaaagtcccc aggctcccca gcaggcagaa     1860
gtatgcaaag catgcatctc aattagtcag caaccatagt cccgccccta actccgccca     1920
tcccgcccct aactccgccc agttccgccc attctccgcc ccatggctga ctaatttttt     1980
ttatttatgc agaggccgag gccgcctctg cctctgagct attccagaag tagtgaggag     2040
gcttttttgg aggcctaggc ttttgcaaaa agctcccggg agcttgtata tccattttcg     2100
gatctgatca agagacagga tgaggatcgt ttcgcatgat tgaacaagat ggattgcacg     2160
caggttctcc ggccgcttgg gtggagaggc tattcggcta tgactgggca acagacaa      2220 tcggctgctc tgatgccgcc gtgttccggc tgtcagcgca gggcgcccg gttcttttg      2280 tcaagaccga cctgtccggt gccctgaatg aactgcagga cgaggcagcg cggctatcgt     2340
ggctggccac gacgggcgtt ccttgcgcag ctgtgctcga cgttgtcact gaagcgggaa     2400
gggactggct gctattgggc gaagtgccgg ggcaggatct cctgtcatct caccttgctc     2460
```

```
ctgccgagaa agtatccatc atggctgatg caatgcggcg gctgcatacg cttgatccgg    2520
ctacctgccc attcgaccac caagcgaaac atcgcatcga gcgagcacgt actcggatgg    2580
aagccggtct tgtcgatcag gatgatctgg acgaagagca tcaggggctc gcgccagccg    2640
aactgttcgc caggctcaag gcgcgcatgc ccgacggcga ggatctcgtc gtgacccatg    2700
gcgatgcctg cttgccgaat atcatggtgg aaaatggccg cttttctgga ttcatcgact    2760
gtggccggct gggtgtggcg gaccgctatc aggacatagc gttggctacc cgtgatattg    2820
ctgaagagct tggcggcgaa tgggctgacc gcttcctcgt gctttacggt atcgccgctc    2880
ccgattcgca gcgcatcgcc ttctatcgcc ttcttgacga gttcttctga gcgggactct    2940
ggggttcgaa atgaccgacc aagcgacgcc caacctgcca tcacgagatt tcgattccac    3000
cgccgccttc tatgaaaggt tgggcttcgg aatcgttttc cgggacgccg gctggatgat    3060
cctccagcgc ggggatctca tgctggagtt cttcgcccac cccaacttgt ttattgcagc    3120
ttataatggt tacaaataaa gcaatagcat cacaaatttc acaaataaag catttttttc    3180
actgcattct agttgtggtt tgtccaaact catcaatgta tcttatcatg tctgtatacc    3240
gtcgacctct agctagagct tggcgtaatc atggtcatag ctgtttcctg tgtgaaattg    3300
ttatccgctc acaattccac acaacatacg agccggaagc ataaagtgta aagcctgggg    3360
tgcctaatga gtgagctaac tcacattaat tgcgttgcgc tcactgcccg ctttccagtc    3420
gggaaacctg tcgtgccagc tgcattaatg aatcggccaa cgcgcgggga gaggcggttt    3480
gcgtattggg cgctcttccg cttcctcgct cactgactcg ctgcgctcgg tcgttcggct    3540
gcggcgagcg gtatcagctc actcaaaggc ggtaatacgg ttatccacag aatcagggga    3600
taacgcagga aagaacatgt gagcaaaagg ccagcaaaag gccaggaacc gtaaaaaggc    3660
cgcgttgctg gcgttttttcc ataggctccg cccccctgac gagcatcaca aaaatcgacg    3720
ctcaagtcag aggtggcgaa acccgacagg actataaaga taccaggcgt ttccccctgg    3780
aagctccctc gtgcgctctc ctgttccgac cctgccgctt accggatacc tgtccgcctt    3840
tctcccttcg ggaagcgtgg cgctttctca atgctcacgc tgtaggtatc tcagttcggt    3900
gtaggtcgtt cgctccaagc tgggctgtgt gcacgaaccc cccgttcagc ccgaccgctg    3960
cgccttatcc ggtaactatc gtcttgagtc aacccggta agacacgact tatcgccact    4020
ggcagcagcc actggtaaca ggattagcag agcgaggtat gtaggcggtg ctacagagtt    4080
cttgaagtgg tggcctaact acggctacac tagaaggaca gtatttggta tctgcgctct    4140
gctgaagcca gttaccttcg gaaaaagagt tggtagctct tgatccggca acaaaccac     4200 cgctggtagc ggtggttttt ttgtttgcaa gcagcagatt acgcgcagaa aaaaaggatc    4260
tcaagaagat cctttgatct tttctacggg gtctgacgct cagtggaacg aaaactcacg    4320
ttaagggatt ttggtcatga gattatcaaa aaggatcttc acctagatcc ttttaaatta    4380
aaaatgaagt tttaaatcaa tctaaagtat atatgagtaa acttggtctg acagttacca    4440
atgcttaatc agtgaggcac ctatctcagc gatctgtcta tttcgttcat ccatagttgc    4500
ctgactcccc gtcgtgtaga taactacgat acgggagggc ttaccatctg gccccagtgc    4560
tgcaatgata ccgcgagacc cacgctcacc ggctccagat ttatcagcaa taaaccagcc    4620
agccggaagg gccgagcgca gaagtggtcc tgcaacttta tccgcctcca tccagtctat    4680
taattgttgc cgggaagcta gagtaagtag ttcgccagtt aatagtttgc gcaacgttgt    4740
tgccattgct acaggcatcg tggtgtcacg ctcgtcgttt ggtatggctt cattcagctc    4800
cggttcccaa cgatcaaggc gagttacatg atcccccatg ttgtgcaaaa aagcggttag    4860
```

| | |
|---|---|
| ctccttcggt cctccgatcg ttgtcagaag taagttggcc gcagtgttat cactcatggt | 4920 |
| tatggcagca ctgcataatt ctcttactgt catgccatcc gtaagatgct tttctgtgac | 4980 |
| tggtgagtac tcaaccaagt cattctgaga atagtgtatg cggcgaccga gttgctcttg | 5040 |
| cccggcgtca atacgggata ataccgcgcc acatagcaga actttaaaag tgctcatcat | 5100 |
| tggaaaacgt tcttcggggc gaaaactctc aaggatctta ccgctgttga gatccagttc | 5160 |
| gatgtaaccc actcgtgcac ccaactgatc ttcagcatct tttactttca ccagcgtttc | 5220 |
| tgggtgagca aaaacaggaa ggcaaaatgc cgcaaaaaag gaataagggc gacacggaa | 5280 |
| atgttgaata ctcatactct ccttttttca atattattga agcatttatc agggttattg | 5340 |
| tctcatgagc ggatacatat ttgaatgtat ttagaaaaat aaacaaatag gggttccgcg | 5400 |
| cacatttccc cgaaaagtgc cacctgacgt c | 5431 |

<210> SEQ ID NO 9
<211> LENGTH: 6221
<212> TYPE: DNA
<213> ORGANISM: Plasmid pcDNA3

<400> SEQUENCE: 9

| | |
|---|---|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca caaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaacgg gccctctaga ctcgagcggc cgccactgtg ctggatatct gcagaattca | 960 |
| tgcgcctgca ctttcccgag gcggcagcc tggccgcgct gaccgcgcac caggcttgcc | 1020 |
| acctgccgct ggagcttttc acccgtcatc gccagccgcg cggctgggaa caactggagc | 1080 |
| agtgcggcta tccggtgcag cggctggtcg ccctctacct ggcggcgcgg ctgtcgtgga | 1140 |
| accaggtcga ccaggtgatc cgcaacgccc tggccagccc cggcagcggc ggcgacctgg | 1200 |
| gcgaagcgat ccgcgagcag ccggagcagg cccgtctggc cctgacctg gccgcgccg | 1260 |
| agagcgagcg cttcgtccgg cagggcaccg gcaacgacga ggccggcgcg gccaacgccg | 1320 |
| acgtggtgag cctgacctgc ccggtcgccg cggtgaatg cgcgggccg gcggacagcg | 1380 |
| gcgacgccc gctggagcgc aactatccca ctggcgcgga gttcctcggc gacggcggcg | 1440 |
| acgtcagctt cagcacccgc ggcacgcaga acgaattcat gcatggagat acacctacat | 1500 |
| tgcatgaata tatgttagat ttgcaaccag agacaactga tctctactgt tatgagcaat | 1560 |

```
taaatgacag ctcagaggag gaggatgaaa tagatggtcc agctggacaa gcagaaccgg    1620
acagagccca ttacaatatt gtaacctttt gttgcaagtg tgactctacg cttcggttgt    1680
gcgtacaaag cacacacgta gacattcgta ctttggaaga cctgttaatg ggcacactag    1740
gaattgtgtg ccccatctgt tctcaaggat ccgagctcgg taccaagctt aagtttaaac    1800
cgctgatcag cctcgactgt gccttctagt tgccagccat ctgttgtttg cccctccccc    1860
gtgccttcct tgaccctgga aggtgccact cccactgtcc tttcctaata aaatgaggaa    1920
attgcatcgc attgtctgag taggtgtcat tctattctgg ggggtggggt ggggcaggac    1980 agcaagggg aggattggga agacaatagc aggcatgctg gggatgcggt gggctctatg    2040
gcttctgagg cggaaagaac cagctggggc tctaggggt atccccacgc gccctgtagc    2100
ggcgcattaa gcgcggcggg tgtggtggtt acgcgcagcg tgaccgctac acttgccagc    2160
gccctagcgc ccgctccttt cgctttcttc ccttcctttc tcgccacgtt cgccggcttt    2220
ccccgtcaag ctctaaatcg gggcatccct ttagggttcc gatttagtgc tttacggcac    2280
ctcgacccca aaaaacttga ttagggtgat ggttcacgta gtgggccatc gccctgatag    2340 acggttttc gcccttttgac gttggagtcc acgttcttta atagtggact cttgttccaa    2400
actggaacaa cactcaaccc tatctcggtc tattcttttg atttataagg gattttgggg    2460
atttcggcct attggttaaa aaatgagctg atttaacaaa aatttaacgc gaattaattc    2520
tgtggaatgt gtgtcagtta gggtgtggaa agtccccagg ctccccaggc aggcagaagt    2580
atgcaaagca tgcatctcaa ttagtcagca accaggtgtg gaaagtcccc aggctcccca    2640
gcaggcagaa gtatgcaaag catgcatctc aattagtcag caaccatagt cccgccccta    2700
actccgccca tcccgcccct aactccgccc agttccgccc attctccgcc ccatggctga    2760
ctaatttttt ttatttatgc agaggccgag gccgcctctg cctctgagct attccagaag    2820
tagtgaggag gcttttttgg aggcctaggc ttttgcaaaa agctcccggg agcttgtata    2880 tccatttcg gatctgatca agagacagga tgaggatcgt ttcgcatgat tgaacaagat    2940
ggattgcacg caggttctcc ggccgcttgg gtggagaggc tattcggcta tgactgggca    3000
caacagacaa tcggctgctc tgatgccgcc gtgttccggc tgtcagcgca ggggcgcccg    3060 gttcttttg tcaagaccga cctgtccggt gccctgaatg aactgcagga cgaggcagcg    3120
cggctatcgt ggctggccac gacgggcgtt ccttgcgcag ctgtgctcga cgttgtcact    3180
gaagcgggaa gggactggct gctattgggc gaagtgccgg ggcaggatct cctgtcatct    3240
caccttgctc ctgccgagaa agtatccatc atggctgatg caatgcggcg gctgcatacg    3300
cttgatccgg ctacctgccc attcgaccac caagcgaaac atcgcatcga gcgagcacgt    3360
actcggatgg aagccggtct tgtcgatcag gatgatctgg acgaagagca tcaggggctc    3420
gcgccagccg aactgttcgc caggctcaag gcgcgcatgc ccgacggcga ggatctcgtc    3480
gtgacccatg gcgatgcctg cttgccgaat atcatggtgg aaaatggccg cttttctgga    3540
ttcatcgact gtggccggct gggtgtggcg gaccgctatc aggacatagc gttggctacc    3600
cgtgatattg ctgaagagct tggcggcgaa tgggctgacc gcttcctcgt gctttacggt    3660
atcgccgctc ccgattcgca gcgcatcgcc ttctatcgcc ttcttgacga gttcttctga    3720
gcgggactct ggggttcgaa atgaccgacc aagcgacgcc caacctgcca tcacgagatt    3780
tcgattccac cgccgccttc tatgaaaggt tgggcttcgg aatcgttttc cgggacgccg    3840 gctgatgat cctccagcgc ggggatctca tgctggagtt cttcgcccac ccaaccttgt    3900
ttattgcagc ttataatggt tacaaataaa gcaatagcat cacaaatttc acaaataaag    3960
```

```
cattttttc actgcattct agttgtggtt tgtccaaact catcaatgta tcttatcatg    4020
tctgtatacc gtcgacctct agctagagct tggcgtaatc atggtcatag ctgtttcctg    4080
tgtgaaattg ttatccgctc acaattccac acaacatacg agccggaagc ataaagtgta    4140
aagcctgggg tgcctaatga gtgagctaac tcacattaat tgcgttgcgc tcactgcccg    4200
ctttccagtc gggaaacctg tcgtgccagc tgcattaatg aatcggccaa cgcgcgggga    4260
gaggcggttt gcgtattggg cgctcttccg cttcctcgct cactgactcg ctgcgctcgg    4320
tcgttcggct gcggcgagcg gtatcagctc actcaaaggc ggtaatacgg ttatccacag    4380
aatcagggga taacgcagga agaacatgt gagcaaaagg ccagcaaaag gccaggaacc    4440
gtaaaaaggc cgcgttgctg gcgttttttcc ataggctccg ccccctgac gagcatcaca    4500 aaaatcgacg ctcaagtcag aggtggcgaa acccgacagg actataaaga taccaggcgt    4560
ttccccctgg aagctccctc gtgcgctctc ctgttccgac cctgccgctt accggatacc    4620
tgtccgcctt tctcccttcg ggaagcgtgg cgctttctca atgctcacgc tgtaggtatc    4680
tcagttcggt gtaggtcgtt cgctccaagc tgggctgtgt gcacgaaccc cccgttcagc    4740
ccgaccgctg cgccttatcc ggtaactatc gtcttgagtc caacccggta agacacgact    4800
tatcgccact ggcagcagcc actggtaaca ggattagcag agcgaggtat gtaggcggtg    4860
ctacagagtt cttgaagtgg tggcctaact acggctacac tagaaggaca gtatttggta    4920
tctgcgctct gctgaagcca gttaccttcg gaaaaagagt tggtagctct tgatccggca    4980
aacaaaccac cgctggtagc ggtggttttt tgtttgcaa gcagcagatt acgcgcagaa    5040
aaaaaggatc tcaagaagat cctttgatct tttctacggg gtctgacgct cagtggaacg    5100
aaaactcacg ttaagggatt ttggtcatga gattatcaaa aaggatcttc acctagatcc    5160
ttttaaatta aaaatgaagt tttaaatcaa tctaaagtat atatgagtaa acttggtctg    5220
acagttacca atgcttaatc agtgaggcac ctatctcagc gatctgtcta tttcgttcat    5280
ccatagttgc ctgactcccc gtcgtgtaga taactacgat acgggagggc ttaccatctg    5340
gccccagtgt tgcaatgata ccgcgagacc cacgctcacc ggctccagat ttatcagcaa    5400
taaaccagcc agccggaagg gccgagcgca gaagtggtcc tgcaactttat ccgcctcca    5460 tccagtctat taattgttgc cgggaagcta gagtaagtag ttcgccagtt aatagtttgc    5520
gcaacgttgt tgccattgct acaggcatcg tggtgtcacg ctcgtcgttt ggtatggctt    5580
cattcagctc cggttcccaa cgatcaaggc gagttacatg atcccccatg ttgtgcaaaa    5640
aagcggttag ctccttcggt cctccgatcg ttgtcagaag taagttggcc gcagtgttat    5700
cactcatggt tatggcagca ctgcataatt ctcttactgt catgccatcc gtaagatgct    5760
tttctgtgac tggtgagtac tcaaccaagt cattctgaga atagtgtatg cggcgaccga    5820
gttgctcttg cccggcgtca atacgggata ataccgcgcc acatagcaga actttaaaag    5880
tgctcatcat tggaaaacgt tcttcggggc gaaaactctc aaggatctta ccgctgttga    5940
gatccagttc gatgtaaccc actcgtgcac ccaactgatc ttcagcatct tttactttca    6000
ccagcgtttc tgggtgagca aaaacaggaa ggcaaaatgc cgcaaaaaag gaataagggg    6060
cgacacggaa atgttgaata ctcatactct tcctttttca atattattga agcatttatc    6120
agggttattg tctcatgagc ggatacatat ttgaatgtat ttagaaaaat aaacaaatag    6180
gggttccgcg cacatttccc cgaaaagtgc cacctgacgt c                        6221
```

<210> SEQ ID NO 10
<211> LENGTH: 34

```
<212> TYPE: DNA
<213> ORGANISM: Artificial Sequence
<220> FEATURE:
<223> OTHER INFORMATION: Primer

<400> SEQUENCE: 10
ccgggaattc atgcgcctgc actttcccga gggc                           34

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
ccggaattcg ttctgcgtgc cgcgggtgct gaa                            33

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
atcggatcca tggtgagcaa gggcgaggag                                30

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
gggaagcttt acttgtacag ctcgtccatg                                30

<210> SEQ ID NO 14
<211> LENGTH: 33
<212> TYPE: DNA
<213> ORGANISM: Artificial Sequence
<220> FEATURE:
<223> OTHER INFORMATION: Primer

<400> SEQUENCE: 14
gggtctagaa tgcgcctgca ctttcccgag ggc                            33

<210> SEQ ID NO 15
<211> LENGTH: 33
<212> TYPE: DNA
<213> ORGANISM: Artificial Sequence
<220> FEATURE:
<223> OTHER INFORMATION: Primer

<400> SEQUENCE: 15
ccggaattcg ttctgcgtgc cgcgggtgct gaa                            33
```